United States Patent
Rogers et al.

(10) Patent No.: US 10,172,333 B2
(45) Date of Patent: Jan. 8, 2019

(54) ANIMAL MODELS OF CANCER

(71) Applicant: Exemplar Genetics, LLC, Sioux Center, IA (US)

(72) Inventors: Christopher Rogers, Coralville, IA (US); John Swart, Sioux Center, IA (US)

(73) Assignee: EXEMPLAR GENETICS, LLC, Sioux Center, IA (US)

( * ) Notice: Subject to any disclaimer, the term of this patent is extended or adjusted under 35 U.S.C. 154(b) by 317 days.

(21) Appl. No.: 14/776,564

(22) PCT Filed: Mar. 14, 2014

(86) PCT No.: PCT/US2014/029532
§ 371 (c)(1),
(2) Date: Sep. 14, 2015

(87) PCT Pub. No.: WO2014/144927
PCT Pub. Date: Sep. 18, 2014

(65) Prior Publication Data
US 2016/0007578 A1 Jan. 14, 2016

Related U.S. Application Data

(60) Provisional application No. 61/951,896, filed on Mar. 12, 2014, provisional application No. 61/788,518, filed on Mar. 15, 2013.

(51) Int. Cl.
*A01K 67/027* (2006.01)
*C12N 15/85* (2006.01)

(52) U.S. Cl.
CPC ...... *A01K 67/0275* (2013.01); *A01K 67/0278* (2013.01); *C12N 15/8509* (2013.01); *A01K 2217/052* (2013.01); *A01K 2217/072* (2013.01); *A01K 2217/15* (2013.01); *A01K 2227/108* (2013.01); *A01K 2267/0331* (2013.01); *C12N 2015/8572* (2013.01); *C12N 2800/24* (2013.01)

(58) Field of Classification Search
CPC ............ A01K 67/0275; A01K 67/0278; A01K 2217/052; A01K 2217/072; A01K 2227/108; A01K 2267/0331; C12N 15/8509; C12N 2015/8572; C12N 2800/24
See application file for complete search history.

(56) References Cited

U.S. PATENT DOCUMENTS

| 2009/0235368 A1 | 9/2009 | Welsh et al. | |
| 2010/0115636 A1 | 5/2010 | Kragh et al. | |
| 2011/0041197 A1* | 2/2011 | Frendewey | A01K 67/0275 800/24 |
| 2013/0347134 A1* | 12/2013 | Diacovo | A61K 49/0008 800/3 |

FOREIGN PATENT DOCUMENTS

| EP | 14765800 | 11/2016 | |
| WO | 2005/053512 A2 | 6/2005 | |
| WO | 2008153743 A2 | 12/2008 | |
| WO | WO-2010139511 A1 * | 12/2010 | ......... C12N 15/8509 |

OTHER PUBLICATIONS

Cao et al. J. of Exp. Zoo., 311A: 368-376, 2009.*
Brevini et al. Theriogenology, 74: 544-550, 2010.*
Paris et al. Theriogenology, 74: 516-524, 2010.*
Park et al., Reproduction, Fertility and Development, 26: 65-73, 2014.*
Whitelaw et al., J. of Pathol., 238: 247-256, 2016.*
Graham et al., Genome Biology, 16:260, 2014.*
Prather et al., Annu. Rev. Animal BioSci., 1: 203-219, Jan. 2013.*
Gün et al., BioResearch Oepn Access, 3(6): 255-264, 2014.*
Sieren, J. of Clin. Investigation, 124(9): 4052-4066, 2014.*
"Analogous." Merriam-Webster.com. Merriam-Webster, n.d. Web. May 12, 2018, p. 1.*
International Search Report and Written Opinion of PCT/US2014/029532, dated Oct. 28, 2014.
Hodges et al., Reprod Biol Endocrinol, vol. 1, No. 81, pp. 1-7, Nov. 7, 20013.
Kim et al., Reprod, Fertility and Develop, vol. 24(1), p. 124, Dec. 6, 2011.
Kim et al., Biochem and Biophys Res Comm, vol. 452, p. 901-905, 2014.
Leuches et al., Inactivation and Inducible Oncogenic Mutation of p53 in Gene Targeted Pigs, PLoS ONE, 2012, 1-8, 7(10), e43323.

* cited by examiner

*Primary Examiner* — Thaian N Ton
(74) *Attorney, Agent, or Firm* — Patrick J. Farley

(57) ABSTRACT

The present invention provides transgenic, large non-human animal models of cancer, as well as methods of using such animal models in the identification and characterization of therapies for cancer.

4 Claims, 37 Drawing Sheets
(30 of 37 Drawing Sheet(s) Filed in Color)
Specification includes a Sequence Listing.

ial Application No. PCT/US14/29248, filed on Mar. 14, 2014, which claims the benefit of U.S. Provisional Application No. 61/788,518, filed on Mar. 15, 2013 and the benefit of U.S. Provisional Application No. 61/951,896, filed on Mar. 12, 2014, each of which is hereby incorporated by reference in their entireties.

ANIMAL MODELS OF CANCER

PRIORITY

This application is the National Stage (§ 371) of International Application No. PCT/US14/29248, filed on Mar. 14, 2014, which claims the benefit of U.S. Provisional Application No. 61/788,518, filed on Mar. 15, 2013 and the benefit of U.S. Provisional Application No. 61/951,896, filed on Mar. 12, 2014, each of which is hereby incorporated by reference in their entireties.

STATEMENT AS TO FEDERALLY SPONSORED RESEARCH

Portions of this invention were made with government support under grant number CA168052 awarded by the National Institutes of Health and the National Cancer Institute. The government has certain rights to this invention.

SEQUENCE LISTING

The instant application contains a Sequence Listing which has been submitted in ASCII format via EFS-Web and is hereby incorporated by reference in its entirety. Said ASCII copy, created on Sep. 12, 2015, is named Exemplar310050SL.txt and is 32,882 bytes in size.

FIELD OF THE INVENTION

This invention relates to transgenic, non-human animal models of disease, in particular, cancer, cells that can be used to make such animals, and methods of using these animals and cells.

BACKGROUND OF THE INVENTION

Many human diseases and conditions are caused by gene mutations. Substantial effort has been directed towards the creation of transgenic animal models of such diseases and conditions to facilitate the testing of approaches to treatment, as well as to gain a better understanding of disease pathology. Early transgenic animal technology focused on the mouse, while more recent efforts, which have been bolstered by the development of somatic cell nuclear transfer (SCNT), have included larger animals, including pigs, cows, and goats. This technology has resulted in the production of, for example, pigs in which the gene encoding α-1,3-galactosyltransferase has been knocked out, in efforts to generate organs that can be used in xenotransplantation (see, e.g., Lai et al., Science 295:1089-1092, 2002). Further, this technology has resulted in the production of large animal models of human cystic fibrosis (CFTR-/- and CFTR-ΔF508/ΔF508 pigs, see, e.g., U.S. Pat. Nos. 7,989, 675 and 8,618,352, and U.S. patent application Ser. Nos. 13/368,312 and 13/624,967); and large animal models of human cardiovascular disease (LDLR+/+ and LDLR -/- pigs, see, e.g., U.S. patent application Ser. No. 13/368,312). Additional applications of this technology include the production of large quantities of human proteins (e.g., therapeutic antibodies; see, e.g., Grosse-Hovest et al., Proc. Natl. Acad. Sci. U.S.A. 101(18): 6858-6863, 2004). Substantial benefits may be obtained by the use of somatic cell nuclear transfer technology in the production of large animal models of human disease.

Cancer is the second most common cause of death in the United States, killing over 500,000 children and adults each year. See, e.g., Jemal, A., et al., *CA Cancer J Clin* (2010). Nearly 11 million Americans have a history of cancer, and an additional 1.5 million cases are diagnosed annually. The NIH estimates the annual overall cost of cancer to be more than $200 billion. The National Cancer Institute spends $4.8 billion annually on cancer research with additional funds coming from private industry and disease foundations. See, e.g., National Cancer Institute. *Cancer Research Funding*. 2010 (www.cancer.gov/cancertopics/factsheet/NCI/research-funding#a5). Yet, despite these significant expenditures, current treatments remain inadequate. All too often, therapeutic strategies that show promise in the current preclinical model systems fail to yield results in patients. This is particularly true with cancer where less than 5% of treatments that enter clinical trials are approved for use in humans. Kola, I., et al., *Nat Rev Drug Discov* 2004, 3 (8), 711-5; Hackam, D. G., et al., *JAMA* 2006, 296 (14), 1731-2. This lack of predictive efficacy in the drug development process is costly, with over 70% of all drug development costs being the result of failed drugs. An animal model that accurately replicates the progression of human cancer and shares similarities to humans in size, anatomy, physiology, and genetics would bridge the substantial gap between models currently used for early-stage drug discovery and Phase 0/I human clinical trials.

Beyond the current inefficiency in the treatment development cycle, significant challenges also remain in determining which clinically approved treatment strategy is best for each patient and confirming whether the chosen approach is effective. Non-invasive medical imaging methods have great potential to facilitate cancer treatment through lesion detection, characterization, treatment planning and monitoring. However, development and validation of new medical imaging technologies are also limited by the current model systems. Rodent models are not well suited for these applications due to their size, and current large animal models are insufficient because cancer must be induced with long-term, high-dose chemical carcinogens or tissue grafting procedures that do not resemble naturally occurring human tumors.

It has been observed in mice that carcinogenesis depends on the activation of proto-oncogenes and the deactivation of tumor suppressor genes. A mutation leading to the activation of an oncogene alone (for example, the KRAS gene) will not necessarily lead to the development of cancer, as normally functioning tumor suppressor genes (TSGs) would still function to maintain normal cell cycle. However, if TSGs are also damaged, leading to the inactivation of certain tumor suppressor proteins, unchecked cell proliferation results and leads to cancer. Conversely, a damaged TSG (for example, TP53 and ATM) would not necessarily result in cancer decoupled from the uncontrolled growth resulting from an activated oncogene.

While these observations in murine models have been helpful, they do not provide an adequate model for the development and progression of cancer in humans. Thus, a large animal model (for example, a porcine model) that is predisposed to numerous types of cancer would benefit multiple disciplines within the cancer research community. In one example, because p53 dysfunction is associated with more than half of all cancers, a large animal model with a mutation in the TSG TP53 will serve as a platform for the development of many specific cancer models. See, e.g., Bartek, J., et al., *Oncogene* 1991, 6 (9), 1699-703.

In another example, mutations in the Ataxia-Telangiectasia Mutated (ATM) gene are also associated with the development of certain types of cancer. It is known, for example, that individuals with ataxia-telangiectasia (A-T) (ATM −/−) are estimated to have a 100-fold increased risk of cancer compared with the general population. Lymphoid cancers predominate in childhood, and epithelial cancers, including breast cancer, are seen in adults. See Ahmed, M., et al., Oncogene (2006) 25, 5906-5911. It is also known that people who have only one copy of the ATM gene in each cell (ATM +/−) are at an increased risk of developing breast cancer and may have an increased risk of developing other types of cancer, for example, stomach, bladder, pancreas, lung, and ovarian. See, e.g., Shen L., et al., Mol Biol Rep. 2012 May; 39(5):5719-25. Cells that are missing one copy of the ATM gene produce half the normal amount of ATM protein, which prevents efficient repair of DNA damage and leads to the accumulation of mutations in other genes. Thus, a large animal model with a mutation in ATM would serve as a platform for the development of many specific cancer models.

In yet another example, large animal models in which tumorigenesis can be initiated in a tissue-specific manner will benefit multiple disciplines within the cancer research community. It is known, for example, that mutations in the KRAS oncogene are associated with about 30% of all human cancers Thus, an animal model having one or more mutations in the KRAS gene can be used to develop a large animal model in which tumorigenesis can be initiated in a tissue-specific manner.

In further examples of a large animal model of cancer, specific mutations introduced into a cancer-prone animal model (for example, a mutated TP53 or ATM animal model) would be extremely useful for the development of specific cancer models. In this example, a mutation in one or more genes associated with the development of cancer (for example, KRAS, TP53 and ATM) can be introduced in a large animal model having a mutation in a different gene associated with cancer development (for example, KRAS, TP53 or ATM).

Thus, in one example, because mutations in TP53 and KRAS are associated with more than half of all cancers, a large animal model with targeted mutations in the TP53 and KRAS genes would serve as a platform for the development of many specific cancer models. Bartek, J., et al., Oncogene 1991, 6 (9), 1699-703. Malumbres, M., et al., Nat Rev Cancer 2003, 3 (6), 459-65. In a similar example, a large animal model having one or more mutations in TP53 and ATM may also serve as a platform for the development of certain cancer models.

TP53 Animal Model Platform p53 (protein 53 or tumor protein 53) is strongly associated with the development of cancer in humans. Functional p53 regulates the cell division cycle and serves as a tumor suppressor in cells. p53 is activated in cells by certain stress events, for example, DNA damage, oxidative stress, osmotic shock, ribonucleotide depletion, and deregulated oncogene expression. If the TP53 gene is damaged, tumor suppression is severely reduced. For example, more than 50 percent of tumors are associated with a mutation or deletion of the TP53 gene. See Hollstein, M., et al., *Science*. 1991; 253 (5015):49-53. Further, those who inherit only one functional copy of the TP53 gene will most likely develop tumors in early adulthood, a disease known as Li-Fraumeni syndrome.

Unlike the majority of tumor suppressor genes, such as RB, APC, or BRCA1, which are usually inactivated during cancer progression by deletions or truncating mutations, the TP53 gene in human tumors is often found to undergo missense mutations, in which a single nucleotide is substituted by another. Consequently, a full-length protein containing only a single amino acid substitution is produced. The cancer-associated TP53 mutations are very diverse in their locations within the p53 coding sequence and their effects on the thermodynamic stability of the p53 protein. However, the vast majority of the mutations result in loss of p53's ability to bind DNA in a sequence-specific manner and activate transcription of canonical p53 target genes. See Hainaut P, et al., *Adv Cancer Res*. 2000; 77:81-137; Bullock A. N., et al., Nat Rev Cancer. 2001; 1:68-76; Rivlin, N., et al., Genes & Cancer 2011 2: 466.

TP53 mutations are distributed in all coding exons of the TP53 gene, with a strong predominance in exons 4-9, which encode the DNA-binding domain of the protein. Of the mutations in this domain, about 30% fall within 6 "hotspot" residues (residues R175, G245, R248, R249, R273, and R282) and are frequent in almost all types of cancer. See Cho Y., et al., Science. 1994; 265:346-55. The existence of these hotspot residues could be explained both by the susceptibility of particular codons to carcinogen-induced alterations and by positive selection of mutations that render the cell with growth and survival advantages.

It is well established that p53 inactivation and mutant p53 expression can grant cells with additive growth and survival advantages, such as increased proliferation, evasion of apoptosis, and chemoresistance. See Sigal A., et al., Cancer Res. 2000; 60:6788-93; Brosh R., et al., Nat Rev Cancer. 2009; 9:701-13. In an effort to further study the mechanisms that underlie the role of mutant p53 at the various steps of tumor progression, it is important to establish animal models that express mutant p53 in a controlled manner. Recent data obtained through the use of such in vivo models support the notion of gain of function properties acquired by mutant p53, which drive cells toward migration, invasion, and metastasis.

Earlier work revealed that although p53 knockout mice develop tumors at a high frequency, they exhibit a rather low occurrence of metastasis or invasive growth. See Donehower L. A., et al., Nature. 1992; 356:215-21; Attardi L. D., et al., Cell Mol Life Sci. 1999; 55:48-63. In contrast to this, mice knocked in with p53 R270H or R172H, corresponding to the human hotspot mutants p53R273H and p53R175H, respectively, developed highly metastatic tumors. See Lang G. A., et al., Cell. 2004; 119:861-72; Heinlein C, et al., Int J Cancer. 2008; 122:1701-9. These data support the hypothesis that TP53 mutations at early stages of tumorigenesis contribute mainly to uncontrolled proliferation, a feature of both benign and malignant tumors, whereas mutations at later stages synergize with additional oncogenic events to drive invasion and metastasis, the hallmark of malignant tumors.

While murine models of p53 mutations have provided valuable insights into the development and progression of cancer, a large animal model that more closely resembles human biology, for example, metabolism, physiology, and tumor biology, is needed to advance our understanding of cancer development and progression.

KRAS Tissue Specific Animal Model

KRAS is a potent oncogene and is mutated in about 30% of all human cancers. However, the biological context of KRAS-dependent oncogenesis is poorly understood. Genetically engineered mouse models of cancer have provided some tools to study the oncogenic process, and insights from KRAS-driven models have significantly increased understanding of the genetic, cellular, and tissue contexts in which KRAS is competent for oncogenesis. Moreover, variation among tumors arising in mouse models can provide insight into the mechanisms underlying response or resistance to therapy in KRAS-dependent cancers. Hence, it is essential that models of KRAS-driven cancers accurately reflect the genetics of human tumors and recapitulate the complex tumor-stromal intercommunication that is manifest in human cancers. See http://gan.sagepub.com/content/2/3/335.full.

It is known in the art that a specific mutation in the KRAS gene, G12D, leads to its constitutive activation. KRAS was identified as an oncogene in 1982 (see Der C. J., et al., Cell. 1983; 32:201-8) and is found to be mutated at a high frequency in human cancers including 95% of pancreatic ductal adenocarcinomas (PDAC), 50% of colon cancers, and 30% of non-small cell lung cancers (NSCLC). Overall, activating mutations in RAS are found in 32% of human cancers, including 21% with KRAS mutation, 8% with N-RAS mutation, and 3% with H-RAS mutation. See, e.g., Bos J. L., Cancer Res. 1989; 49:4682-9; Chang E H, et al., Proc Natl Acad Sci USA. 1982; 79:4848-52.

Mutational activation of KRAS results in aggressive cancers, is generally correlated with poor prognosis in cancers, and is associated with poor response to many existing therapies. See, e.g., Uberall I., et al., Exp Mol Pathol. 2008; 84:79-89; Cappuzzo F., et al., Br J Cancer. 2008; 99:83-9; Eberhard D. A., et al., J Clin Oncol. 2005; 23:5900-9. Despite the early recognition of KRAS as an oncogene, efforts to develop therapies targeting KRAS and KRAS-driven tumors have been largely unsuccessful.

In light of the multitude of effects of KRAS, including intracellular and intercellular interactions, it is critical to understand KRAS-driven tumorigenesis in a setting that recapitulates the complex biology of tumors in patients. While genetically engineered mouse models of cancer have proven to be valuable tools in cancer research, a large animal model that more closely resembles human biology and size would facilitate greater understanding of the processes involved in tumor etiology.

ATM Animal Model Platform

Mutations in the Ataxia-Telangiectasia Mutated (ATM) gene give rise to a condition known as Ataxia-Telangiectasia (A-T), described in co-pending U.S. Appln. No. 61/788,080, filed on Mar. 15, 2013, and PCT/US14/29248, filed on Mar. 14, 2014, each of which is hereby incorporated by references in their entireties. The ATM gene was first identified and cloned in 1995 (see, e.g., Savitsky, K., et al., Science, 1995. 268(5218): p. 1749-53). The ATM gene is 160 kb in length, and encodes a transcript of 13 kb spanning 66 exons. To date, at least 432 unique mutations have been identified in ATM, the majority of which are truncating or splice-site mutations that give rise to shorter, non-functional ATM proteins. ATM is a Ser/Thr protein kinase that is a member of the phosphoinositide 3-kinase (PI3K)-related protein kinase (PIKK) family, as is Rad3-related protein (ATR), both of which are involved in DNA damage response. The kinase domain of ATM is known to act on the tumor suppressor protein p53, both in vitro and in vivo, and activation of p53 is deficient in A-T cells. See, e.g., Banin, S., et al., Science, 1998. 281(5383): p. 1674-7; Canman, C. E., et al., Science, 1998. 281(5383): p. 1677-9; Khanna, K. K., et al., Nat Genet, 1998. 20(4): p. 398-400.

ATM and related proteins are known to play an important role in DNA damage repair, and loss of ATM function results in disruptions in a number of cellular pathways. Cells without any functional ATM protein are hypersensitive to radiation and do not respond normally to DNA damage. Instead of activating DNA repair, the defective ATM protein allows mutations to accumulate in other genes, which may cause cells to grow and divide in an uncontrolled way leading to the formation of cancerous tumors. Additionally, as discussed above, it is known that people who have only one copy of the ATM gene in each cell (ATM +/−) are at an increased risk of developing certain types of cancer.

Murine models of A-T have provided insights into the consequences of ATM dysfunction but do not replicate the full repertoire of clinical symptoms observed in A-T disease or in the progression and development of ATM-related cancers. While these mice are useful for investigating some of the cellular pathways in which ATM is involved, they are not ideal for studying the development of cancers associated with ATM or for testing new therapeutic approaches.

Given the examples provided by p53, ATM and KRAS, among others, a large animal model that shares anatomical, physiological, and developmental similarities with humans and more accurately models cancer development and progression could be a transformative resource, bridging the gap between the current mouse models and the development of effective treatments in humans.

Large Animal Models of Human Cancer

Provided herein are the first gene-targeted large animal models of human cancer, and human cancer development and progression. Analogous mouse models exist and have been extremely useful for understanding cancer biology and early-stage drug development, but an animal that is more similar to humans in size, anatomy, physiology, genetics, and tumor biology would be a uniquely applicable resource. A large animal model would overcome many of the disadvantages inherent in the currently available mice models, particularly with respect to size, lifespan, telomere length, cancer biology, and metabolism. Further, the large animal models disclosed herein are not intended to replace current (and future) murine models, but rather to complement existing efforts in humans and mice and provide an opportunity for multi-species, comparative approaches to fighting and preventing cancer, cancer development and/or progression.

In one example, the large animal model may be generated in, for example, a miniature pig that is more representative of average human size and lifespan (10-15 years). In such an example, porcine tumors will grow at a rate and to sizes observed in people. See, e.g., Adam, S. J., et al., *Oncogene* 2007, 26 (7), 1038-45.

In addition to the disadvantages of murine cancer models discussed above, another shortcoming of murine models of cancer is that mice have much longer telomeres than humans (40-60 kb vs. 10-15 kb) due to the presence of telomerase activity in adult cells. See, e.g., Rangarajan, A., et al., *Nat Rev Cancer* 2003, 3 (12), 952-9. In large animals, for example, in pigs, as in humans, there is little post-embryonic cellular telomerase activity, resulting in, e.g., porcine telomeres that are 15-20 kb in length. See, e.g., Jiang, L., et al., *Biol Reprod* 2004, 70 (6), 1589-93. Furthermore, porcine telomerase undergoes reactivation in cancer cells. See, e.g., Pathak, S.; Multani, A. S., et al., *Int J Oncol* 2000, 17 (6), 1219-24. Accordingly, large animal models, such as pigs, may provide a more appropriate setting for modeling the transformative events that occur in human tumorigenesis. In another example, a side by side comparison of common cancer-related genes (including TP53 and KRAS) in human, porcine, and murine fibroblasts found that pigs, like humans (but unlike mice), are highly resistant to tumorigenesis and require a similar molecular combination of genetic changes to promote cancer. See Adam, S. J., et al., *Oncogene* 2007, 26 (7), 1038-45.

Further, the large animal models disclosed herein are also more suitable with regard to metabolism. Mice metabolize drugs differently than humans, for example, in the processing of oxidants and mutagens (Rangarajan, A., et al., *Nat Rev Cancer* 2003, 3 (12), 952-9). This makes it difficult to accurately assess drug safety and toxicity, and may also explain why so many cancer therapies are successful in mice, but fail in humans. In contrast, a recent survey of 150 compounds revealed that large mammals were more predictive for human toxicity compared to rodents (63% versus 43%). See Olson H, et al., Regulatory toxicology and pharmacology: RTP 2000; 32(1):56-67 (doi: 10.1006/rtph.2000.1399. PubMed PMID: 11029269). Moreover, investigations in large animal models can be performed in a relevant, diseased setting with normal immunological response to the tumor.

One example of this is the cytochrome P450 CYP3A. Nearly half of prescription drugs are metabolized by CYP3A. See Maurel, P., CRC Press: 1996; p 241-270. While, for example, human and porcine CYP3A have similar catalytic selectivity for numerous compounds, rodent CYP3A fails to metabolize a number of common prodrugs. See, e.g., Soucek, P., et al., BMC Pharmacol 2001, 1, 11; Guengerich, F. P., Chem Biol Interact 1997, 106 (3), 161-82. Moreover, gene regulation of CYP3A in response to drugs (or other xenobiotics) greatly dictates how a drug is metabolized. A key xenosensor regulating CYP3A expression is pregnane X receptor (PXR), and porcine PXR is highly similar to its human counterpart. See, e.g., Xie, W., et al., Nature 2000, 406 (6794), 435-9; Moore, L. B., et al., Mol Endocrinol 2002, 16 (5), 977-86. This is not unexpected because, drugs are metabolized by a system that evolved to combat dietary xenobiotics, and humans and pigs are both true omnivores whereas rodents are herbivores. See Xie, W., et al., Drug Discov Today 2002, 7 (9), 509-15. Finally, the basal metabolic rate (BMR) in mammals is typically related to body size, and consequently humans and, e.g., pigs share a similar BMR, whereas the BMR of mice is seven times higher than in humans. See, e.g., Randall, D., Ekert Animal Physiology: Mechanisms and Adaptions, 5th ed.; W.H. Freeman and Company: 2001; Ames, B. N., et al., Proc Natl Acad Sci USA 1993, 90 (17), 7915-22. Accordingly, larger animals models, including a porcine model, may be more appropriate preclinical models for drug toxicity than rodents. In fact, in a recent survey of 150 compounds revealed that large mammals were more predictive for human toxicity compared to rodents (63% versus 43%). See Olson, H., et al., Regul Toxicol Pharmacol 2000, 32 (1), 56-67.

The large animal models disclosed herein allow for testing of therapeutic approaches to cancer that are impossible in smaller animals, such as intensity-modulated radiation and local hyperthermia. A large animal model (for example, a porcine model), will also serve an unmet need in medical imaging and surgical training. For example, noninvasive image-guided technologies including next generation MRI, ultrasound, nuclear imaging, x-ray and optical imaging techniques could be evaluated in, e.g., pigs using instrumentation designed for humans. In the context of surgical training, a large animal model (for example, a porcine model) would allow refinement of surgical techniques using standard approaches, as well as minimally invasive and robotic technologies. Further, these investigations would all be performed in a relevant, diseased setting.

SUMMARY OF THE INVENTION

Provided herein are large, non-human animal models of human diseases or conditions, in which one or more genes associated with a disease or condition include one or more targeted mutations. The animals can be, for example, ungulates such as pigs, cows, sheep, and goats. In one example, the disease or condition is human cancer, human cancer development or cancer progression.

In one example, the animal models provided herein may include a mutation(s) in one or both alleles of a target gene in the genome of the transgenic animal, and the mutation(s) can result in full or partial inactivation of the gene. In another example, the animal models provided herein may include a mutation(s) in one or both alleles of a target gene in the genome of the transgenic animal, and the mutation(s) can result in activation or overexpression of the gene. In yet another example, the animal models provided herein may include a mutation(s) in one or both alleles of a target gene in the genome of the transgenic animal, and the mutation(s) can result in expression of a mutated gene product. In the case of an animal with a mutation or mutations in both alleles of a gene, the mutation or mutations in each allele can be identical to one another or can be different.

In one example, the mutation(s) substantially eliminates expression of a functional gene product of the targeted gene in cells in which such expression normally takes place, absent the mutation. In contrast, the mutation(s) can also result in activation or overexpression of a gene product of the targeted gene in cells in which such expression would normally not occur, or occur at a lower rate, absent the mutation. In yet another example, the mutation(s) can result in the introduction of a mutated form of a gene product into a cell that dominates or otherwise affects expression of the wild-type gene product, e.g., a "gain of function" (GOF) mutation.

In one example, the mutation includes an insertion of an exogenous nucleic acid molecule and/or a transcription/translation termination sequence. In another example, the mutation includes a deletion of an endogenous nucleic acid molecule or a portion thereof. In yet another example, the mutation introduces an alteration in the genetic sequence, for example, a point mutation or a missense mutation.

In these examples, the large animal models described herein provide a platform model of human cancer, cancer development or cancer progression. In one example, the target gene is TP53, ATM or KRAS. Thus, in one example, the large animals of the present invention include a mutation(s) in one or both alleles of a target gene such as TP53, ATM or KRAS. In one example, the mutation in the large animal (for example, porcine) models of the present invention is a TP53 mutation orthologous to one commonly found in humans, for example, the R175H mutation in people, which is the equivalent of the R167H in porcine.

In another example, the target gene is KRAS and the large animal model comprises a genotype that includes a mutation in at least one TP53 allele. In yet another example, the target gene is ATM and the large animal model comprises a genotype that includes a mutation in at least one TP53 allele. Thus, in one example of an animal model of the present invention, a mutation in one or both alleles of a target gene (for example, TP53, ATM or KRAS) is introduced by the methods disclosed herein, and that animal model is used to generate a further animal model wherein a mutation in one or both alleles of a different gene (for example, TP53, ATM or KRAS) is introduced.

Hence, in one aspect, the animal models provided herein may include a mutation in one or both alleles of at least two target genes in the genome of the transgenic animal. In another example, the animal models provided herein may include a mutation in one or both alleles of at least two target genes in the genome of the transgenic animal, and the mutations can result in full or partial inactivation of at least one or at least two target genes. In another example, the animal models provided herein may include a mutation in one or both alleles of at least two target genes in the genome of the transgenic animal, and the mutations can result in activation or overexpression of at least one or at least two target genes. In another example, the animal models provided herein may include a mutation in one or both alleles of at least two target genes in the genome of the transgenic animal, and the mutations can result in full or partial inactivation of a target gene while resulting in the overexpression of another target gene. In yet another example, the animal models provided herein may include a mutation in one or both alleles of at least two target genes in the genome of the transgenic animal, and the mutations can result in full or partial inactivation of a target gene while resulting expression of a mutated form of another target gene.

In one example, a mutation is introduced in at least one TP53 allele of an animal, for example, a swine, causing inactivation of the production of functional p53, and a second mutation is introduced to enhance the development of cancer in the animal, either by activating or deactivating a second gene. In one further embodiment of this example, a second mutation is introduced in at least one ATM allele of the animal in the presence of inactivation of TP53, and said second mutation results in the reduced expression or non-expression of functional ATM. In another further embodiment of this example, a second mutation is introduced in at least one KRAS allele of the animal in the presence of inactivation of TP53, and said second mutation results in the expression of a mutated form of KRAS, or the overexpression of KRAS.

In another example, an activating mutation in introduced in the KRAS gene of a large animal, for example, a swine. In one embodiment, the activating mutation is a G12D mutation.

In another example, a large animal model (e.g., swine), is generated in which the endogenous tumor suppressor p53 is mutated and a mutant proto-oncogene KRAS allele is conditionally activated in a temporal- and tissue-specific manner. Importantly, the ability to activate mutant KRAS temporally and spatially in a TP53 mutant background permits both childhood and adult cancer to be modeled in essentially any tissue, thereby allowing the animals of the invention to model almost any human cancer. In one embodiment, the model of the present invention is used to generate cancers of the lung and pancreas.

In a further example of these embodiments of the invention, a KRAS mutation is introduced in a large animal (for example, swine) in which at least one TP53 allele has been mutated or inactivated. In one example, the TP53 mutation is the introduction of the R167H mutation in a swine model of the present invention. In a further example, a G12D mutation is introduced into at least one KRAS allele in a large animal model (for example, porcine) in which the R167H mutation has been introduced into at least one TP53 allele of said large animal model.

The animal models provided herein may also include a homologous transgenic copy of a wild-type or mutated gene from a different animal. In one embodiment, the animal models may include an orthologous gene from a different animal. The animal models may thus include, for example, in addition to a mutation/inactivation of an endogenous gene, an inserted copy of a corresponding gene from another species. Thus, for example, an animal (such as a pig) in which an endogenous gene (for example, TP53, ATM and/or KRAS) is mutated may be modified to include a gene (for example, TP53, ATM and/or KRAS) from another animal (such as a human), which may be wild-type or may include a mutation.

In one example, provided herein are transgenic, large (non-human) animal models of human diseases and conditions in which one or more endogenous genes associated with the disease or condition are knocked-out (i.e., genetically altered in such a way as to inhibit the production or function of the product or gene) and replaced with a homologous wild-type or mutated gene derived from a different animal (e.g., a human). In one example, a pig with its endogenous porcine TP53, ATM and/or KRAS gene knocked-out expresses a human transgene encoding a TP53 gene, ATM gene, and/or KRAS gene, or a mutation thereof.

Also provided herein are isolated cells of transgenic, large non-human animal models of human diseases or conditions, in which one or more genes associated with the diseases or conditions include one or more targeted mutations. The animals can be, for example, ungulates, such as, e.g., pigs, cows, sheep, and goats. In one example, the disease or condition is cancer, cancer development or cancer progression. In another example, the disease or condition is cancer, cancer development or cancer progression, and a gene(s) including one or more mutations is the TP53, ATM and/or KRAS gene(s).

Examples of mutations that may be present in the animals and cells disclosed herein include mutations affecting the synthesis of a target gene, for example, TP53, ATM and/or KRAS. These mutations include, for example, mutations that prevent any functional protein product from being produced, and mutations that give rise to the production of an abnormal version of protein that retains some function or induces a different function into the cell than the wild-type protein. Further examples of mutations that may be present in the animals and cells disclosed herein include mutations that give rise to the production of an abnormal amount of a protein.

In the case of a cell with a mutation or mutations in both alleles of a gene, the mutation or mutations in each allele can be identical to one another or can be different. In one example, the cells are fetal cells, such as fetal fibroblasts. Additional examples of cell types included in the invention are provided below.

The invention further provides methods of making transgenic, large non-human animal models of diseases or conditions as described above and elsewhere herein. The methods can include the steps of: (i) introducing one or more mutations into an allele of one or more genes associated with a disease or condition in a cell (e.g., a fetal fibroblast) to generate a donor cell; (ii) introducing the nucleus of the donor cell into a recipient cell (e.g., an enucleated oocyte) to generate an embryo; and (iii) transferring the embryo into a surrogate female. The animals can be, for example, ungulates, such as, e.g., pigs, cows, sheep, and goats. In one example, the disease or condition is cancer and the gene including one or more mutations is a TP53, KRAS or ATM gene. In a variation of these methods, the donor cell includes one or more mutations in one allele of a TP53, KRAS or ATM gene. In another variation of these methods, the donor cell includes one or more mutations in one allele of a TP53, KRAS or ATM gene, and the method is carried out to introduce one or more mutations into the other allele of the same gene. In another example, the methods further involve breeding an animal that is born from the surrogate female to obtain a mutant animal that has one or more mutations in the other TP53, KRAS or ATM allele.

In a further example, the donor cell created using the methods described herein includes one or more mutations in at least one allele of a TP53, KRAS or ATM gene, and the method is carried out to introduce one or more mutations in at least one allele of a different gene (selected from, e.g., TP53, KRAS or ATM) in such donor cell. For example, a donor cell may include a mutation in at least one allele of a TP53 gene and the method is carried out to introduce one or more mutations in at least one allele selected from KRAS or ATM In another example, the methods further involve breeding an animal having one or more mutations in at least one allele of a TP53 gene with an animal having one or more mutations in at least one allele selected from, e.g., KRAS or ATM.

The invention also includes methods of identifying therapeutic agents that can be used in the treatment of diseases or conditions (e.g., cancer, cancer development or cancer progression). These methods involve administering one or more candidate therapeutic agents to a transgenic animal, as described above, and monitoring the animal for one or more symptoms of the disease or condition. Detection of improvement or other change in a symptom of the disease or condition indicates the identification of a compound that may be used in the treatment or prevention of the disease or condition.

The invention also includes methods of providing surgical training and medical imaging that can be used in the treatment of diseases or conditions (e.g., cancer, cancer development or cancer progression). These methods involve using the transgenic animals of the present invention for the refinement of surgical techniques using standard approaches, as well as minimally invasive and robotic technologies. In the context of medical imaging, new and improved technologies including noninvasive imaging could be evaluated using instrumentation designed for humans.

The invention further provides methods of targeting the introduction of mutations into large animal cells, e.g., pig cells. These methods involve the steps of providing such cells (e.g., fetal fibroblasts), using a recombinant adeno-associated viral (rAAV) vector (also referred to herein as an adeno-associated viral (AAV) vector) to deliver a gene targeting construct to the isolated pig cells, in the absence of cell detachment and reattachment, and selecting gene-targeted clones. The cells are in culture for 30 days or less (e.g., 20 days or less in the Examples) during the targeting construct delivery and selection steps. These methods can be used, for example, for the introduction of a mutation into a TP53, ATM and/or KRAS gene in a large animal cell. Information concerning other examples of mutations that can be used in the present invention, as well as the use of the present methods to inactivate or replace genes (e.g., to replace pig genes with human genes), is provided below.

By "donor cell" is meant a cell from which a nucleus or chromatin material is derived, for use in nuclear transfer. Nuclear transfer can involve transfer of a nucleus or chromatin only, as isolated from a donor cell, or transfer of an entire donor cell including such a nucleus or chromatin material.

By "genetic modification," "mutation," or "disruption" of a gene (e.g., a TP53, ATM or KRAS gene) is meant one or more alterations in gene sequences (including coding sequences and non-coding sequences, such as introns, promoter sequences, and 5' and 3'-untranslated sequences) that alter the expression or activity of this gene by, for example, insertion (of, e.g., heterologous sequences, such as selectable markers, and/or termination signals), deletion, frame shift mutation, silent mutation, nonsense mutation, missense mutation, point mutation, or combinations thereof. In one example, the amino acid sequence encoded by the nucleic acid sequence has at least one amino acid altered as compared to a naturally-occurring sequence. Examples of mutations include the insertion of a polynucleotide into a gene, the deletion of one or more nucleotides from a gene, and the introduction of one or more base substitutions into a gene.

In one embodiment of the present invention, modifications of TP53 or ATM gene sequences are those that lead to one or more features or symptoms of cancer, cancer development or cancer progression in transgenic animals including a mutation in, or disruption of, at least one of TP53 or ATM allele. In another embodiment of the present invention, modifications of TP53 or ATM gene sequences are those that result in a mutation in, or disruption of, both TP53 or ATM alleles. As is discussed elsewhere herein, the modifications in the two TP53 or ATM alleles of such animals can be identical or different. Further, the modifications can result in a complete lack of functional p53 or ATM production, or can result in diminished functional p53 or ATM production.

In another embodiment of the present invention, modifications of KRAS gene sequences are those that lead to one or more features or symptoms of cancer, cancer development or cancer progression in transgenic animals including a mutation in, activation of, or disruption of, at least one of the KRAS alleles. The modifications can result in a complete lack of functional KRAS production, increased functional or mutant KRAS production, or diminished functional KRAS production. Further, modifications of KRAS gene sequences may result in the conditional expression of activated KRAS. This is accomplished by using Cre-recombinase to excise a STOP cassette that would normally be blocking expression of the mutant KRAS, as is shown in FIG. 5.

In one embodiment, modifications of at least one TP53 allele and at least one KRAS allele are present in the same large animal model.

In one example, a mutation is introduced by the insertion of a polynucleotide (for example, a positive selection marker, such as an antibiotic resistance gene (e.g., a neomycin resistance gene)) into an endogenous gene. Optionally, a mutation that is introduced into such an endogenous gene reduces or increases the expression of the gene, or leads to the expression of a mutated gene product. If desired, the polynucleotide may also contain recombinase sites flanking the positive selection marker, such as loxP sites, so that the positive selection marker may be removed by a recombinase (e.g., cre recombinase).

By "homologous" genes is meant a pair of genes from two animal species that encode proteins having similar functional and physical properties. The proteins encoded by homologous genes are often very similar in structure and function (although not always), and typically have a common evolutionary origin. In one embodiment, the sequence identity is typically equal to or greater than 80%, equal to or greater than 90%, equal to or greater than 95%, or equal to or greater than 98% between two gene homologs. One example of a homologous gene pair is the porcine TP53, ATM and human TP53 gene loci. Another example of a homologous gene pair is the porcine KRAS, ATM and human KRAS gene loci.

By "orthologous" genes or "orthologs" is meant genes that are separated by a speciation event wherein one ortholog may be substituted by genetic engineering into its corresponding gene in another species.

By animal "knock-out" is meant an animal (for example, a pig or mouse; also see other animals described herein) having a genome in which the function of a gene has been disrupted, or "knocked-out." A common method of producing disabled genes using recombinant DNA technology involves inserting an antibiotic resistance gene into the normal DNA sequence of a clone of the gene of interest by homologous recombination. This disrupts the action of the gene, thereby preventing it from leading to the production of an active protein product. A cell (or cell nucleus) in which this transfer is successful can be injected into a recipient cell (e.g., an enucleated oocyte) to generate a transgenic animal by nuclear transfer. In another approach, the cell is injected into an animal embryo, producing a chimeric animal. These animals are bred to yield a strain in which all of the cells contain the knocked-out gene.

By "heterozygous knock-out non-human mammal" is meant a mammal other than a human in which one of the two alleles of an endogenous gene have been genetically targeted, or knocked out, resulting in a marked reduction or elimination of expression of a functional gene product, which is achieved by gene deletion or disruption.

By "homozygous knock-out non-human mammal" is meant a mammal other than a human in which the two alleles of an endogenous gene have been genetically targeted, or knocked out, resulting in a marked reduction or elimination of expression of a functional gene product, which is achieved by gene deletion or disruption. According to the invention, the genetic targeting event at both alleles may or may not be the same. Thus, a non-human animal, in which the two alleles of an endogenous gene have been genetically targeted by two different targeting vectors resulting in the null expression of the gene, would be considered as being a homozygous knock-out non-human mammal.

An example of a "knock-in mutation" is one resulting in the insertion of a mutation into an endogenous gene. The mutation may include a missense mutation (as described in the Examples). Alternatively, the mutation may also include the insertion of a promoter to conditionally express a gene product or a mutated gene product.

By "recipient cell" is meant a cell into which a donor cell, a donor cell nucleus, or donor cell chromatin is introduced. In one preferred embodiment, recipient cells are enucleated prior to nuclear transfer. Examples of recipient cells include oocytes, fertilized zygotes, and two-cell embryos.

By "transgenic, large non-human animal" is meant any non-human animal that includes a genetic modification, as defined herein. Examples of such animals include animals other than mice such as, for example, ungulates. Examples of ungulates that can be used in the invention include members of the orders Perissodactyla and Artiodactyla, such as any members of the family Suidae, and in particular any member of the genus *Sus*, such as *Sus scrofa*, which is also known as the domestic pig or a subspecies thereof (*Sus scrofa domestica*). Examples of *Sus scrofa domestica* breeds that can be used in the present invention include Landrace, Hampshire, Duroc, Chinese Meishan, Berkshire, Pietrain and Yorkshire. Examples of miniature pigs that can be used in the present invention include Ossabaw, Hanford, Sinclair, Libechov, Goettingen, Yucatan, Bama Xiang Zhu, Wuzhishan, and Xi Shuang Banna. In addition to porcines, additional ungulates that can be used in the invention include bovines, ovines, and caprines. Thus, for example, the invention can include the use of cows (e.g., *Bos taurus* or *Bos indicus*), sheep, goats, buffaloes, antelopes, oxen, horses, donkeys, mule, deer, elk, caribou, water buffalo, camels, llama, alpaca, and elephants.

As used herein, a "stop cassette" can be any sequence that terminates transcription and/or translation, including a promoter trap.

The invention provides several advantages over the state of the art, as it provides large, non-human animal models that can be used in the identification and characterization of therapies for genetic diseases, for example, the present invention describes the development of the first gene-targeted large animal model of human cancer, cancer development and progression.

As discussed above, mouse models of cancer have provided insight into understanding cancer biology, but are of limited use for the study of human cancer, cancer development and progression. A large animal model, such as the pig, holds the promise of a more accurate disease model given the similarities that pigs and humans share in terms of development, anatomy, and physiology. An improved model of human cancer, cancer development and progression would increase our understanding of cancer disease mechanisms and provide a more relevant setting in which to test new therapeutic interventions.

A porcine model offers several advantages over murine models. First, gene targeting provides an opportunity to introduce almost any desired mutation. This will allow for the targeting of "hotspot" regions that represent a broader range of patient-specific mutations. Second, somatic cell nuclear transfer (SCNT), sometimes referred to as cloning, offers the unique ability to produce genetically identical pigs, as well as genetically identical control animals (with the exception of the specific mutation of interest). This will reduce phenotypic variability and allow researchers to study specific mechanisms and treatments without concern of extraneous genetic factors. Conversely, the wide range of pig breeds also allows for genetic outcrossing as a means to identify and study modifier genes.

Availability of TP53-targeted, ATM-targeted, and KRAS-targeted large animal models, for example, will allow investigators to address key problems that have persisted unresolved for years. As a result, it will be possible to develop new treatments, medical devices, therapies, and preventions for cancer. Further, given the close physiological relationship between humans and large animals, such as pigs, there is an increased likelihood that results obtained using the animal models of the invention can be applied to humans, relative to other animal models. Specifically with respect to pigs, it is noted that pigs and humans have anatomical, histological, biochemical, and physiologic similarities.

Due to pigs' similarities to humans, a pig with human-like cancer will allow for the evaluation of drug toxicity, pharmacokinetics and efficacy in a single animal, something not possible in current models. This animal will also serve an unmet need in surgical training and medical imaging. Due to its size, reasonable cost and more consistent phenotype, this proposed model will allow refinement of surgical techniques using standard approaches, as well as minimally invasive and robotic technologies. In the context of medical imaging, noninvasive image-guided technologies including next generation MRI, ultrasound, nuclear imaging, x-ray and optical imaging techniques could be evaluated using instrumentation designed for humans. Importantly, these investigations would all be performed in a relevant, diseased setting.

In one example, a cancer-prone TP53-targeted or ATM-targeted porcine model would stimulate discovery, therapeutic applications, and the development of new devices and instruments, which have been slow to progress due to the lack of appropriate model systems. In another example, a large animal model (for example, a porcine model) in which the endogenous tumor suppressor p53 is mutated and the proto-oncogene KRAS allele can be activated in any tissue at any time would also improve the ability to understand human cancer, cancer development and progression. Importantly, the ability to activate KRAS temporally and spatially in a TP53 mutant background permits both childhood and adult cancer to be modeled in essentially any tissue, thereby allowing a large animal model (e.g., a pig) to model just about any human cancer. Like their KRAS/TP53-targeted murine counterparts, large animal models are expected to be highly susceptible to site-specific Cre-mediated tumorigenesis, resulting in accelerated tumor formation at the sites of interest. See, e.g., Jackson, E. L., et al., Genes Dev 2001, 15 (24), 3243-8; Caulin, C., et al., J Clin Invest 2007, 117 (7), 1893-901; Kirsch, D. G., et al., Nat Med 2007, 13 (8), 992-7; Tuveson, D. A., et al., Cancer Cell 2004, 5 (4), 375-87; White, A. C., et al., Proc Natl Acad Sci USA 2011, 108 (18), 7425-30.

The present invention also provides the use of inducible gene knock-in technology in a large animal model (e.g., pigs). As discussed further in the following Examples, a STOP cassette flanked by loxP sites will allow for the Cre-mediated activation of an endogenously expressed mutation in any tissue. See, e.g., Tuveson, D. A., et al., Cancer Cell 2004, 5 (4), 375-87; Lakso, M., et al., Proc Natl Acad Sci USA 1992, 89 (14), 6232-6. While this has obvious applications for induction of tissue-specific tumors in the current cancer model, successful implementation of the technology in large animals (e.g., pigs) will also lead to tissue- and temporal-specific gene manipulations for other disease models. Additionally, generating genetically identical mutant large animal models (e.g., KRAS/TP53 swine) will allow researchers to study specific mechanisms and treatments without concern of extraneous genetic modifiers.

The invention thus can be used to provide substantial benefits in the treatment of diseases and conditions caused by or associated with gene mutations, such as TP53, ATM and/or KRAS. Other features and advantages of the invention will be apparent from the drawings, the detailed description, the experimental examples, and the claims.

BRIEF DESCRIPTION OF THE DRAWINGS

This patent application file contains at least one drawing executed in color. Copies of this patent application publication with color drawing(s) will be provided by the Office upon request and payment of the necessary fee.

FIG. 3A shows a knockin targeting construct where R167H is represented by an asterisk. Porcine R167H corresponds to human R172H and murine R172H. FIG. 3B shows a knockout targeting construct where the termination codon is represented by the red "STOP". Exons 2-11 of porcine TP53 are depicted as black boxes. $Neo^R$ contains a neomycin phosphotransferase cDNA driven by the phosphoglycerate kinase (PGK) promoter and flanked by loxP sites. The rAAV inverted terminal repeats (ITRs) are in shown as white dotted boxes. Each homology arm is 1.2-1.4 kb in length.

FIG. 6A shows a representative 96-well gel containing 3 PCR-positive clone (boxed in white). The other wells represent $Neo^R$ clones resulting from random integration, or in the case of lighter bands, leftover DNA from dead cells. Each PCR-positive clone was re-electrophoresed on a conventional agarose gel to confirm proper size as seen in FIG. 6B. Expected sizes were 1.9 kb for targeted TP53 and 4.3 kb for an internal control sequence (wild-type LDLR). All lanes except 8 and 10 represent TP53-targeted cells.

FIG. 8A shows four 1-day old $TP53^{R167H/+}$ piglets. FIG. 8B shows a Southern blot of genomic DNA from TP53-targeted pigs. On the left, AflII/EcoNI digested genomic DNA was hybridized with a probe that detects porcine TP53 downstream of the targeting vector boundary. The TP53-targeted allele produced an approximately 6.0 kb band, and the wild-type band is approximately 4.3 kb. On the right, the same DNA was hybridized with a probe that detects the $Neo^R$ cassette, yielding only the targeted 7.8 kb band. Lanes 1-7 contain DNA from $TP53^{R167H/+}$ piglets. Lane 8 contains DNA from a wild-type pig. FIG. 8C presents DNA sequence chromatographs (SEQ ID NOS: 5 and 6, respectively, in order of appearance) showing the R167 codon from a wild-type pig and a TP53-targeted pig.

In FIG. 10A, exons 1 and 2 of porcine KRAS are depicted as gray boxes. The G12D mutation is shown with an asterisk. The stop cassette contains a transcriptional/translational stop domain and a promoterless neomycin resistance cassette ("STOP" arrow) and is flanked by loxP sites (white arrowheads). Small black arrows are the PCR screen primers described in FIG. 10B. Homologous recombination junctions are shown as vertical dashed lines. Genomic Southern blot restriction enzyme sites are indicated by H (HindIII) and B (Bsu36I). Figure is not to scale. FIG. 10B shows the results of the PCR screen and allele specific Southern blot. Lanes 1-11 represent a portion of the PCR-positive cell clones from the initial screen. Lane 12 is a G12D positive control. Lane 13 is a WT KRAS sequence. A G12D-specific, biotin-labeled oligonucleotide probe was used to determine which of the KRAS-targeted clones also contained the desired G12D mutation. Lanes 1, 2, 5, 7, 9, and 11 contain G12D.

FIG. 11A shows KRAS/TP53 piglets at 1 day of age. In FIG. 11B (Left), HindIII/Bsu36I digested genomic DNA was hybridized with a probe that detects porcine KRAS downstream of the targeting vector boundary. The KRAS-targeted allele produced a 5.0 kb band, and the wild-type band is approximately 7.4 kb. (Right) The same DNA was hybridized with a probe that detects the Neo$^R$ cassette, yielding only the targeted 7.4 kb band. FIG. 11C is a DNA sequence chromatogram targeted KRAS locus from KRAS/TP53 pig. G12D is shown as the underlined GAT codon. FIG. 11D shows a Cre-mediated induction of KRASG12D expression. RT-PCR KRAS mRNA was probed by a G12D-specific biotin-labeled oligonucleotide. Presence of absence of reverse transcriptase (RT) or Cre recombinase is noted.

FIG. 12A, 12B: Within the liver, focal atypia (arrows) was composed of irregular hepatic cords with enlarged hepatocellular cells and nuclei, 100 and 400×. Inset: A binucleate hepatocyte (arrow) with marginated chromatin and a prominent nucleolus was much larger than adjacent hepatocytes (FIG. 12B, lower left, inset).

FIG. 13A is a Coronal CT cross-sections illustrating the difference in lymph node short axis size: 26 mm in TP53$^{R167H/R167H}$ (m/m, Case 3) relative to 9 mm the TP53$^{+/+}$ (+/+, Case 7). Image data was acquired was acquired four months prior to necropsy at 27 weeks of age. FIGS. 13B and 13C show lymphadenopathy was a consistent finding on external examination (arrows, FIG. 13B, Case 3) and at necropsy (FIG. 13C, Case 6). FIG. 13D show lymph nodes were consistently effaced by sheets of neoplastic lymphocytes (asterisks, Case 3, 100×). FIG. 13E shows microscopically, the lymphomas had numerous mitotic figures (arrows) and frequent tingible body macrophages (arrowheads, 600×).

FIG. 14A shows splenomegaly was a consistent finding (bottom, Case 3). FIG. 14B shows spleens were effaced by neoplastic lymphocytes (asterisks, bottom panel, Case 3), 40×. In Case 2 (FIG. 14C), the spleen had ruptured with fibrinous exudate on the surface of the capsule (arrows). Microscopically, the ruptured spleen (Case 2) had necrotic foci (asterisks) and hemorrhage (red color, 20×) (FIG. 14D). The lung in Case 2 (FIG. 14E, 14F) had intravascular emboli composed of cellular and nuclear debris with neoplastic cells occluding numerous arteries (arrows, FIG. 14E, 400×) and capillaries in alveolar septa (arrows, FIG. 14F, 400×)—consistent with tumor lysis syndrome. Lymphoma pigs often had bridging infiltration by lymphoma cells (FIG. 14G, 14H) (asterisks) in portal regions of the liver (right panel, Case 4), 40×. FIG. 14I shows trends for liver and spleen volumes as segmented from CT, relative to animal weight for a cohort of TP53$^{R167H/+}$ pigs, showing the significantly elevated liver volume for lymphoma Case 4 (diamond) and slightly elevated spleen volume (square).

FIG. 16A: in-vivo imaging with computed tomography (CT) and magnetic resonance (MR) non-invasively identified a 28 mm cranial tumor shown in sagittal, coronal and axial views. CT data revealed the tumor had a mean density (137 HU) below that of bone, and had invaded the calvarium/skull. MR imaging with a 3D SPACE sequence demonstrated the heterogeneous content of the tumor and compression of brain tissue. FIG. 16B: The tumor (arrows, left panel) was external to but attached to the dura. FIGS. 16C, 16D: Removal of the tumor (FIG. 16C) revealed lysis and invasion of the tumor into the adjacent calvarium (arrows, FIG. 16D). FIG. 16E: The tumor was composed of spindle to round cells that produced irregular trabeculae of osteoid (arrows), 200×.

FIG. 17B, 17C) The extradural mass (arrows, FIG. 17B) expanded into the cranial vault (arrows, FIG. 17C) compressing the brain. FIG. 17D: The mass (asterisks) invaded into the frontal sinus cavity. FIG. 17E: The calvarial mass was composed of round to spindle cells that produced irregular trabeculae of osteoid (asterisks, 200×). FIG. 17F: The neoplastic cells had varying sized nuclei with a prominent nucleoli (arrows, 600×).

FIG. 18A shows an 18 mm lesion in the left distal femur with heterogeneous computed tomography (CT) density (Case 6). Time point 2 views show growth in the solid component of the lesion compared to time point 1. FIG. 18B: The tumor was composed of irregular trabeculae of osteoid and bone extending from the edge of the cortex (asterisks, 20×). FIG. 18C: The bony trabeculae were at times lined by loose mesenchymal to fibrous tissue and uncommon rims of osteoblasts, 400×.

FIG. 19A: A 13 mm lytic tumor was identified through non-contrast enhanced computed tomography in the left distal femur (Case 5) FIGS. 19B and 19C: The tumor (arrows, FIG. 19B, 40×) effaced bone marrow (note absence of trabeculae, right edge FIG. 19B) and was composed of sheets of pleomorphic round to spindle cells with scant osteoid deposition and multinucleate osteoclasts (arrows, FIG. 19C, 400×) were prominent within the tumor.

FIG. 20A: Proximal tibia tumor (arrows, 20×) was composed of coalescing bone trabeculae that effaced most of bone marrow to edges of cortex. Intertrabecular bone marrow had plump spindle cells (right, 400×) with 1-2 nucleoli. 20× and 400×. FIG. 20B: Sacrum tumor (arrows) was composed of large blood filled spaces that were partially surrounded by dense bone (asterisk, 20×) and in other areas by loose connective tissue (right, 200×) with cartilaginous/osteoid production. FIG. 20C: The tumor (arrows) was surrounded by a rim of hyperdense osteosclerosis (asterisks, middle, 20×) and composed of a low cellularity non-mineralized zone (black asterisk, right, 200×) that merged into a mineralized zone (white asterisk, right) and eventual sclerotic bone (top left of right image). FIG. 20D: Proximal tibial tumor was composed of focal increase of coalescing trabeculae (middle, 20×) of osteoid and lamellar bone sometimes with central cartilage-like cores (deep blue color, right, 400×) and lined by scattered loose connective tissue with uncommon osteoblasts.

FIGS. 21A and 21B: Volumetric reconstruction of the skeletal system and mesenteric lesion from computed tomography data at time point 1 (FIG. 21A) and time point 2 (FIG. 21B) showing change in the structure of the lesion over the 7 week time period between data points. FIG. 21C: The mesentery had locally extensive ossification (arrows, FIG. 21C). FIG. 21D-F: The bony tissue (FIG. 21D, 40×) ranged from plump spindle cells with progressive osteoid/mineralization (FIG. 21E, 400×) to mature bone with a thin with rim of fibrous tissue (FIG. 21F, 400×).

FIG. 22C: The renal tumor (arrow) was elevated from the cortex at the cranial pole of the right kidney. FIG. 22D: Cut surface of the tumor (T) showed a encapsulated (arrow) mass that was well-demarcated from normal kidney (K). FIG. 22E: The tumor (T) was composed of necrosis and hemorrhages (arrows pointing to patches) that were distinct from the unaffected kidney (K), 20×. FIG. 22F: The necrotic tumor tissue had irregular tubules separated by cords of connective tissue (asterisks, 100×). FIG. 22G: At the edges of the tumor, invading through the tumor capsule were small nests (See FIG. 13E, arrows) of poorly differentiated tubules with a high mitotic rate (arrows, G, 600×).

FIG. 23A: Western blots show increased expression of mutant p53-R167H protein and its transcriptional target cyclin B1, in lymph nodes (LN) and osteogenic tumor (Os) from p53 homozygote (m/m) pigs relative to low levels of each wild-type protein in the brain (Br) of normal p53+/+ pigs. GAPDH levels serve as the loading control. The case number for each specimen is indicated. FIG. 23B: Representative karyotypes from wild-type pig skin tissue (+/+, left panel) and from p53 mutant homozygote (m/m, right panels); lymph node tissue and an osteosarcoma from Case 5 showing abnormal chromosome number and structures in the malignant cells.

FIG. 24A: Schematic showing the known differential response of cells expressing wild-type p53 (+/+) and mutated (m) p53 alleles (+/m or m/m) to DNA damage. Adapted from Lane, 1992. FIG. 24B: Western blots of p53, p21 and GAPDH (loading control) levels in pig fibroblasts expressing wild-type p53 (+4), one mutant allele of R167H (+/m) or two R167H p53 alleles (m/m). Cells were treated with DMSO vehicle (−) or 400 ng/ml doxorubicin for 3 days (+Dxn). FIG. 24C: Representative histograms of cell cycle distributions for doxorubicin-treated cells from FIG. 24B. The percent of cells arrested in G1 phase (2N DNA content) is denoted in red, and cells undergoing apoptosis (<2N DNA content) highlighted in blue regions. FIG. 24D: Schematic showing that mutant KRAS induces cellular senescence in p53+/+ cells whereas cells expressing one or two mutant alleles of p53 escape KRAS-induced senescence and proliferate, during which time they sustain chromosomal alterations that foster cell transformation. FIGS. 24E and 24F: Pig fibroblasts of the indicated p53 genotype were infected with KRAS-G12V viruses, selected with puromycin for 3 days, and replated. FIG. 24E shows cell counts and FIG. 24F shows phase contrast microscopy. Cells expressing mutant p53 evade senescence and proliferate whereas those with wild-type p53 adopt the enlarged, flattened morphology of senescent cells.

DETAILED DESCRIPTION OF THE INVENTION

Figure 1:
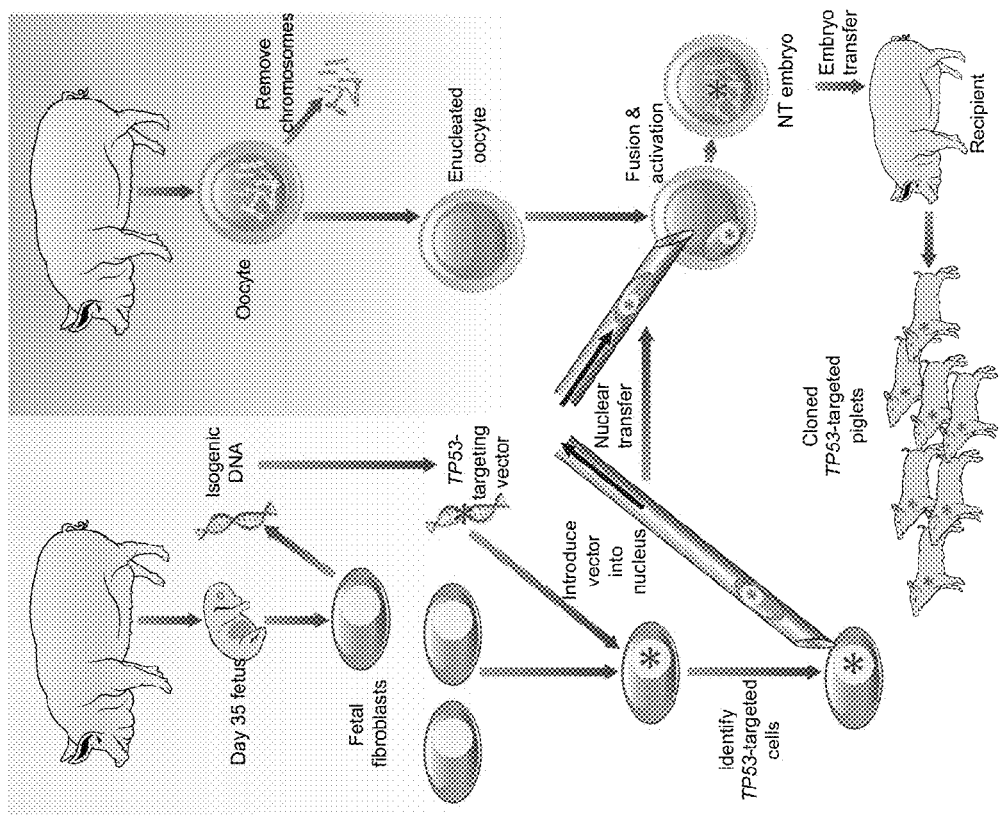
FIG. 1 is a schematic drawing showing one example of a method for generating TP53-targeted pigs. Fibroblasts are obtained from day 35 Yucatan fetuses. The targeting vector (with TP53 mutation indicated by asterisk) is introduced to fetal fibroblasts via AAV infection. Properly targeted cells are identified by PCR and Southern blot. Following nuclear transfer and fusion/activation, nuclear transfer embryos are transferred to recipient animals. After a 114 day gestation period, resulting piglets are TP53-targeted.

The invention provides animal models of human disease (e.g., cancer), which can be used in the identification and characterization of approaches for treating the diseases and conditions. As is discussed further below, the animal models of the invention are large, non-human animals, such as pigs, which have been genetically modified to include one or more mutations in a gene associated with a particular disease or condition, for example, the TP53 gene, the ATM gene and/or the KRAS gene. The genetic modifications can result in the animals having one or more symptoms characteristic of the disease or condition. Animals exhibiting such symptoms are particularly advantageous in the development of therapeutic approaches, as candidate drugs and other approaches to treatment can be evaluated for effects on the symptoms in such animals. Thus, in addition to the animal models themselves, the invention also provides methods of using the animals for identifying and characterizing treatments.

Further, the invention includes methods of making transgenic, large non-human animal models and cells that can be used in these methods. The animal models systems, methods, and cells of the invention are described further, below.

In one embodiment, the invention provides a heterozygous or homozygous knock-out non-human mammal (e.g., a pig). In one example, the invention provides a pig with its endogenous porcine TP53 gene knocked-out (i.e., a TP53+/− or TP53−/− pig). In another example, the invention provides a pig with its endogenous porcine ATM gene knocked-out (i.e., an ATM+/− or ATM−/− pig). In yet another example, the invention provides a pig with both its endogenous porcine ATM and TP53 genes knocked-out.

In another embodiment, the invention provides a heterozygous or homozygous knock-in non-human mammal (e.g., a pig). In one example, the invention provides a pig with its endogenous porcine TP53 gene modified by a knock-in mutation. In another example, the invention provides a pig with its endogenous porcine KRAS gene modified by a knock-in mutation. In yet another example, the invention provides a pig with both of its endogenous porcine TP53 and KRAS genes each modified by a knock-in mutation. In yet another example, the invention provides a pig with its endogenous porcine TP53 gene knocked out, and its endogenous KRAS gene modified by a knock-in mutation.

In addition to animals including knock-outs or mutations in endogenous genes, the invention also includes transgenic, large non-human animal models of human diseases and conditions (e.g., pigs), in which one or more endogenous genes associated with the diseases or conditions are knocked-out (i.e., genetically altered in such way as to inhibit the production or function of the products of these genes) and replaced with a comparable wild-type or mutated gene derived from a different animal (e.g., a human). In one example, a pig with its endogenous porcine TP53, ATM and/or KRAS gene knocked-out, expresses a mutant human TP53, ATM and/or KRAS transgene. Alternatively, the human transgene may encode a normal, wild-type copy of a gene of interest (e.g., TP53, ATM or KRAS). These embodiments of the invention are especially useful for the generation of non-human animal models of human diseases and conditions that can be used to test existing and potential therapeutics that may only (or may preferentially) modulate or treat the disease when contacting, or being in the presence of, human copies of the disease gene or protein in question.

The invention is described herein in reference to large animal models of cancer, which are generated by mutation, deletion or replacement of one or more of the TP53, ATM and KRAS genes. However, the methods of the invention are also applicable to the development of animal models of additional diseases and conditions.

The transgenic animals of the invention can be made using the following general strategy, which combines gene targeting and somatic cell nuclear transfer (SCNT), also known as cloning. Briefly, the genome of a cell (e.g., a fetal fibroblast) from an animal of interest, such as a pig, is genetically modified by, for example, gene targeting by homologous recombination, to create a "donor cell." According to the methods of the invention, the genetic modification results in at least partial inactivation of a gene associated with a particular disease or condition (e.g., a TP53 or ATM gene in cancer), as will be described in further detail below. The nucleus of such a genetically modified donor cell (or the entire donor cell, including the nucleus) is then transferred into a so-called "recipient cell," such as an enucleated oocyte. After activation and, typically, a brief period of in vitro culture, the resulting embryo is implanted into a surrogate female in which development of the embryo proceeds. This approach is illustrated with respect to pigs in FIG. 1. Typically, the donor cell, oocyte, and surrogate female are of the same species, but the sources can be different species, as is known in the art.

Figure 2:
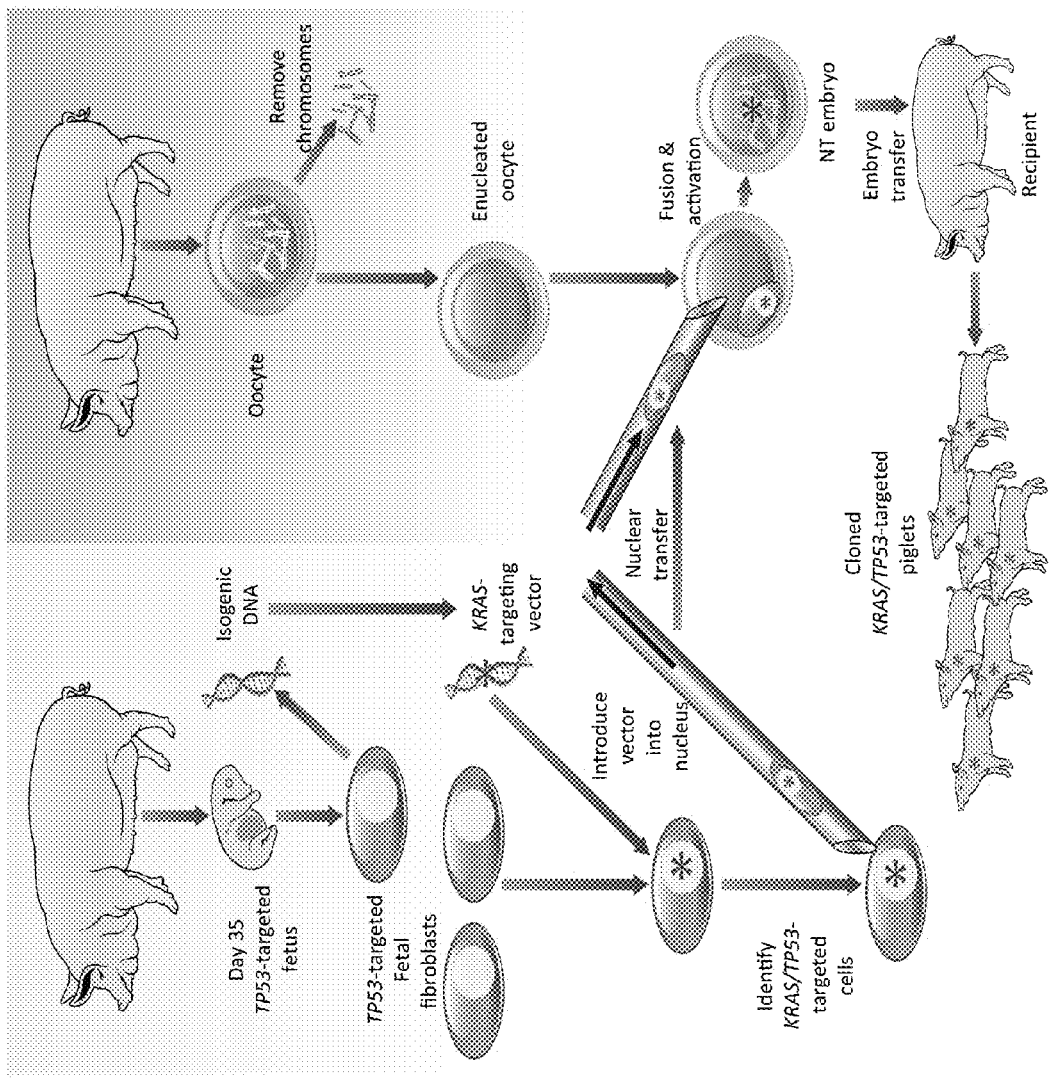
FIG. 2 is a schematic drawing showing one example of a method for generating KRAS/TP53-targeted pigs. Fibroblasts are obtained from day 35 TP53-targeted Yucatan fetuses. The targeting vector (with KRAS mutation indicated by asterisk) is introduced to fetal fibroblasts via AAV infection. Properly targeted cells are identified by PCR and Southern blot. Following nuclear transfer and fusion/activation, nuclear transfer embryos are transferred to recipient animals. After a 114 day gestation period, resulting piglets will contain mutated KRAS and TP53.

In this example, the genetic modification may also result in activation or overexpression of a gene associated with a particular disease or condition, or the expression of a mutated form of such a gene (e.g., a KRAS gene in cancer), as will be described in further detail below. This modification may be introduced alone or in connection with a second modification to another gene (for example, TP53). This approach is illustrated with respect to pigs in FIG. 2. While the genotype discussed in the Examples below is $KRAS^{G12D-LSL/+}/TP53^{R167H/+}$ (LSL stands for lox-Stop-lox, or a Stop cassette), these pigs are referred to herein as "KRAS/TP53-targeted" for simplicity and clarity. Further, while the Examples describe a conditional KRAS mutation inserted on the background of TP53-targeted pigs, the invention also includes large animal models with only the conditional KRAS mutation.

Similar procedures have been used to develop two different gene-targeted porcine models of cystic fibrosis, and a model of atherosclerosis. See, e.g., Rogers, C. S., et al. J Clin Invest 2008, 118 (4), 1571-7; Rogers, C. S., et al. Science 2008, 321 (5897), 1837-41; U.S. Pat. No. 7,989,675; U.S. patent application Ser. Nos. 13/288,720, 13/368,312 and 13/624,967. In studies for which genetic variability can be problematic, the ability to generate genetically identical large animals (for example, pigs), as well as control animals that are genetically identical except for the specific mutation, provides a resource that allows researchers to study specific mechanisms and treatments without concern of extraneous genetic factors.

Large animal models for cancer (for example, the TP53-targeted pig, the ATM-targeted pig, and the KRAS-targeted pig), will also provide a basis for research into aspects of cancer development and progression which are currently lacking in mouse models.

Details of methods for making large genetically modified animals according to the invention are provided below. Additional information concerning methods for making genetically modified pigs and other large animals is known in the art and can also be used in the present invention (see, e.g., U.S. Pat. No. 7,547,816; and WO 2005/104835; Prather et al., Reproductive Biology and Endocrinology 1:82, 1-6, 2003; Hao et al., Transgenic Res. 15:739-750, 2006; Li et al., Biology of Reproduction 75:226-230, 2006; Lai et al., Nature Biotechnology 24(4):435-436, 2006; Lai et al., Methods in Molecular Biology 254(2):149-163, 2004; Lai et al., Cloning and Stem Cells 5(4):233-241, 2003; Park et al., Animal Biotechnology 12(2):173-181, 2001; Lai et al., Science 295:1089-1092, 2002; Park et al., Biology of Reproduction 65:1681-1685, 2001).

The transgenic animals of the invention can be any transgenic, large non-human animal. In one embodiment of the present invention, the transgenic animal is a swine or pig. Pigs share many similarities with humans including anatomy, biochemistry, physiology, size (particularly miniature pig breeds), lifespan, and genetics. The pig has proven to be an excellent model for obesity, diabetes, alcoholism, hypertension, skin physiology, intestinal function, nutrition, and injury (see, e.g., Rogers, C. S., et al. Am J Physiol Lung Cell Mol Physiol 2008, 295 (2), L240-63). Recently, two porcine models of cystic fibrosis were developed that demonstrate all of the clinical manifestations of the human disease, including meconium ileus, pancreatic insufficiency, and lung disease. See, e.g., Rogers, C. S., et al. Science 2008, 321 (5897), 1837-41; Meyerholz, D. K., et al. Am J Respir Crit Care Med 2010, 182 (10), 1251-61; Stoltz, D. A., et al. Sci Transl Med 2010, 2 (29), 29ra31; and Meyerholz, D. K., et al. Am J Pathol 2010, 176 (3), 1377-89. In addition, similarity of porcine and human organs has led to a large effort to develop them as a source of organs for xenotransplantation (see, e.g., Cooper, D. K., et al. Annu Rev Med 2002, 53, 133-47). Furthermore, the reproductive characteristics of swine are favorable for their use as a model (See Table 1). Their relatively fast maturation rate and the large number of offspring generated from a single sow in one year allow a colony to rapidly expand.

TABLE 1

Reproductive characteristics of several species (values are approximate).

| Species | Gestation time | Sexual maturity | Offspring per delivery | Deliveries per year | Offspring per year |
|---|---|---|---|---|---|
| Mouse | 20-22 d | 40-60 d | ~6 | ~17 | 100 |
| NH primate | 150-175 d | 4-5 yr | 1 | 2 | 1-2 |
| Minipig | 114 d | 5-6 mo | 4-7 | ~3 | 12-21 |

Cancer has not been widely studied in pigs, primarily because the vast majority of pigs are used for commercial pork production, where the average lifespan is 6-8 months, and any pigs displaying poor health are culled from the herd. However, there is a significant body of literature describing porcine cancers that are remarkably similar to humans in terms of frequency, tumor biology, diversity, and genetics. Like humans, cancer in pigs is rare, and when it does develop, tumors appear to be of epithelial cell origin, which is in stark contrast to the mesodermal origin predominant in mice. See Adam, S. J., et al., *Oncogene* 2007, 26 (7), 1038-45; Harmon, B. G., et al., *J Vet Diagn Invest* 2004, 16 (6), 587-9; Kleinschmidt, S., et al., *Vet Pathol* 2006, 43 (4), 569-73. Spontaneous tumors have been seen in the mouth, kidney, liver, GI tract, skin, and endometrium, with many of these metastasizing to lymph nodes, lungs and other organs. See Pathak, S., et al., *Int J Oncol* 2000, 17 (6), 1219-24; Harmon, B. G., et al., *J Vet Diagn Invest* 2004, 16 (6), 587-9; Kleinschmidt, S., et al., *Vet Pathol* 2006, 43 (4), 569-73; Grieco, V., et al., *J Comp Pathol* 2006, 134 (2-3), 143-51; Fisher, L. F., et al., *J Comp Pathol* 1978, 88 (4), 505-17; Sandison, A. T., et al., *Cancer* 1968, 21 (4), 727-42; Madewell, B. R., Yale *J Biol Med* 1981, 54 (2), 111-25. Induced porcine models are being attempted in numerous tissues including liver, pancreas, skin, and esophagus. See Li, X., et al., *Cardiovasc Intervent Radiol* 2006, 29 (3), 420-8; Vinter-Jensen, L., et al., *Gastroenterology* 1997, 113 (4), 1367-74; Monteiro-Riviere, N., et al., *Cutan Ocul Toxicol* 2006, 25 (2), 103-19; Azzi, C., et al., *Carcinogenesis* 2006, 27 (1), 137-45.

Genetic induction of tumorigenesis in porcine cells using genes known to cause cancer in humans has produced xenograft cancer models in pigs. See Adam, S. J., et al., *Oncogene* 2007, 26 (7), 1038-45; Cho, P. S., et al., *Blood* 2007, 110 (12), 3996-4004. Though these pigs have limited utility due to expensive immunosuppressant regimens, this study demonstrated that pig cells are similar to human cells in their resistance to transformation, suggesting a common tumorigenesis process. For example, porcine p53 response to DNA damaging agents has been studied in pig cells, and both UV radiation and chemical carcinogens stabilize the protein just as in humans. See Qiu, Y., et al., *Biochem Biophys Res Commun* 2008, 377 (1), 151-5.

The porcine genome project was recently completed. The reference breed for the initial genome data was the domestic Duroc pig. The sequence of the TP53 locus was determined from the miniature pig breed (Yucatan). Like human TP53, the Yucatan pig ortholog has 11 exons and a highly conserved gene structure. Porcine p53 is 81% identical to human p53 (92% identical within the DNA-binding domain), with most of the differences found in the nonconserved and intrinsically disordered proline-rich region. See Joerger, A. C., et al., *Cold Spring Harb Perspect Biol* 2010, 2 (6), a000919. Also, all of the "hotspot" mutation (and potentially druggable) sites are conserved.

Similarly, KRAS sequence and function is highly conserved across species (99% amino acid sequence identity). Thus, the porcine $KRAS^{G12D}$ mutation described in the Examples is believed to behave in a manner similar to the human ortholog. Further supporting this assumption, the orthologous mutation in mice recreates the constitutive activation seen in the human protein. See, e.g., Schubbert, S., et al., Nat Rev Cancer 2007, 7 (4), 295-308; Ellis, C. A., et al., Cell Signal 2000, 12 (7), 425-34.

The invention includes animals in which only one allele of a targeted gene (e.g., TP53, ATM or KRAS) is disrupted or mutated, with the other allele remaining unaffected. These animals, which are referred to herein as "heterozygous" or "hemizygous" animals, can be used, for example, as models to study the development or progression of a disease (for example, cancer) in heterozygous animals. Further, these animals can be used in breeding approaches to generate homozygous mutants, if desired, for example, in the case of diseases caused or exasperated by homozygous recessive mutations.

The heterozygous animals of the present invention can also be used as animal models themselves, for example, in the case of diseases caused by autosomal dominant mutations, or where disruption of one allele of the targeted gene may result in some phenotypic expression of the mutation that is less severe than disruption of both alleles.

Also included in the invention are homozygous mutant animals, in which both alleles of a target gene (e.g., TP53, ATM or KRAS) are disrupted or mutated, by the same or different mutations. In addition to being obtainable by breeding approaches involving hemizygous animals, homozygous mutant animals can also be obtained using an approach in which a cell (e.g., a fetal fibroblast) including a mutation in one allele, such as a cell obtained from an animal produced using the method summarized above, is subjected to gene targeting by homologous recombination to achieve modification of the remaining allele. The resulting donor cell can then be used as a source of a modified nucleus for nuclear transfer into a recipient cell, such as an enucleated oocyte, leading to the formation of a homozygous mutant embryo which, when implanted into a surrogate female, develops into a homozygous mutant animal.

A target gene (e.g., a TP53, ATM or KRAS gene) can be subject to genetic modification in any appropriate cell type of a species for which it is desired to create an animal model of a disease associated with mutation of the gene, according to the invention. As is understood in the art, it is necessary to be able to culture and carry out homologous recombination in a cell that is to be used as a donor cell. A particular example of such a cell, which is described in more detail below in connection with pigs, in the experimental examples, is the fetal fibroblast. These cells can be obtained using, for example, the approach described in U.S. Pat. No. 7,547,816 and other references cited herein.

The invention also includes the use of other cell types that may be present in the cell preparations obtained using the method described in U.S. Pat. No. 7,547,816. Additional examples of cells that can be used as donor cells in making the transgenic animals of the invention include other fetal cells, placental cells, or adult cells. Specific examples of such cells for gene targeting include differentiated cells such as fibroblasts, epithelial cells, neural cells, epidermal cells, keratinocytes, hematopoietic cells, melanocytes, chondrocytes, B-lymphocytes, T-lymphocytes, erythrocytes, macrophages, monocytes, placental, and muscle cells.

If a cell to be genetically altered is derived from an embryo or a fetus, the cell (e.g., a fetal cell or placental cell) can be isolated at any time during the gestation period until the birth of the animal, which may or may not be itself genetically altered. In the case of a pig, such cells can be obtained, for example, between 20 to 90 days of gestation, between 25 to 60 days of gestation, between 30 to 45 days of gestation, or between 35 to 40 (e.g., at 35 days) of gestation. The time periods for obtaining cells from other animals is known in the art (see, e.g., U.S. Pat. Nos. 7,420,099 and 7,928,285).

Gene targeting carried out to make the cells and animals of the invention can result in gene inactivation by disruption, removal, modification, or replacement of target gene sequences. For example, inactivation can take place by the insertion of a heterologous sequence and/or a stop codon into a target gene. Gene targeting can also result in a point mutation, e.g., a missense mutation, as is described in the Examples below. Further, gene targeting can also result in gene activation, for example, by the insertion of an "activating" mutation or a GOF mutation, as is also described in the Examples below.

As is known in the art, inserted sequences can replace previously existing sequences in a gene or can be added to such sequences, depending on the design of the targeting construct. In another example, deletion of a sequence using homologous recombination results in a frameshift mutation that yields a prematurely truncated and non-functional protein. Also as is known in the art, the design of targeting constructs can be altered, depending upon whether it is desired to completely knock out the function of a gene, maintain some level of reduced function, or introduce a gain of function, e.g., by inducing expression of a mutated gene product or by inducing expression of a gene that would otherwise not be expressed. Such changes may be achieved by, for example, replacement with sequences that are identical to wild-type sequences, except for the presence of specific mutations giving rise to features of the target disease. In other approaches, coding sequences are not altered or are minimally altered and, rather, sequences impacting expression of a target gene, such as promoter sequences, are targeted. In any case, selectable marker insertion is often desirable to facilitate identification of cells in which targeting has occurred. If desired, such markers or other inserted sequences can later be removed by, e.g., cre-lox or similar systems.

A "humanized" cancer model (for example, a TP53−/− animal expressing a mutant human TP53 transgene) can be made numerous ways, including, but not limited to: i) introducing a mutant human TP53 cDNA, partial mutant human TP53 gene, or entire human TP53 gene carrying a mutation into animal (e.g., porcine) TP53−/− cells, selecting for mutant human TP53 gene insertion, and using these cells as nuclear donors in somatic cell nuclear transfer, and ii) introducing a mutant human TP53 cDNA, partial mutant human TP53 gene, or entire human TP53 gene carrying a mutation to animal TP53−/− cells into matured oocytes, fertilizing, then transferring to a recipient female. Additionally, this example can apply to any of several genes related to cancer development and progression in humans, for example, ATM and KRAS.

As is known in the art, targeted gene modification requires the use of nucleic acid molecule constructs having regions of homology with a targeted gene (or flanking regions), such that integration of the construct into the genome alters expression of the gene, either by changing the sequence of the gene and/or the levels of expression of the gene. Thus, to alter a gene, a targeting construct is generally designed to contain three main regions: (i) a first region that is homologous to the locus to be targeted (e.g., the TP53, ATM or KRAS genes or a flanking sequence), (ii) a second region that is a heterologous polynucleotide sequence (e.g., encoding a selectable marker, such as an antibiotic resistance protein) that is to specifically replace a portion of the targeted locus or is inserted into the targeted locus, and (iii) a third region that, like the first region, is homologous to the targeted locus, but typically is not contiguous with the first region of the genome. Homologous recombination between the targeting construct and the targeted wild-type locus results in deletion of any locus sequences between the two regions of homology represented in the targeting vector and replacement of that sequence with, or insertion into that sequence of, a heterologous sequence that, for example, encodes a selectable marker. Use of such promoters may not be required in cases in which transcriptionally active genes are targeted, if the design of the construct results in the marker being transcribed as directed by an endogenous promoter. Exemplary constructs and vectors for carrying out such targeted modification are described herein. However, other vectors that can be used in such approaches are known in the art and can readily be adapted for use in the invention.

In order to facilitate homologous recombination, the first and third regions of the targeting vectors (see above) include sequences that exhibit substantial identity to the genes to be targeted (or flanking regions). By "substantially identical" is meant having a sequence that is at least 80%, preferably at least 85%, preferably at least 90%, more preferably at least 95%, even more preferably at least 98%, and even more preferably 100% identical to that of another sequence. Sequence identity is typically measured using BLAST® (Basic Local Alignment Search Tool) or BLAST® 2 with the default parameters specified therein (see, Altschul et al., J. Mol. Biol. 215: 403-410, 1990; Tatiana et al., FEMS Microbiol. Lett. 174: 247-250, 1999). These software programs match similar sequences by assigning degrees of homology to various substitutions, deletions, and other modifications. Thus, sequences having at least 80%, preferably at least 85%, preferably at least 90%, more preferably at least 95%, even more preferably at least 98%, and even more preferably 100% sequence identity with the targeted gene loci can be used in the invention to facilitate homologous recombination.

The total size of the two regions of homology (i.e., the first and third regions noted above) can be, for example, approximately between 1-25 kilobases (for example, approximately between 2-20 kilobases, approximately between 5-15 kilobases, or approximately between 6-10 kilobases), and the size of the second region that replaces a portion of the targeted locus can be, for example, approximately between 0.5-5 kilobases (for example, approximately between 1-4 kilobases, approximately between 1-3 kilobases, approximately between 1-2 kilobaeses, or approximately between 3-4 kilobases).

The targeting constructs can be included within any appropriate vectors, such as plasmid or viral vectors (e.g., adenovirus or rAVV vectors), which can be introduced into cells using standard methods including, for example, viral transduction, electroporation, or microinjection.

Recombinant adeno-associated virus has been used to deliver gene targeting vectors to cell lines and primary cells (see, e.g., Russell, D. W., et al. Nat Genet 1998, 18 (4), 325-30). For example, rAAV has been used to introduce two different targeted modifications to the porcine CFTR gene. See, e.g., Rogers, C. S., et al. J Clin Invest 2008, 118 (4), 1571-7, U.S. Pat. No. 7,989,675 and U.S. patent application Ser. No. 12/283,980.

The use of a rAAV to deliver the targeting construct offers many benefits. First, rAAV1 (and other rAAV serotypes) infects pig fetal fibroblasts with nearly 100% efficiency. See, e.g., Rogers, C. S., et al. J Clin Invest 2008, 118 (4), 1571-7. Second, rAAV infection of pig fetal fibroblasts results in little or no cell toxicity. Third, rAAV infection results in the delivery of a single-stranded gene-targeting construct directly to the nucleus, the amount of DNA per cell is small, and it can infect many cell types. Importantly, the ratio of homologous recombination events to random integrations is more favorable than that seen with electroporation of lipid-mediated transfection. See, e.g., Vasquez, K. M., et al. Proc Natl Acad Sci USA 2001, 98 (15), 8403-10.

The methods of the invention, employing rAAV vectors, resulted in high levels of gene targeting efficiency in these somatic cells, as compared to prior methods. Central to the methods of the invention is the fact that the entire procedure was performed in a time-sensitive manner, because excessive cell culture time (for example, more than 30 days) negatively impacts nuclear transfer efficiency (Lai et al., Cloning and Stem Cells 5(4):233-241, 2003). Following fibroblast harvest from day 35 fetuses, the cells were frozen within 48 hours. The use of an AAV vector to deliver the gene targeting construct allowed targeting to begin 24 hours after thawing cells and required no cell detachment and re-attachment, which is required in other methods. Multiple cell detachment and re-attachment events (trypsinization) are thought to decrease the ability of a cell to serve as a nuclear donor in nuclear transfer. Further, G418 selection in 48 96-well plates prevents the need for the more conventional, time-consuming isolation of resistant clones with cloning rings. The screen for gene targeted clones was designed such that all positive clones could be identified and frozen within a 3-5 day period. All clones were frozen by day 18, therefore the cells have been in culture approximately 20 days since being harvested from the fetus. In this aspect of the invention, reduction of the time in culture increases the likelihood that cells used as nuclear donors are viable, normal, and euploid.

Accordingly, the invention provides a method of gene-targeting cells, such as pig cells (e.g. pig fetal fibroblasts), in which the number of days in culture (during which targeting and selection takes place) is preferably less than 30 days, preferably 25-29 days, preferably 20-24 days, and more preferably 19, 18, 17, 16, 15, or fewer days. To facilitate this method, the selection can take place in multi-well plates, as described further below. Further, the cells may be frozen shortly after harvest (for example, within 24, 48 or 96 hours). After cell thawing (or after harvest, if the cells are not previously frozen), gene targeting with a rAAV vector can be carried out within, for example, 12, 24, 36 or 48 hours, without the use of multiple detachment/re-attachment events, and selection can proceed in an expedited manner, such as by use of multi-well plates (e.g., 96 well plates), prior to freezing.

Other types of vectors, or more specifically other types of targeting construct delivery methods, are also available to those of skill in the art and may be used in the present invention. Such methods include cell transfection methods, including calcium phosphate, lipofection, electroporation, and nuclear injection, all of which can be used to deliver the targeting construct. If the gene is transcriptionally active in the cell being used, then a promoterless selectable strategy can be employed, so that antibiotic resistance will only be found in cells that have had a recombination event within the transcribed unit.

Genetically targeted cells are typically identified using a selectable marker, such as neomycin. If a cell already contains a selectable marker, however, a new targeting construct containing a different selectable marker can be used. Alternatively, if the same selectable marker is employed, cells can be selected in the second targeting round by raising the drug concentration (for example, by doubling the drug concentration), as is known in the art. As is noted above, targeting constructs can include selectable markers flanked by sites facilitating excision of the marker sequences. In one example, constructs can include loxP sites to facilitate the efficient deletion of the marker using the cre/lox system. Use of such systems is well known in the art, and a specific example of use of this system is provided below, in the experimental examples.

Upon obtaining cells in which a target gene (e.g., a TP53, ATM or KRAS gene) has been targeted (one or both alleles, as described above), nuclear transfer can be carried out. Optionally, the genetically modified nuclear donor cells can be frozen prior to nuclear transfer. Recipient cells that can be used in the invention are typically oocytes, fertilized zygotes, or two-cell embryos, all of which may or may not have been enucleated. Typically, the donor and the recipient cells are derived from the same species. However, it is possible to obtain development from embryos reconstructed using donor and recipient cells from different species.

Recipient oocytes can be obtained using methods that are known in the art or can be purchased from commercial sources. As is known in the art, the donor nucleus or the donor cell itself can be injected into the recipient cell or injected into the perivitelline space, adjacent to the oocyte membrane. The nuclear transfer complex formed in this manner can be activated by standard methods, which may involve electrical fusion/activation or electrical fusion/chemical activation, as is described further below. Further processing of the nuclear transfer complex, including implementation of the complexes into surrogate mothers, is described further below.

The transgenic animals of the invention can be used in the identification and characterization of drug and other treatment methods for the disease or condition associated with mutation of the gene targeted according to the invention. In these methods, for example, a candidate therapeutic agent can be administered to an animal and the impact of the agent on a feature of the disease exhibited by the animal can be monitored. Optionally, the methods can also involve exposure of the animals to environmental or other conditions known to contribute to or exacerbate the disease or condition. For example, in cases of cancer, animal models having impaired function in a gene associated with the development or progression of cancer can be used to monitor the effect of a therapeutic agent, such as a drug, on the treatment or management of cancer. In another example, gene- and cell-based therapies for cancer can be administered in such an animal and the animal may be monitored for the effects on the development or progression of cancer, and further can be used to assess the effect and the impact on progression (or reversal) of cancer.

With the porcine model of the invention, it is possible to test hypotheses that lead to new treatments, diagnostics, protocols, imaging technologies and medical devices, and to evaluate potential therapies for cancer. Likely activities involving the present invention may include evaluating current and future therapeutics for toxicity, pharmacokinetics and efficacy within the same animal. Medical devices makers may study the efficacy of products in a relevant, diseased setting. And in the context of medical instruments, noninvasive ultrasound imaging may be evaluated to diagnose and chart the development and progression of cancer.

Availability of large animal models for cancer allows new investigations and tests of therapeutics. The screening methods of the invention can be carried out to test the efficacy of new compounds, combinations of new and old compounds, diagnostics, non-pharmaceutical treatments (such as gene- and cell-based therapies), medical devices, and combinations of the foregoing.

Advantages of a Porcine Cancer Model

In one embodiment of the invention, the large animal models are porcine or swine. Specific attributes of the porcine model offer new research opportunities that are not feasible in the current cancer models, for example, size and lifespan. A mutant TP53 model in the Yucatan miniature pig, for example, presents a breed that reaches a full-grown weight of 60-75 kg at 2 years of age—similar to that of an adult human. This makes it better suited than small animal models for studies involving the optimization and validation of imaging technologies and surgical procedures. It is important to note that a model can also be too large. For example, domestic pig breeds, such as those being used in other cancer models are 2-3 times bigger. See, e.g., Basel, M. T., et al., BioResearch open access 1:63-68 (2012); Flisikowska, T., et al., Gastroenterology 143:1173-1175 e1171-1177 (2012); Leuchs, S., et al., PloS one 7:e43323 (2012). This would exclude domestic pigs from most longitudinal monitoring/treatment studies with clinical imaging technologies, as they would quickly outgrow the size capacity of a typical clinical imaging scanner with a bore diameter of 60-70 cm. Also related to size, tissues from Yucatan miniature pigs are available in sufficient quantities to develop porcine tissue repositories containing cancer and matched normal tissues for future studies. Likewise, the larger circulatory volume of Yucatan miniature pigs compared to mice permits more repeated sampling of peripheral blood for potential biomarkers of cancer, enabling a broader spectrum of disease parameters to be monitored over time. Finally, the lifespan of pigs (10-15 years) is quite long compared to other animal models facilitating investigations of the natural history of various cancers, long-term treatment effects, and successive surgical interventions.

A large animal cancer model presents opportunities to improve clinical cancer outcomes in humans by serving as a controlled surrogate for human cancer patients. In so doing, research studies may be designed with a small target population of animals, studied extensively, and with unrestricted access to validating tissue samples. Thus, large amounts of data, with tightly controlled co-factors and low population variation may be achieved, requiring fewer subject numbers for equivalent statistical significance than a human cancer cohort. Furthermore, many cancer types are heterogeneous in content, composed not only of cancerous cells but also inflammatory mediators (see, e.g., Coussens, L. M., et al., Nature 420:860-867 (2002)), fibrotic stroma (see, e.g., Kalluri, R. et al., Cancer 6:392-401 (2006)), necrotic tissue and complex vasculature (see, e.g., Sieren, J. C., et al., Annals of biomedical engineering 38:3581-3591 (2010). This porcine model does not rely on an immuno-compromised host for tumor development, unlike xenograft models (see, e.g., Basel, M. T., et al., BioResearch open access 1:63-68 (2012)). A mutant TP53 pig, for example, opens new lines of investigation to explore the interplay between a functional immune response and the tumor microenvironment as it relates to tumor progression, diagnosis, treatment and monitoring (see, e.g., Shiao, S. L., et al., Genes & Development 25:2559-2572 (2011)).

The porcine cancer model provides new opportunities to improve cancer detection, monitoring, and treatment approaches in ways not possible with murine models or human patients. Medical imaging technologies (CT, MRI, and PET) play a key role in the clinical management of cancer patients in facilitating cancer detection, staging, and treatment response monitoring. However, the advanced capabilities of these systems are in many cases underutilized clinically due to significant challenges in protocol optimization and validation within the cancer patient population. See, e.g., Frangioni, J. V. Journal of clinical oncology: official journal of the American Society of Clinical Oncology 26:4012-4021 (2008). A large animal cancer model allows for the collection of many imaging datasets with varying protocols and/or modalities in the same cancerous tumor. Thus, resulting image data features can be directly compared and optimal protocols/modalities may be identified. This capability would be highly useful in the optimization of radiation dose, contrast delivery rate, and scan delay timing for dynamic dual energy CT. See, e.g., Simons, D. et al., European radiology (2014). The comparison of alternate PET radiotracers, along with improved acquisition strategies to optimize PET resolution, would also benefit from a human sized cancer model. See, e.g., Sharma, R. et al., British journal of pharmacology 163:1565-1585 (2011); Shiga, T. et al., Journal of nuclear medicine: official publication, Society of Nuclear Medicine 50:148-155 (2009).

While micro-imaging technology exists for CT, PET, and MRI data acquisition in murine cancer models, these systems do not contain the same capabilities of the equivalent clinical systems. See, e.g., Ritman, E. L., Annual review of biomedical engineering 13:531-552 (2011); Weissleder, R., Nature reviews. Cancer 2:11-18 (2002). These differences in acquisition technology combined with large differences in subject size, as well as heart, respiratory, and metabolic rates make rodents ineffective models for translatable protocol development. In a human cancer cohort for research, there is often a high degree of variability in cancer type and stage, clinical treatment approach, subject co-morbidities, and access to endpoint data (mortality, comprehensive histopathology, etc.). There are also restrictions that limit the ability for multiple data point acquisition, such as minimizing exposure to medical ionizing radiation, study time limitations, and a primary concern for the patient's clinical treatment and survival. The porcine model overcomes these constraints.

Another important capability provided by the porcine cancer model is to utilize medical imaging technology to monitor cancer development over time, with or without intervention. Studying cancer progression in the absence of treatment is not possible in humans. In this porcine model, data may be collected prior to tumor development, during tumor growth, and through to metastatic disease. This will provide insight into cancer pathogenesis and the ability of current medical imaging technologies to capture and classify the changing states of cancer progression. Medical imaging is key in planning clinical interventions. The similar anatomy and physiology to humans makes this porcine model ideal to test image guided, minimally invasive surgical techniques as well intensity modulated radiation therapy strategies (see, e.g., Bowen, S. R. et al., *Clinical and translational medicine* 1:18 (2012). Comprehensive post intervention evaluation in the porcine model is also feasible, utilizing multimodality imaging and tissue resection to determine if effective destruction of all cancer cells was achieved, if early indicators of metastatic disease can be found in other target organs, and/or if toxicity occurred in non-diseased tissue.

TP53 and Cancer

TP53 mutations, which occur in the majority of sporadic human cancers and some inherited cancer-prone disorders, compromise protective checkpoints in cells that normally ensure genomic integrity, thereby facilitating cellular transformation and tumorigenesis. See, e.g., Levine, A. J. et al., *Nature Reviews Cancer* 9:749-758 (2009); Freed-Pastor, W. a. et al., *Genes & Development* 26:1268-1286(2012).

In the swine created as described in Example 5 below, all $TP53^{R167H/R167H}$ pigs that reached maturity developed some type of cancer including lymphoma, Wilms tumor (nephroblastoma), and osteogenic tumors (osteosarcoma). Each tumor type is associated with mutations of TP53 and/or its pathway(s) in humans and is found in Li-Fraumeni patients The osteogenic tumors seen in $TP53^{R167H/R167H}$ pigs may be of particular clinical interest and relevance. While Li-Fraumeni patients develop this type of tumor (see Birch, J. M. et al., *Cancer research* 54:1298-1304 (1994); Porter, D. E. et al., *The Journal of bone and joint surgery. British volume* 74:883-886 (1992)) most osteosarcomas seen in people actually arise sporadically and are associated with somatic TP53 mutations (see Miller, C. W. et al., *Cancer research* 50:7950-7954 (1990)) which correlates with greatly reduced event-free survival. See, e.g., Tsuchiya, T. et al., *Cancer genetics and cytogenetics* 120:91-98 (2000); Wunder, J. S. et al., *Journal of clinical oncology: official journal of the American Society of Clinical Oncology* 23:1483-1490 (2005). Importantly, while the clinical aspects of osteosarcoma are well defined (Table 2) (see Luetke, A., et al., *Cancer treatment reviews* (2013)), the early pathogenesis of this malignancy is not well understood. A study of benign to malignant osteogenic tumors suggests that tumor progression is associated with an increased frequency of genetic alterations. See Radig, K., et al., Pathology, research and practice 194:669-677 (1998). Chromosome clonality (see Dal Cin, P., et al., *British journal of cancer* 78:344-348 (1998)) and TP53 alterations (see Oliveira, C. R., et al., *Clinics* 62:167-174 (2007)) have been described in benign osteogenic tumors and subsequent osteosarcoma arising from a benign osteogenic tumor has been reported (See Unni, K. Philadelphia: Lippencout-Raven (1996)).

TABLE 2

Expected morphology and site of origin for selected bone tumors and tumor-like conditions in humans.

| Type | Morphology | Site(s) of origin |
|---|---|---|
| Osteosarcoma | Mesenchymal cells producing osteoid/bone often subdivided into osteoblastic, chondroblastic and fibroblastic subtypes | Metaphysis of long bones (esp. distal femur and proximal tibia and humerus); skull, jaw and pelvis |
| Osteoid osteoma | Immature bone with increased vascularity and nerves; often with a rim of sclerotic bone | Long bones especially of lower extremity (e.g. femur); also reported in foot and spine; preference for diaphysis/metaphysis regions of long bones often near cortex |
| Giant cell tumor of bone | Sheets of mononuclear osteoblastic cells admixed with numerous, prominent multinucleate cells (osteoclasts) | Most common in epiphysis/metaphysis of long bones (e.g. distal femur, proximal tibia, and distal radius) and also in sacrum/spine; rare in hands, feet, patella, talus |
| Aneurysmal bone cyst (ABC) | Lakes of bloods (not lined by endothelial cells) associated with proliferating fibroblasts, osteoclasts and reactive bone | Most common in long bones (~73%), also reported in pelvis, spine, foot, scapula, sacrum and ribs. 20% (2/10 cases) of ABCs in sacrum were associated with tumors |
| Heterotopic mesenteric ossification/ myositis ossificans | Sclerosing mesenteritis with fat necrosis and eventual bone/osteoid formation | Bone formation in mesentery and/or serosa often as a 54equel to traumatic injury or hemorrhage | expressing the mutant form of p53 (R175H) modeled in the $TP53^{R167H/R167H}$ pigs of the present invention (see Birch, J. M. et al., *Cancer research* 54:1298-1304 (1994); Kleihues, P. et al., *The American journal of pathology* 150:1-13 (1997); Porter, D. E. et al., *The Journal of bone and joint surgery. British volume* 74:883-886 (1992)). The complete tumor penetrance obtained in $TP53^{R167H/R167H}$ pigs, and corresponding lack of tumor development in wild-type control animals, indicates that the cancers arising in these pigs are due to TP53 gene targeting and not spontaneous tumorigenesis, which occurs at exceedingly low incidences for the tumor types observed (between 2-20 per 100,000). See, e.g., Jacobs, R., Messick, J. et al., Ames, Iowa: Iowa State Press. 159-160 (2002); Migaki, G. et al., *Journal of the American Veterinary Medical Association* 159:441-442 (1971).

The $TP53^{R167H/R167H}$ pigs of the present invention had a wide spectrum of osteogenic tumors ranging from osteosarcoma of the calvaria to various low-grade/benign tumors (e.g. giant cell tumor of bone) of long bones. See Table 3 below. There is no evidence that the multiple osteogenic tumors observed within a single animal are a result of metastasis. The ability to conduct broader interspecies comparisons in humans, mice, and swine, should strengthen the probability of identifying common and potentially causative molecular events required for malignant conversion to osteosarcoma (see Walkley, C. R., et al., *Genes & Development* 22:1662-1676 (2008)).

The following Examples are meant to illustrate the invention and are not meant to limit the scope of the invention in any way.

EXPERIMENTAL EXAMPLES

Example 1

Yucatan Miniature Pigs and Cells for Gene Targeting

The Yucatan miniature pig was selected for development of cancer model in large animals. While it possesses the same biological characteristics as domestic pigs, the Yucatan miniature pig is significantly smaller. Most domestic pig breeds reach 100 kg in less than six months and can achieve weights of 250-300 kg within a few years. Yucatan miniature pigs reach a full-grown size of 65-90 kg at two years of life, which is more similar to an adult human. Therefore, the Yucatan miniature pigs are less expensive to house and feed. Additionally, this breed is more docile in nature and better suited for interactions with researchers. See, e.g., Panepinto, L. M., et al., Lab Anim Sci 1986, 36 (4), 344-7.

Due to the lack of suitable porcine embryonic stem cell lines, the standard methods for producing gene-targeted mice are not applicable in pigs (Piedrahita, J. A., Theriogenology 2000, 53 (1), 105-16). Instead, gene targeting must be achieved in a somatic cell that is then used as a nuclear donor for SCNT. While numerous cell types can be used as nuclear donors, only fetal fibroblasts have been used to successfully create gene-targeted pigs. Fibroblasts previously obtained from male and female Yucatan miniature pig fetuses at day 35 of gestation were selected. Fibroblasts from the Yucatan breed behave similar to domestic pig fibroblasts in culture, gene transfer, and for SCNT (Estrada, J. L., et al. Cloning Stem Cells 2008, 10 (2), 287-96).

Example 2

Creation of Targeting Constructs

TP53

As mentioned above, porcine TP53 has been sequenced and annotated, and the genomic structure is similar to the human gene. In one example, homologous recombination was used to create gain of function knockin in porcine TP53. Most mutations seen in human TP53 are missense mutations (Joerger, A. C., et al., Cold Spring Harb Perspect Biol 2010, 2 (6), a000919). Therefore, a pig with a human-relevant modification would be the preferred platform for developing specific models of human cancer. A knockin model with a missense mutation (R167H) that corresponds to the R175H "hot-spot" mutation commonly seen in human cancers was produced using the methods disclosed herein. FIG. 3A shows a structural mutation in the DNA-binding domain of p53 that is found prominently in patients with Li-Fraumeni syndrome (LFS). LFS is caused by germline mutations in TP53 and is characterized by a strong predisposition to tumor development. It is known that mice with this mutation suggest a gain of function mechanism that includes increased frequency of metastasis. See Olive, K. P., et al., Cell 2004, 119 (6), 847-60; Lang, G. A., et al., Cell 2004, 119 (6), 861-72. A neomycin-resistance cassette ($Neo^R$) was inserted into the upstream intron in order to select properly targeted cells. The $Neo^R$ is flanked by loxP sites and will be excised by Cre recombinase at a later stage.

Although this example describes a knockin model with a missense mutation corresponding to the known R167H mutation, other knockin mutations in TP53 are within the scope of the present invention. p53 sequence and function is highly conserved across species, and as previously mentioned, the orthologous mutation in mice recreates the human dysfunction. See, e.g., Olive, K. P., et al., Cell 2004, 119 (6), 847-60; Lang, G. A., et al., Cell 2004, 119 (6), 861-72; Donehower, L. A., et al., Nature 1992, 356 (6366), 215-21; Burr, P. D., et al., Oncogene 1999, 18 (35), 5005-9. Other frequently mutated sites in human TP53, including, for example, Y220, G245, R248, and R273, are conserved in porcine TP53 and are equally effective, alternate targets. See Joerger, A. C., et al., Cold Spring Harb Perspect Biol 2010, 2 (6), a000919.

In another example, A TP53 knockout pig will allow for the development of cancer models in the absence of p53. The TP53-deficient animal will also provide a starting point for developing a "humanized" cancer pig in which mutant human TP53 can be inserted as a transgene on the knockout background. To generate the knockout model, the TP53 coding sequence must be disrupted. A $Neo^R$ cassette is inserted into exon 5 of porcine TP53, as shown in FIG. 3B. Exon 5 encodes a critical region of the DNA-binding domain (Joerger, A. C., et al., Cold Spring Harb Perspect Biol 2010, 2 (6), a000919). In addition, a premature termination codon is engineered immediately upstream of the $Neo^R$ insertion. This strategy maximizes the likelihood of a non-functional p53. The most likely consequence of this mutation is the induction of nonsense-mediated mRNA decay (Wen, J., et al., Biochem Soc Trans 2008, 36 (Pt 3), 514-6). However, should a protein be translated, it would be truncated in the DNA-binding domain and be non-functional. An additional possibility could be the skipping of exon 5 via nonsense-associated alternative splicing (Wang, J., et al., Mol Cell 2002, 10 (4), 951-7). This, too, would result in a protein with little or no ability to bind DNA or activate transcription. Importantly, a similar strategy to disrupt TP53 exon 5 in mice resulted in no detectable mRNA or protein. See Donehower, L. A., et al., Nature 1992, 356 (6366), 215-21.

ATM

Figure 4:
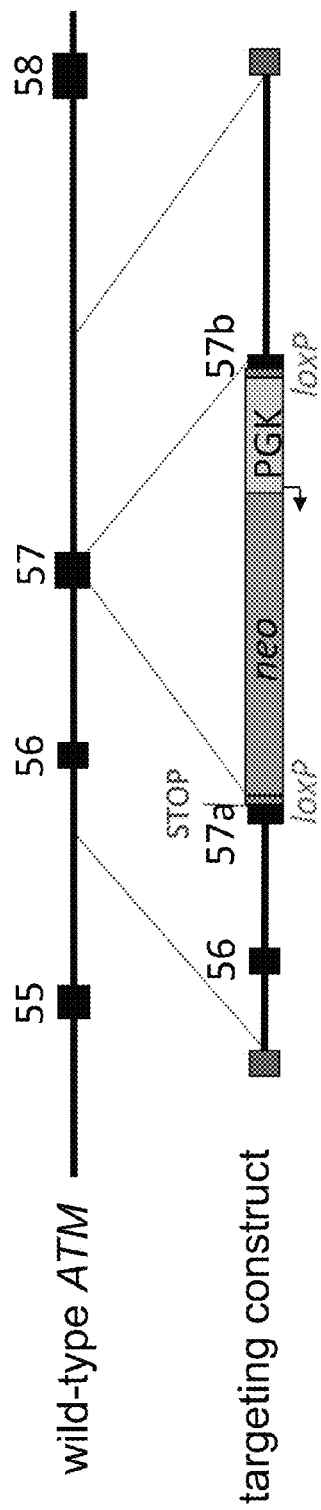
FIG. 4 shows a schematic drawing (not drawn to scale) of the gene targeting vector (SEQ ID NO: 2) used to disrupt porcine ATM, described in corresponding Appln. Ser. No. 61/788,080, filed Mar. 15, 2013. Exons 55-58 of porcine ATM are depicted in black boxes. $Neo^R$ contains a neomycin resistance cDNA driven by the phosphoglycerate kinase (PGK) promoter and flanked by loxP sites. The rAAV inverted terminal repeats (ITRs) are also shown as white dotted boxes. Each homology arm is about 1.4 kb in length.

The creation of an ATM-targeting vector is described in co-pending U.S. Appln. No. 61/788,080, filed Mar. 15, 2013. Homologous recombination was used to disrupt the endogenous ATM gene. Specifically, a neomycin-resistance cassette ($Neo^r$) was inserted into exon 57 of porcine ATM (FIG. 4). Exon 57 encodes a significant portion of the ATP-binding region within the kinase domain and it is known that a similar strategy to target ATM exons 57 and 58 in mice abolished ATM function (Herzog, K. H., et al., Science, 1998. 280(5366): p. 1089-91). A premature termination codon was also engineered immediately upstream of the $Neo^R$ insertion. This strategy was adopted to maximize the likelihood of a non-functional ATM.

A plasmid carrying the ATM targeting vector was generated using standard molecular biology techniques. Proper sequence was confirmed by DNA sequence analysis. The plasmid was then submitted to the University of Iowa Gene Transfer Vector Core for production of rAAV.

TP53 and KRAS

We chose to mutate both KRAS and TP53 as these are the most commonly mutated genes in human cancers, and altering these genes has been used to model many human cancers in mice. Importantly, mutations of these two genes co-operate to promote cancer. Specifically, activation of the oncogenic allele of KRAS in most mouse tissues leads to hyperplasia, and then only after an extended period of time and at a very low frequency, progresses to cancer. See Rangarajan, A., et al., Cancer Cell 2004, 6 (2), 171-83; Hamad, N. M., et al., Genes Dev 2002, 16 (16), 2045-57. However, the addition of a TP53 mutation greatly accelerates the progression to cancer. We chose to target KRAS (in the mutated TP53 knockin model described herein) at the endogenous level because transgenic over-expression of these mutant proteins can yield artifactual phenotypes. Tuveson, D. A., et al., *Cancer Cell* 2004, 5 (4), 375-87. For example, mouse cells proliferate in culture when an inducible oncogenic KRAS allele is activated, whereas ectopic expression of the same mutant protein arrests cells.

Homologous recombination can be used to generate a conditional KRAS mutation in TP53-targeted (and wild-type) cells. Specifically, the common G12D mutation can be introduced in KRAS exon 1. $KRAS^{G12D}$ is an "activating" mutation resulting in constitutive GTPase activity and acts via a dominant mechanism of pathogenesis. Schubbert, S., et al., *Nat Rev Cancer* 2007, 7 (4), 295-308. A lox-Stop-lox cassette may also be introduced with the G12D mutation to allow for the conditional expression of the mutation. This KRAS targeting construct is packaged in recombinant adeno-associated virus (rAAV) for efficient delivery to porcine fetal fibroblasts.

Figure 5:
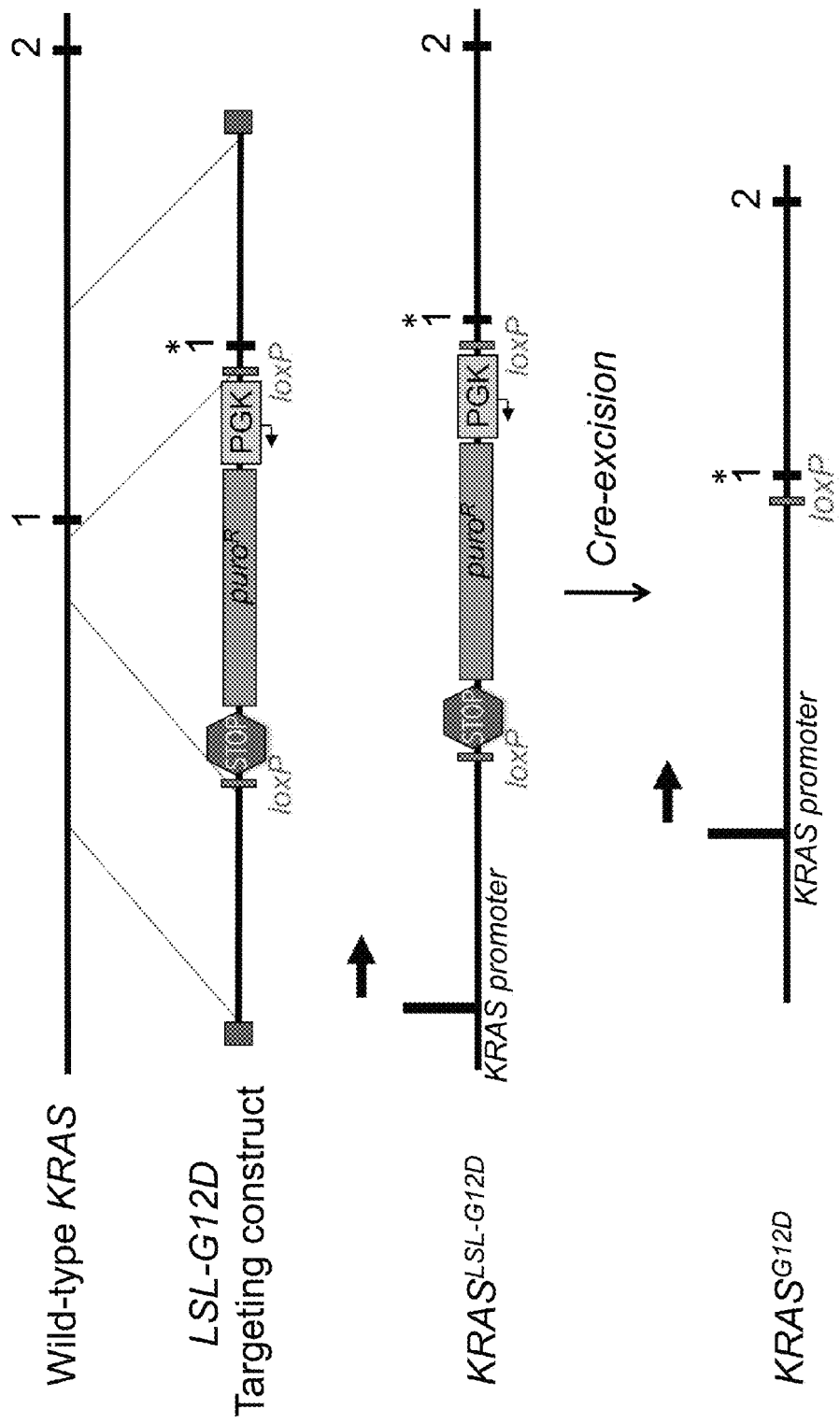
FIG. 5 shows a schematic drawing (not drawn to scale) of the gene targeting vector (SEQ ID NOS: 3 and 4) used to modify porcine KRAS. Exons 1 and 2 of porcine KRAS are depicted as black boxes. The G12D mutation is shown with an asterisk. The LSL cassette contains a transcriptional/translational stop domain (STOP), a puromycin resistance cassette ($puro^R$) driven by the phosphoglycerate kinase (PGK) promoter and is flanked by loxP sites. The rAAV inverted terminal repeats (ITRs) are shown as white dotted boxes. Each homology arm is 1.0 kb in length.

In order to conditionally express $KRAS^{G12D}$, a lox-STOP-lox (LSL) cassette can be inserted upstream of exon 1, as shown in FIG. 5. The LSL cassette will prevent expression of $KRAS^{G12D}$ from the targeted allele except in the presence of Cre-recombinase. Tuveson, D. A., et al., *Cancer Cell* 2004, 5 (4), 375-87. In this model, the non-targeted allele is unaffected, which is important as homozygous KRAS mutations result in embryonic lethality. This inducible system allows for site-specific expression of the $KRAS^{G12D}$ allele in almost any tissue by delivering Cre with a virus or by crossing with a pig expressing Cre via a tissue-specific promoter. This method has been used successfully in several KRAS/TP53-targeted mouse models. See Tuveson, D. A., et al., *Cancer Cell* 2004, 5 (4), 375-87; Lakso, M., et al., *Proc Natl Acad Sci USA* 1992, 89 (14), 6232-6; Guerra, C., et al., *Cancer Cell* 2003, 4 (2), 111-20. The LSL-cassette also contains a puromycin resistance cassette (puroR) that can be used for antibiotic selection of gene targeted cells.

Fibroblasts from TP53-targeted fetuses will be infected with rAAV carrying the KRAS targeting vector. The generation of targeted cells is designed to maximize the frequency of homologous recombination, minimize random integration, and minimize the number of cell passages before targeted cells are harvested. PCR and Southern blotting is used to identify properly targeted cells. KRAS-targeted cells are then prepared for somatic cell nuclear transfer.

Targeting Vectors and Plasmid Creation

Figure 3:
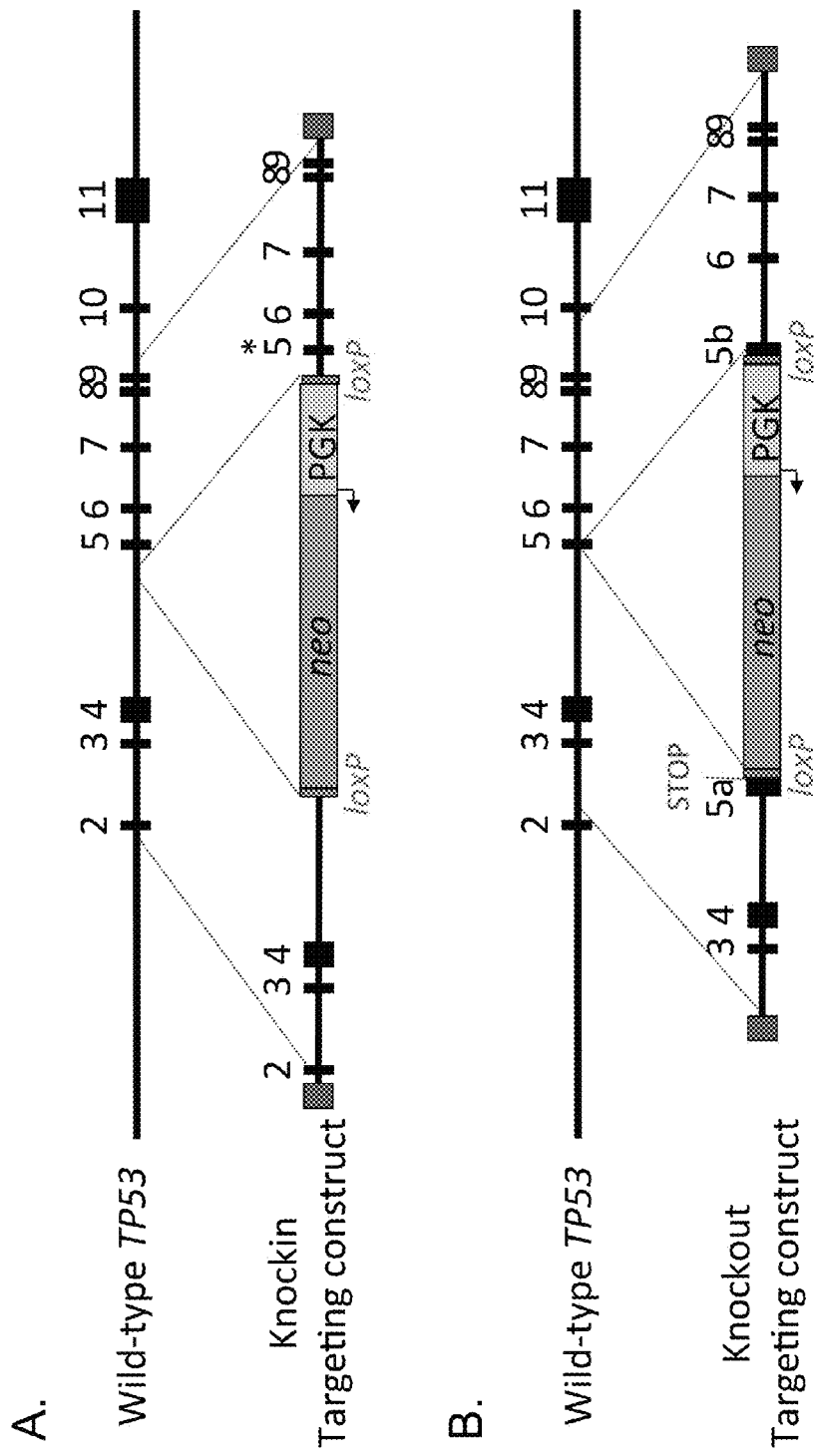
FIG. 3 is a schematic drawing (not drawn to scale) of the gene targeting vector (SEQ ID NO: 1) used to modify porcine TP53.

Because of rAAV genome size constraints, the total length of the targeting vectors is limited to about 4.5 kb. In the example of a TP53 knockin targeting vector or a TP53 knockout targeting vector, the 1.7 kb $Neo^R$ is centrally located in the vector, with each homology arm being ~1.2 to 1.4 kb, as shown in FIG. 3.

In the example of a KRAS targeting vector, the 2.5 kb LSL-cassette is centrally located in the targeting vector, with each homology arm being about 1.0 kb, as shown in FIG. 5. These arms would be considered short for traditional gene targeting vectors, but are not unusual for rAAV-mediated gene targeting.

A plasmid carrying the targeting vectors described herein was generated using standard molecular biology techniques. Proper sequence was confirmed by DNA sequence analysis. The plasmid was then submitted to the University of Iowa Gene Transfer Vector Core for production of rAAV. rAAV was chosen because it has been used to efficiently deliver gene targeting vectors to cell lines and primary cells (Meyerholz, D. K., et al., *Am J Respir Crit Care Med* 2010, 182 (10), 1251-61). Additionally, as mentioned above, rAAV has previously been used to engineer specific mutations in porcine CFTR and LDLR. See, e.g., Rogers, C. S., et al., *J Clin Invest* 2008, 118 (4), 1571-7; Rogers, C. S., et al., *Science* 2008, 321 (5897), 1837-41, U.S. Pat. No. 7,989,675; U.S. patent application Ser. Nos. 13/288,720, 13/368,312 and 13/624,967.

Example 3

Targeting TP53 and KRAS in Porcine Fetal Fibroblasts

Approximately $1.5 \times 10^6$ Yucatan miniature pig fetal fibroblasts—both male and female—were infected with rAAV1 (MOI≅100,000) carrying a TP53 targeting vector (SEQ ID NO: 1). After 24 hours, cells were transferred to a series of 96-well plates and G418 (100 µg/ml) was added to the media for selection of targeted cells. Fourteen days later, surviving cells were observed in 40-50% of wells, and each well of the 96-well plates were "replicated" by splitting among three plates: 1) 96-well culture plates for cell expansion, 2) 96-well culture plates for potential cryopreservation, and 3) 96-well PCR plates for cell lysis.

Cell lysates were screened by PCR to identify wells containing gene-targeted clones and any PCR-positive clones were frozen. The PCR screen amplified a product that can only be the result of proper targeting and placement of $Neo^R$. See FIGS. 6A and 6B. In this example, allele-specific Southern blot was employed to identify the $Neo^R$-positive PCR products that also contain the R167H mutation.

Figure 6:
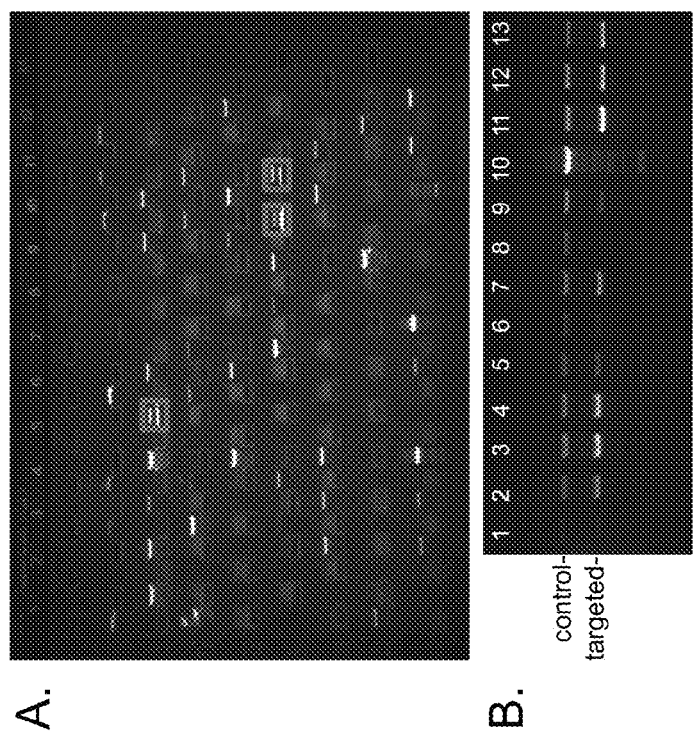
FIG. 6 shows a PCR screen identifying TP53-targeted cells.

By the time any targeted cells were frozen, they had been in culture only 15-17 days. This short time frame is important as the longer cells are in culture, the less efficient they are as nuclear donors. Positive clones from the "cell expansion" plates were also passaged to provide genomic DNA for downstream applications. Because "cell expansion" plates often senesce before large quantities of genomic DNA can be obtained, genomic DNA from the 96-well expansion plate was isolated and used whole-genome amplification (REPLI-g, Qiagen) to provide DNA for Southern blot analysis. Results for the targeting construct are shown in FIG. 6.

Figure 7:
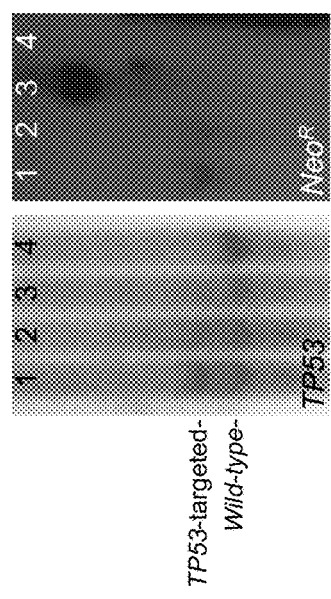
FIG. 7 shows a Southern blot of TP53-targeted cells. AflII/EcoNI digested DNA from PCR-positive cells was hybridized with a probe that detects porcine TP53 downstream of the targeting vector boundary. The TP53-targeted allele produced an approximately 6.0 kb band, and the wild-type band is approximately 4.3 kb. (Right) The same DNA was hybridized with a probe that detects the $Neo^R$ cassette, yielding only the targeted 7.8 kb band. Lanes 1 and 2 contain DNA from $TP53^{R167H/+}$ cells, while lane 3 represents non-targeted cells. Lane 4 contains DNA from a wild-type pig.

Genomic Southern blots with TP53- and $Neo^R$-specific probes were used to identify clones with a targeted TP53 allele and that were free of random integration. DNA sequence analysis was used to confirm the desired TP53 mutation (FIG. 7). Furthermore, three $TP53^{R167H/+}$ male cell lines and three $TP53^{R167H/+}$ female cell lines were identified to date that meet the above criteria—processing all of the PCR-positive cell lines was not necessary; however, those cells and DNA have been preserved, if needed. It is believed the quality and quantity of these cells are ideal for SCNT, and they were used to generate TP53-targeted heterozygote pigs. Gene targeting statistics are shown in Table 3.

TABLE 3

Summary of TP53 targeting efficiency and SCNT activity

| | Gene targeting efficiency* | Number of transfers | Embryos per transfer (average) | Pregnancy rate † | Live pigs per litter |
|---|---|---|---|---|---|
| Male | 1.1% | 3 | 130 | 67% | 3 |
| Female | 1.0% | 4 | 130 | 75% | 8 |

*Gene targeting efficiency reported as percentage of $G418^R$ clones that were properly targeted, as determined by PCR.
† Pregnancy rate refers to full-term gestation.

Because of the current lack of Cre recombinase-expressing pigs, the $Neo^R$ cassette is removed from the knockin pigs after the generation of the first animals. In a further step, ear-derived fibroblasts are obtained from knockin pigs infected with AAV-Cre to excise the Neo$^R$ cassette, and then used as nuclear donors in another round of SCNT.

The procedure described herein is repeated to identify and generate KRAS/TP53-targeted pigs. Specifically, after replication by splitting among three plates 96-well plates, cell lysates are screen by PCR to identify wells containing KRAS-targeted clones and any clones that are PCR-positive are frozen. The PCR screen takes advantage of the size difference caused by the insertion of the 2.5 kb LSL-cassette. An allele-specific Southern blot is employed to identify the PCR-positive products that also contain the G12D mutation.

As discussed above, by the time cells are frozen, they will have been in culture only 15-17 days. Positive clones are also passaged from the "cell expansion" plates to provide genomic DNA for downstream applications. Should "cell expansion" plates senesce before sufficient genomic DNA can be obtained, we will use whole-genome amplification to provide DNA for the Southern blot. Genomic Southern blots using KRAS- and puro$^R$-specific probes identify clones with a targeted KRAS allele and that are free of random integration. Furthermore, DNA sequence analysis is used to confirm the desired mutation. All clones that meet these criteria will be considered ideal for SCNT and used to generate KRAS/TP53-targeted pigs.

Example 4

Nuclear Transfer and Propagation

TP53$^{R167H/+}$ male and female cells were used for somatic cell nuclear transfer (SCNT) to produce live male and female TP53$^{R167H/+}$ offspring. The resulting litters were born August 2011 and produced a total of 6 TP53$^{R167H/+}$ male and 24 TP53$^{R167H/+}$ female piglets.

Figure 8:
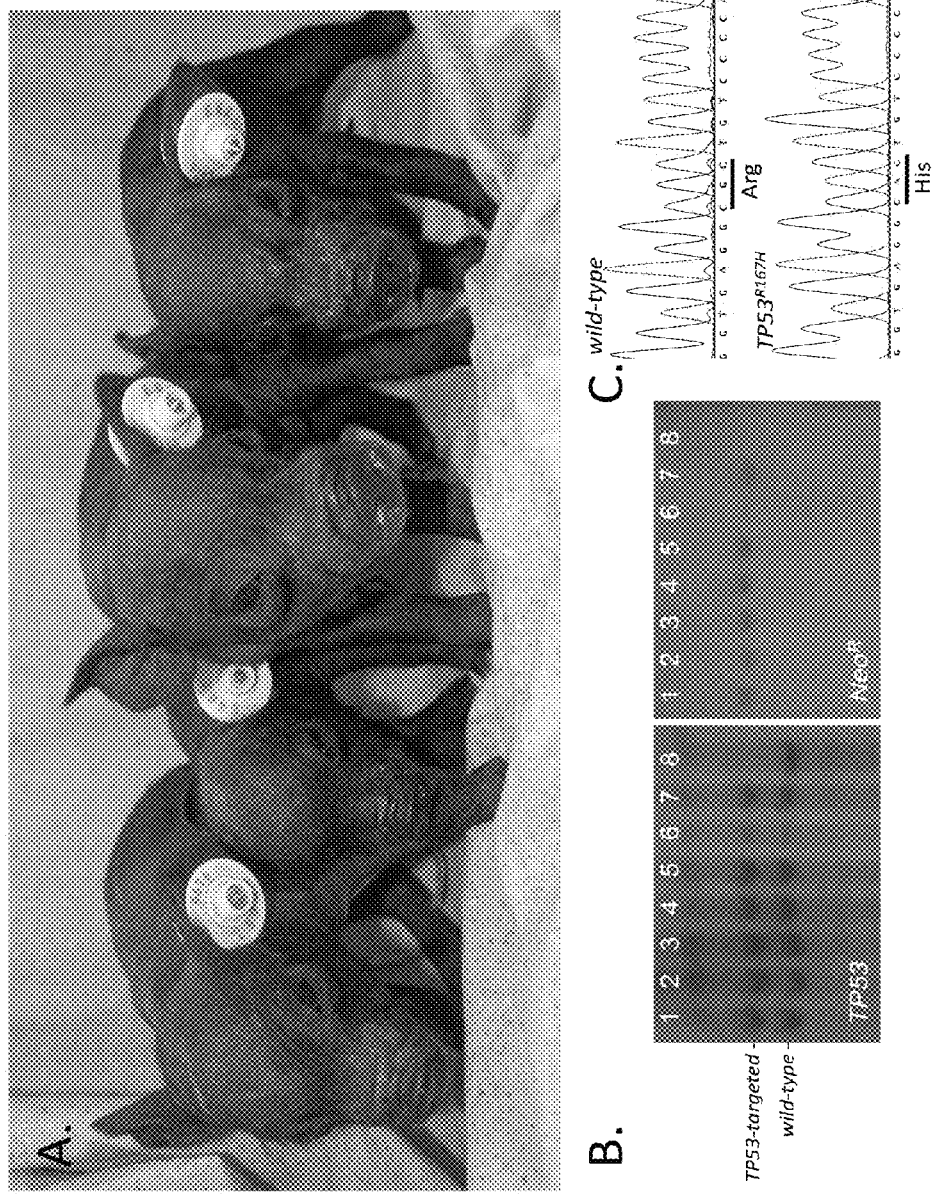
FIG. 8 shows TP53-targeted pigs.

FIG. 8 shows some of the first TP53-targeted piglets (FIG. 8A) as well as Southern blot and DNA sequencing confirming the proper genotype (FIGS. 8B and 9C). Without intervention, these pigs are expected to develop a limited spectrum of tumors throughout the body, just as humans and mice with analogous TP53 mutations. While these animals may serve as a useful model on their own, an additional benefit results from being a "sensitized" platform for adding second "hits", such as a conditional KRAS mutation. This has been a hugely successful approach with recent murine models. See, e.g., Jackson, E. L., et al., Genes Dev 2001, 15 (24), 3243-8; Caulin, C., et al., J Clin Invest 2007, 117 (7), 1893-901; Kirsch, D. G., et al., Nat Med 2007, 13 (8), 992-7.

Figure 9:
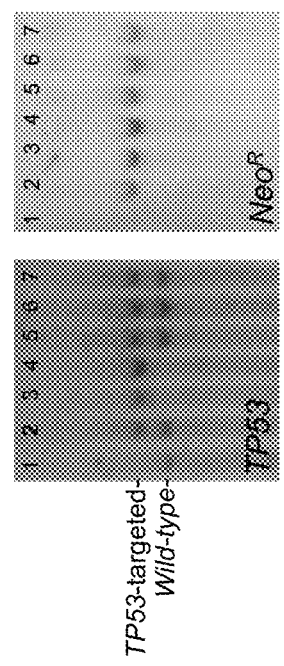
FIG. 9 shows a genomic Southern blot of wild-type, TP53-heterozygote, and TP53-homozygote piglets. On the left, AflII/EcoNI digested genomic DNA was hybridized with a probe that detects porcine TP53 downstream of the targeting vector boundary. The TP53-targeted allele produced an approximately 6.0 kb band, and the wild-type band is approximately 4.3 kb. On the right, the same DNA was hybridized with a probe that detects the Neo$^R$ cassette, yielding only the targeted 7.8 kb band. Lane 1 contains DNA from a wild-type piglet. Lanes 2, 5, 6, and 7 contain DNA from TP53$^{R167H/+}$ piglets. Lanes 3 and 4 contain DNA from TP53$^{R167H/R167H}$ piglets.

Male and female heterozygotes were also bread to produce TP53-homozygote pigs, which were born in August 2012 (FIG. 9). These animals could have an even more severe and early-onset tumor formation.

Example 5

Methods of Developing and Analyzing TP53$^{R167H/R167H}$ Pigs

The following methods were used to create and evaluate the pigs discussed in Example 6.

Fetal Fibroblast Isolation. Fetal fibroblasts were isolated from approximately day 35 Yucatan miniature pig fetuses by the methods described herein and known in the art. See also Lai, L. et al., Cloning Stem Cells 5:233-241 (2003). Cells were grown at 39° C. and 5% $CO_2$ in F10 media (Invitrogen) containing 20% FCS and 30 µg/ml gentamicin. Fetus genders were previously identified by PCR amplification of the Y-chromosome-specific Sry gene by methods known in the art. See, e.g., Pomp, D. et al., Journal of Animal Science 73:1408-1415 (1995).

Cloning Porcine TP53 Genomic DNA. Genomic DNA was isolated from Yucatan fetal fibroblasts (Qiagen). A 7.1 kb PCR product which included a region from TP53 exon 2 to exon 11 was amplified using a high fidelity polymerase (Platinum Taq High Fidelity; Invitrogen) and TP53 primers GC2F and GC2R (see Table 4 for all primer sequences). The PCR product was subcloned into pCR2.1-TOPO (Invitrogen) and sequenced. This plasmid (referred to as pTP53) served as the template for PCR amplification of the 5' and 3' homologous targeting arms.

TABLE 4

| PCR and Sequencing primers (all sequences 5' to 3') | |
|---|---|
| pTP53seq 1F: | CGCTCTCAATAATAGAGAACC (SEQ ID NO: 7) |
| pTP53seq 2F: | GAAATCATGCAGTGAATTTAAGT (SEQ ID NO: 8) |
| pTP53seq 3F: | CTAGGTCAACATAAAGGAGCG (SEQ ID NO: 9) |
| pTP53seq 4F: | TGAGCTGGGAGATGAGATGA (SEQ ID NO: 10) |
| pTP53seq 5F: | AGGGTGCTAGAAGATGAGATC (SEQ ID NO: 11) |
| pTP53seq 6F: | TGCAATGGAGGAGTCGCAG (SEQ ID NO: 12) |
| pTP53seq 7F: | CCTGGCAGCTATGATTTCCG (SEQ ID NO: 13) |
| pTP53seq 8F: | GTGCAGCTGTGGGTCAGC (SEQ ID NO: 14) |
| pTP53seq 9F: | CTCACTTGACCTGCCGCAG (SEQ ID NO: 15) |
| pTP53seq 10F: | GCTGGCTTTCCTCACTGC (SEQ ID NO: 16) |
| pTP53seq 11F: | GCTTGACTCTTGTAGTGCATA (SEQ ID NO: 17) |
| pTP53seq 12F: | GCGAGTTAAGAACTGGACTAG (SEQ ID NO: 18) |
| pTP53seq 13F: | TTCCCACTTCTAGCAACCCT (SEQ ID NO: 19) |
| pTP53seq 6R: | CTGCGACTCCTCCATTGCA (SEQ ID NO: 20) |

TABLE 4-continued

PCR and Sequencing primers (all sequences 5' to 3')

| Primer | Sequence |
|---|---|
| pTP53seq 7R: | CGGAAATCATAGCTGCCAGG (SEQ ID NO: 21) |
| pTP53 5'armF (EcoRV): | gatcga*gatatc*GAGGTGTTTTCAGTGCCATTA (SEQ ID NO: 22) |
| pTP53 5'armR (EcoRV): | gatcga*gatatc*CAGCCAAGTGCTCGGTGG (SEQ ID NO: 23) |
| pTP53 3'armF (BamHI): | gatcga*ggatcc*CTAATCAGTATTTAGGCAGCG (SEQ ID NO: 24) |
| pTP53 3'armRv2 (HindIII): | gatcga*aagctt*GGTTGCAGAAGAGACTCCG (SEQ ID NO: 25) |
| R167H-F: | TGACCGAGGTGGTGAGGCACTGTCCCCACCATGAGCG (SEQ ID NO: 26) |
| R167H-R: | CGCTCATGGTGGGGACAGTGCCTCACCACCTCGGTCA (SEQ ID NO: 27) |
| TP53-R167H-AAV-F (NotI): | agctacat*gcggccgc*GCTGAGTTACTTCATCCTGAT (SEQ ID NO: 28) |
| TP53-R167H-R (NotI): | agctacat*gcggccgc*CAAAAGGATGGCTAGAGAAAC (SEQ ID NO: 29) |
| Screen F (NeoR): | AGACGTGCTACTTCCATTTGTCAC (SEQ ID NO: 30) |
| pTP53 PCR-R1: | TCAATCTCTCAAACCCGATAG (SEQ ID NO: 31) |
| LDLR 5F: | AGCCACAGCTCATCACTCC (SEQ ID NO: 32) |
| LDLR-Exon5R1: | AGCACTGGAACTCGTCAGG (SEQ ID NO: 33) |
| P53oligoProbe-3: | GTGAGGCACTGTCCCC (SEQ ID NO: 34) |
| PGK-NeoF: | CCAGTGTGCTGGAATTCGG (SEQ ID NO: 35) |
| NeoR-R: | CTGCAGAATTCGGCTTGTACT (SEQ ID NO: 36) |
| pTP53 Southern probe 3F: | GATGTGGCTCGGATCTGGT (SEQ ID NO: 37) |
| pTP53 Southern Probe 3R: | CCATGTTCCTCCCTGCTCC (SEQ ID NO: 38) |
| PGK-F: | GGCTGCTAAAGCGCATGCT (SEQ ID NO: 39) |
| P53 Geno 4F: | ACCCTGCCATCTCTGGCTA (SEQ ID NO: 40) |
| P53NeoExc.Screen 3R: | AGAGCGAACAGAAGGTCAGA (SEQ ID NO: 41) |

Italicized letters indicate restriction enzyme sequences for cloning.
Underlined letters indicate the R167H codon.

Targeting Vector Construction. The 5' and 3' homologous recombination arms were amplified by PCR using plasmid pTP53 and subcloned sequentially into a plasmid containing a PGK-Neo cassette. The primers for the 5' arm were pTP53 5'armF (EcoRV) and pTP53 5'armR (EcoRV). The primers for the 3' arm were pTP53 3'armF (BamHI) and pTP53 3'armRv2 (HindIII). The R167H mutation was introduced using site-directed mutagenesis with primers R167H-F and R167H-R. This targeting construct (pTP53-Neo) was used as a template to create the amplicon for the generation of the TP53-R167H-targeting proviral vector.

rAAV Production. PCR amplification of a 4.5 kb amplicon from plasmid pTP53-Neo was achieved by using the following primers: TP53-R167H-AAV-F (NotI) and TP53-R167H-R (NotI). This product was subcloned into the rAAV proviral plasmid, pFBAAV2-CMVP.NpA (obtained from University of Iowa Gene Transfer Vector Core) and grown in Sure2 cells (Stratagene) to ensure ITR integrity. This proviral plasmid is referred to as pAAV-TP53-R167H-Neo. The rAAV was produced by the University of Iowa Gene Transfer Vector Core.

Fetal Fibroblast Infection and Selection. Passage zero male and female Yucatan fetal fibroblasts ($1.0 \times 10^6$) were thawed and plated on separate 100 mm collagen-coated culture dishes containing PFF media. Each cell line was infected with rAAV (18 µl, $4.65 \times 10^{13}$ vg/ml) after 24 hours. Cells were subsequently detached with trypsin 24 hours later and plated on 64, 96-well collagen-coated plates at a density of 200 cells/well. Selection was initiated 48 hours later with G418 (100 µg/ml). Ten days later each infected cell plate was split among three 96 well plates (one plate for freezing, one for propagation, and one to a PCR plate for immediate PCR screening). The freeze and propagation plates were returned to the incubator.

PCR Screen and Cell Handling. Approximately 40% of wells contained live cell colonies following selection. Cells in the 96-well PCR plate were subjected to 5 µl lysis buffer (50 mM KCl, 1.5 mM MgCl2, 10 mM Tris-Cl, pH 8.5, 0.5% Nonidet P40, 0.5% Tween, 400 µg/ml Proteinase K) by methods known in the art. See, e.g., McCreath, K. J., et al., *Nature* 405:1066-1069 (2000). Cell lysis plates were incubated 65° C. for 30 minutes, followed by 95° C. for 10 minutes. Primers Screen F (NeoR), pTP53 PCR-R1, LDLR 5F, and LDLR-Exon5R1 were used to PCR amplify 2 µl of lysate with the following conditions: 2 min. at 95° C., 30 cycles of 95° C. for 20 s, 56° C. for 20 s, and 68° C. for 4.5 min., and finally 68° C. for 7 min. The LDLR amplicon served as an internal control. The expected product for the targeted TP53 allele was 1.9-kb and 4.3-kb for the LDLR product. The PCR-positive cells were grown to 100% confluence and either cryo-preserved or expanded for the purpose of DNA isolation.

R167H-specific Southern Blot. The PCR-positive PCR reactions were run on a 1.0% agarose gel and denatured in 0.5M NaOH/1.5M NaCl for 20 minutes and transferred to a positively charged nylon membrane (Roche) in 20×SSC overnight. The membrane was washed in 5×SSC for 5 minutes, air dried, and UV crosslinked. Detection of R167H was achieved by Chemiluminescent Nucleic Acid Detection (Thermo Scientific) and a biotin labeled probe. The membrane was prehybridized in 15 ml Hybridization solution at 53.5° C. The DNA was hybridized with 15 µl (30 ng/µl) of biotin labeled probe, P53oligoprobe-3 (IDT DNA), for 90 minutes at 53.5° C. The membrane was washed in Stringency Wash Buffer then incubated in Blocking Buffer. HRP conjugate was added to the Blocking Buffer and incubated at 15 minutes at room temperature. The membrane was washed in Wash Buffer then incubated in Substrate Equilibration Solution. Finally, the membrane was incubated in Luminol/Peroxidase Substrate and exposed to film (Kodak BioMax) for 1 second.

Southern Blot. To validate PCR-positive cell lines, genomic DNA was isolated from the cells grown on propagation culture plates. Two to ten nanograms of genomic DNA was used for whole genome amplification (Repli-G; Qiagen) and digested with AflII and EcoNI overnight. Following gel electrophoresis, samples were transferred to a positively charged nylon membrane (Roche) using an alkaline transfer procedure. The membrane was briefly rinsed in 5×SSC, completely dried and subjected to UV crosslinking. The DNA probes for TP53 and $Neo^R$ were produced by PCR amplification using the following primers: pTP53 Southern probe 3F/pTP53 Southern Probe 3R and PGK-NeoF/NeoR-R, respectively. Probes were labeled with $\alpha$-$^{32}$P by random priming using Prime-a-Gene Labeling System (Promega), and the radioactive probes were purified using CHROMA SPIN+TE-100 columns (Clontech). Membranes were prehybridized in Rapid-hyb Buffer (GE Healthcare Life Sciences) for 30 minutes at 65° C., then 25 µl of $^{32}$P-labelled probe was added and hybridization proceeded at 65° C. for 2 hours. The membrane was washed in 2×SSC, 0.1% SDS one time at room temperature for 20 minutes and in 0.1× SSC, 0.1% SDS at 65° C. three times for 15 minutes each. The membrane was exposed to film (Kodak BioMax MS) at −80° C. overnight. For confirming animal genotype, high molecular weight genomic DNA was isolated from pig umbilicus and digested with AflII and EcoNI. The remaining steps were performed as described above.

Genotyping of Offspring from Heterozygote Crosses. Lysis of fresh pig umbilicus was achieved using a Direct Amp Kit (Denville Scientific). The lysate was diluted in 50% water and 2 µl was directly added to a master mix containing primers PGK-F, P53 Geno 4F, and P53NeoExc.Screen 3R. PCR amplification was performed with the following reaction conditions: 2 min at 95° C., 35 cycles of 95° C. for 10 s, 60° C. for 10 s, and 68° C. for 15 s, and finally 68° C. for 3 min. The expected product for the targeted allele was 211-bp and the wild type allele was 114-bp.

Nuclear Transfer. Nuclear transfer was performed by Viagen, Inc. (Austin, Tex.) by methods known in the art. See, e.g., Walker, S. C., et al., Cloning Stem Cells 4:105-112 (2002). Briefly, TP53-targeted fetal fibroblasts were seeded in a 4-well plate and grown until contact inhibited. The cells were detached with trypsin and resuspended in salt-buffered NCSU-23 containing 10% FCS. Oocytes were matured in Earle's TC199-Hepes supplemented with 5 mg/mL insulin, 10 ng/mL EGF, 0.6 mM cysteine, 0.2 mM sodium pyruvate, 25 mg/mL gentamicin, 5 mg/mL FSH, and 10% porcine follicular fluid for 40 hours prior to manipulation.

Embryo Transfer. Embryo transfer was performed at Exemplar Genetics. Reconstructed oocytes were transferred into synchronized post-pubertal domestic gilts on the first day of standing estrus. Recipient gilts were preanesthetized with IV propofol (0.5-5 mg/kg) and anesthesia was maintained with inhaled isoflurane (3-5% in oxygen via face mask). Following a midline incision to access the uterus, reconstructed embryos were transferred into the oviduct at the ampullary-isthmus junction. Intra- and post-operative analgesia was provided by intramuscular injection of flunixin meglumine (2.2 mg/kg). Recipient animals were checked for pregnancy by abdominal ultrasound after day 21 and throughout gestation.

Checkpoint Analyses in Pig Fibroblasts. Induction of the DNA damage checkpoint or senescence in response to oncogene activation was examined in pig fetal fibroblasts expressing wild-type p53 or mutant alleles of $TP53^{R167H}$ following treatment with a DNA damaging agent or expression of mutant $KRAS^{G12V}$ protein, respectively. For the DNA damage response, early passage (P1 to P3) cells were plated at 5×10$^5$ cells per 10 cm dish and treated with or without 0.4 µg/ml doxorubicin (Adriamycin) for 3 days. Cells were harvested, cell viability measured by trypan blue staining and counting on a hemacytometer, and samples split for flow cytometric analysis of DNA content or western blot analysis, exactly as described (71). Antibodies used in western analyses were to p53 (Santa Cruz, sc-126 [DO-1], 1:200), p21 (BD Pharmingen, 554228, 1:100), and GAPDH (Abcam, Ab8245, 1:20,000). To assess senescence, early passage (P1 to P3) cells were infected with pBabe-puro control or pBabe-$KRAS^{G12V}$-puro retroviruses for two days, using identical methods of virus preparation and infection as known in the art. See, e.g., Modestou, M., et al., Cancer research 61:3145-3150 (2001); Huang, J., et al., Oncogene (2013). Infected cells were selected with 1 µg/ml puromycin for 2 days, replated at identical cell numbers, and the induction of senescence measured by cell counting and phase contrast microscopy 3 to 7 days later.

Clinical Evaluation. Pigs were monitored daily (2+ times/day) for clinical signs of morbidity by experienced animal care staff. Parameters that were monitored included, but were not limited to, loss of condition, lameness, reduced feed consumption, general morbidity and enlarged peripheral lymph nodes. Additionally, peripheral blood was collected every two months for complete blood count (CBC) and chemistries Clinical presentations of the affected cases are described in Table 6.

Peripheral Blood Analysis. Peripheral blood samples were collected from pigs every 4-6 weeks to monitor for signs of clinical disease. Samples were submitted to a commercial laboratory (Marshfield Labs, Marshfield, Wis.) for analysis. Values between non-diseased control cases and lymphoma cases were statistically analyzed using a two-way ANOVA (repeated measures) using Bonferroni post-tests and significance was placed at P<0.05.

Animal Preparation for Imaging. Pigs were transported to and from the University of Iowa on the day of the imaging procedure. All procedures were performed under anesthesia, induced with a mixture of telazol (2.2 mg/kg), ketamine (1.1 mg/kg) and xylazine (1.1 mg/kg), and maintained with 3-5% isoflurane. Pigs were mechanically ventilated through intubation with a balloon cuffed 7 mm-8 mm tracheal tube. Ventilation was performed at 100% oxygen with 5 cm $H_2O$ positive end expiratory pressure (PEEP), tidal volume of 10 mL/kg and an appropriate respiration rate to maintain an end-tidal (ET) $CO_2$ between 35 and 45 mmHg. Isoflurane anesthesia, ventilation and forced inspiratory breath-holds of 20 cm $H_2O$ were achieved throughout image data acquisition with a Primer SP MRI-Compatible Veterinary Anesthesia Ventilator (DRE Veterinary, Louisville, Ky.). Peripheral intravenous access was obtained via an ear vein cannula of size 20 gauge for the administration of contrast and flushed with heparinized saline (500 unit/L) to prevent unwanted blood clotting between administrations. Following computed tomography (CT) and magnetic resonance imaging (MRI) acquisition, animals were recovered.

Computed Tomography Acquisition. Four computed tomography (CT) datasets (non-contrast head CT, non-contrast chest-abdomen-pelvis CT, contrast chest CT, contrast abdominal and pelvic CT) were acquired utilizing a Somatom Definition Flash 128-multidector dual-source CT scanner (Siemens Healthcare, Erlangen, Germany). The head CT (Spiral, 120 kV, 390 mAs, 1 sec rotation time, pitch of 0.5, H31 reconstruction kernel, 0.5 mm slice thickness) was acquired to assess the skeletal structure and indicate if a brain MRI was warranted. A non-contrast enhanced chest-abdomen-pelvis CT scan was acquired during an enforced inspiratory breath hold at 20 cm $H_2O$ (Spiral, 120 kV, 210 mAs, 0.5 sec rotation time, pitch of 1, B35 kernel, 0.5 mm slice thickness). The enforced breath-hold eliminated respiratory motion artifact and increased the diagnostic quality of the dataset acquired. Finally, contrast enhanced CT data was acquired: 2 mL/kg nonionic iodinated contrast injected at 4 mL/sec, with 15 sec delay for thorax scan and 70 sec delay for abdomen, both with enforced inspiratory breath-holds (Spiral, 120 kV, 210 mAs, 0.5 sec rotation time, pitch of 1, B35 kernel, 0.5 mm slice thickness).

Magnetic Resonance Imaging Acquisition. Magnetic Resonance Imaging (MRI) data was obtained with a TIM Trio 3T MRI system (Siemens Healthcare, Erlangen, Germany). A high resolution brain scan was obtained to assess brain tumors using a 3D turbo spin echo with variable flip angle (SPACE) protocol [TR/TE=1630/119 milliseconds, flip angle 120°, echo train length 141, resolution of 0.86 mm×0.86 mm×0.9 mm slice thickness]. An additional axial diffusion tensor imaging protocol [TR/TE=2800/83 milliseconds, flip angle 90°, resolution of 1.5 mm×1.5 mm×5 mm slice thickness] was performed for detailed analysis of the white matter. For the chest and abdomen, standard T2-weighted scans acquired in the axial [TR/TE=4293/156, flip angle 120°, echo train length 109, resolution of 1.37 mm×1.37 mm×5 mm slice thickness] and coronal [TR/TE=4286/157, flip angle 120°, echo train length 109, resolution of 1.48 mm×1.48 mm×5 mm slice thickness] planes were used to assess areas of atypical fluid content, such as metastatic tumors or areas of inflammation. Due to the increased scan time, motion artifact was eliminated using respiratory navigation. A T1-weighted volume interpolated axial gradient echo (VIBE) contrast-enhanced abdominal sequence [TR/TE=4.34/1.9, flip angle 12°, resolution of 1.37 mm×1.37 mm×3 mm slice thickness] was acquired pre-contrast and 30, 60 and 180 seconds post administration of 0.2 mL/kg gadolinium contrast (MultiHance, Bracco Diagnostics Inc., Princeton, N.J.) injected through a peripheral ear vein. These scans were used to analyze blood flow through the liver and obtain greater anatomical detail of the abdomen. An additional post-contrast axial VIBE chest scan [TR/TE=4.34/1.92, flip angle 12°, resolution of 1.37 mm×1.37 mm×3 mm slice thickness] was acquired for additional anatomical detail of the lungs. Due to the short acquisition time with the VIBE scans, breath-holds at an inspiratory pressure of 20 cm $H_2O$ were used to reduce motion artifact.

Radiological Assessment: All image data was qualitatively evaluated by a radiologist (J.N.) with experience in porcine studies, using the OsiriX platform. See Rosset, A., et al., *Journal of digital imaging* 17:205-216 (2004). The Response Evaluation Criteria in Solid Tumors (RECIST) 1.1 was used to measure the tumor and lymph node size. See Eisenhauer, E. A., et al., *European journal of cancer* 45:228-247 (2009). Segmentation and volumetric rendering of the osteogenic tumor in the mesentery was achieved using OsiriX threshold based three-dimensional region growing algorithm with a 250-2000 HU threshold range.

Segmentation of the renal cell tumor at imaging time points 1 and 2 were achieved using tools from the Pulmonary Analysis Software Suite (PASS). See Guo, J., et al. Pulmonary Analysis Software Suite 9.0, New York City, USA. 283-292 (2008). The contrast enhanced venous phase (70 sec delay) 3.0 mm, thick axial CT scans were analyzed with PASS. Total volume (ml), as well as the mean, standard deviation and coefficient of variation of the CT attenuation (HU) were calculated from the segmented liver image. Using the pre and post contrast MRI sequences, the signal intensity of the tumor relative to that of the kidney was reported.

The liver and spleen were quantitatively assessed to determine the presence of lymphoma. Manually segmented liver organ volumes in the venous phase from contrast enhanced CT scans were done using PASS. In addition to identifying the boundary of the organ, large internal vessels were segmented and excluded. Total volume (ml), and the mean and standard deviation of the CT attenuation (HU) were calculated from the segmented liver images. The dynamic perfusion heterogeneity of the liver and spleen were quantitatively assessed using the MRI abdominal VIBE sequence data, including pre-contrast and 30, 60 and 180 seconds post contrast data acquisitions. PASS was utilized to obtain three to four square regions of interest (ROIs) within the liver, spleen and flank muscle. Areas with prominent, large vessels were excluded from the regions of interest. The liver-to-muscle and spleen-to-muscle ratios were computed along with coefficient of variation to assess overall MRI signal intensity and heterogeneity.

Tissues. Euthanasia was performed according to Institutional Animal Care and Use Committee approval. Necropsy examination and tissue collection procedures were coordinated by a veterinary pathologist experienced with genetically modified porcine models. Lesions identified by imaging techniques were targeted for examination and tissue collection, and the remaining tissues were screened for lesions. Collected tissues were placed in appropriate volumes (>20:1 fixative:tissue volumes) of 10% neutral buffered formalin for ~3-5 days. Formic acid (25%) was used to decalcify bony lesions/tumors. Samples were submitted to the Comparative Pathology Laboratory (Department of Pathology, University of Iowa) for standard tissue processing, embedding, and sectioning (~4 µm). Tissues were stained with hematoxylin and eosin (HE) for general examination by the veterinary pathologist.

Molecular Genetic Analyses of $TP53^{R167H/R167H}$ Tumors. Isolated tumors were quick frozen in liquid nitrogen for western analyses or placed in F10 media containing 20% FCS for subsequent culturing and cytogenetic analysis. Frozen tumor sections were pulverized with a mortar and pestle, lysed in an ice-cold RIPA lysis buffer (50 mM Tris, pH 8.0, 150 mM NaCl, 1 mM EDTA, 1% Triton X-100, 0.1% SDS, 0.5% sodium deoxycholate with protease and phosphatase inhibitors) and protein quantified by BCA analysis (Pierce). Equivalent amounts of protein (100 µg) from each sample were analyzed by SDS-PAGE and western blotting using enhanced chemiluminescence for protein detection (ECL, Amersham). Antibodies used included those against p53 and GAPDH (see above) as well as cyclin B1 (Santa Cruz, sc-752, 1:200).

Chromosome Analysis. Cell cultures were established from either wildtype pig skin fibroblasts or tumor cells derived from $TP53^{R167H/R167H}$ pigs. Cells were arrested in metaphase by adding ethidium bromide (final concentration 12.5 μg/ml) for 40 min followed by colcemid (final concentration 6 μg/ml). After 1-2 h, the cells were incubated for 25 min at room temperature with hypotonic solution (3:1 mixture of 0.8% sodium citrate and 0.075 M potassium chloride). Cells were then fixed three times with a 3:1 methanol/acetic acid. Chromosome spreading was performed on coverslips in a Thermotron chamber (Holland, Mich.). Coverslips were mounted on glass slides after the drying process. Ten to twenty G-banded metaphases were analyzed. Karyotype images were captured using the CytoVision computerized imaging system (Applied Imaging, USA).

Animals. This study was carried out in accordance with the recommendations in the Guide for the Care and Use of Laboratory Animals of the National Institutes of Health. All animals were developed and housed in Exemplar Genetics' AAALAC-accredited facilities. Standard procedures for animal husbandry were used throughout. The Institutional Animal Care and Use Committee (IACUC) of Exemplar Genetics and the University of Iowa approved all animal experiments. Imaging procedures were conducted at the University of Iowa in accordance with the IACUC approved protocol.

Example 6

Tumor Development in TP53$^{R167H/R167H}$ Pigs

Figure 12:
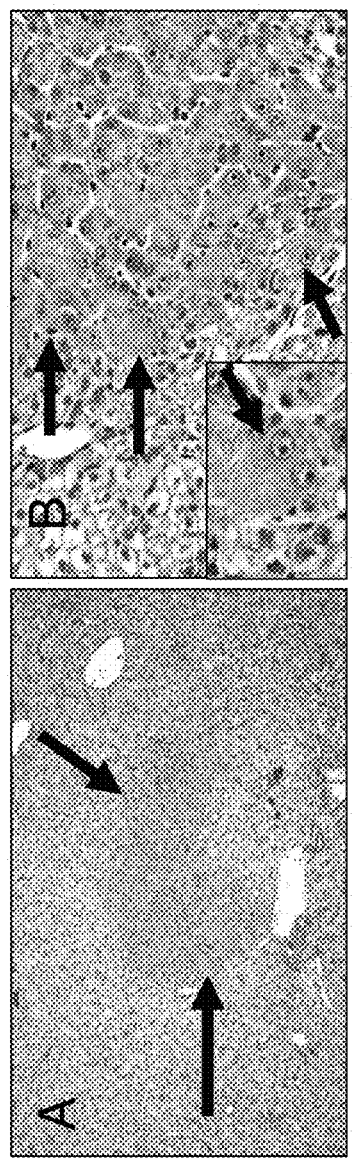
FIG. 12 is a photo of liver from a neonatal TP53$^{R167H/R167H}$ pig, Case 1.

TP53$^{R167H/R167H}$, TP53$^{R167H/+}$, and TP53$^{+/+}$ pigs were monitored with a combination of clinical evaluation, peripheral blood analysis, in-vivo CT and MRI, histopathology, and genetic characterization. The human-like size of this Yucatan miniature pig model enabled the use of clinical imaging technology and protocols (CT and MRI) for the longitudinal monitoring of tumorigenesis in this cohort. Table 5 provides a summary of the pigs having undergone necropsy, including age at necropsy, clinical signs, and type of tumors detected. There have been no tumors detected via in-vivo imaging or necropsy in the TP53$^{R167H/+}$ or TP53$^{+/+}$ cohort over 24 months of observation.

in the first litter of TP53$^{R167H/R167H}$ pigs died two hours after birth. The necropsy did not reveal any discreet tumors although the liver did have microscopic evidence of hepatocellular atypia (FIG. 12). While no other pigs in our cohort displayed similar atypia or overt tumors in any livers, TP53 mutations are associated with hepatocellular carcinoma. See, e.g., Hussain, S. P., et al., Oncogene 26:2166-2176 (2007). Therefore, future phenotypic studies of the model will help determine if this represents a precursor lesion for hepatocellular tumors.

Figure 13:
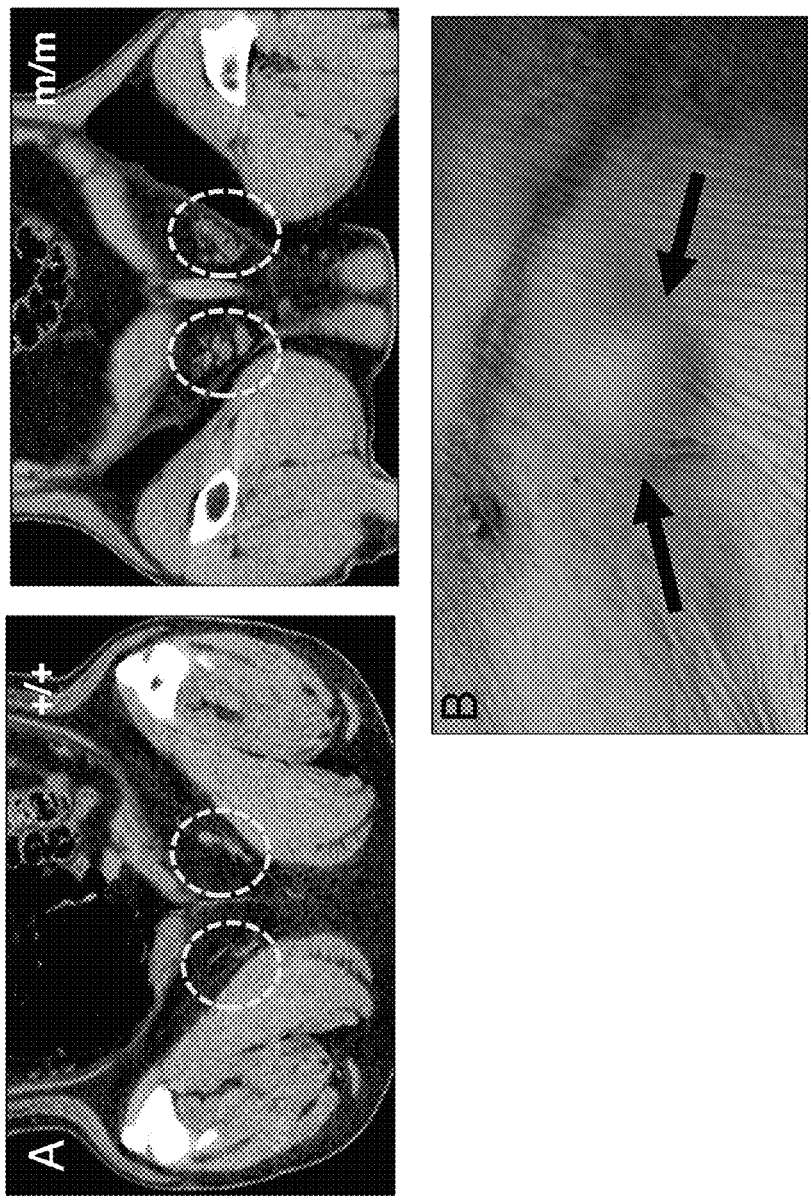
FIG. 13 shows lymphoma in TP53$^{R167H/R167H}$ pigs. Early stage enlargement in inguinal lymph nodes were detected.
Figure 13:
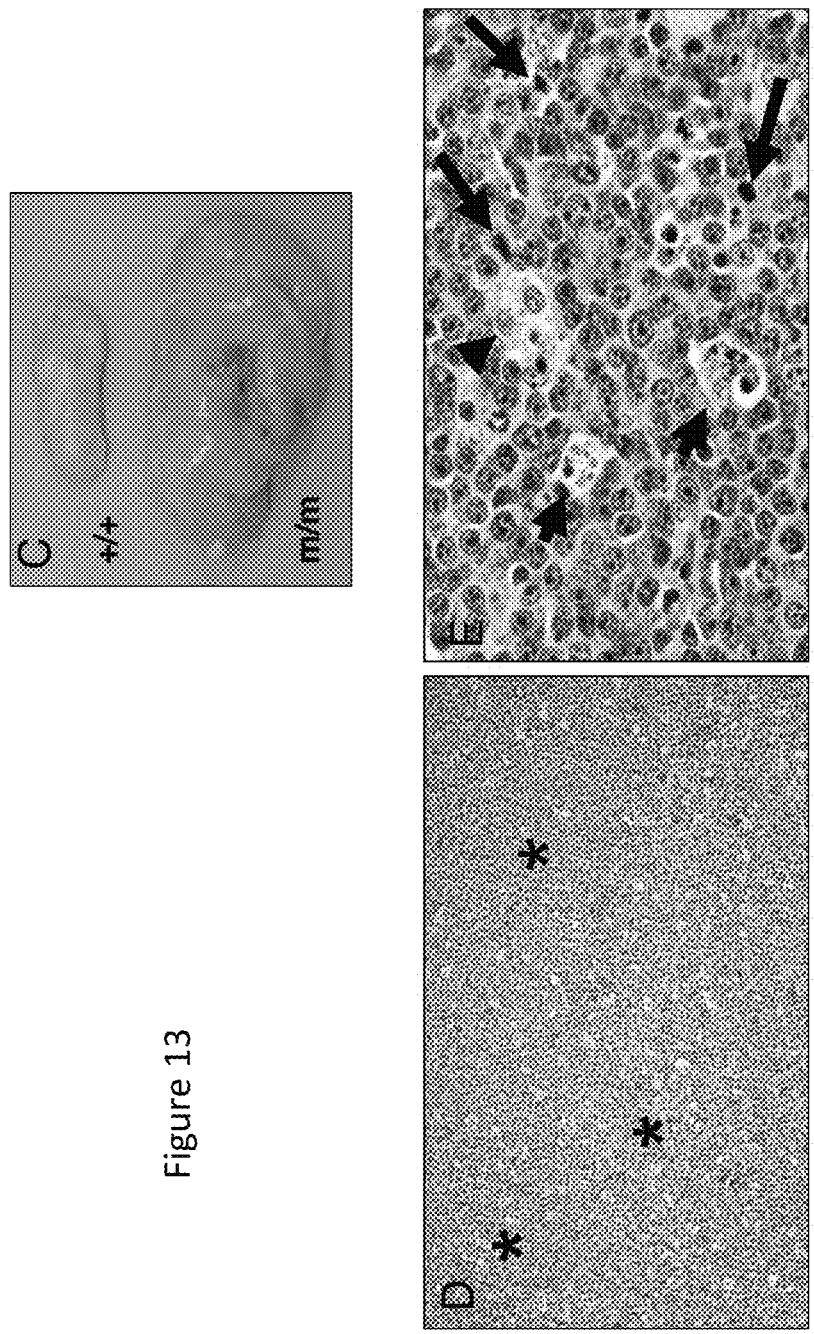
Figure 14:
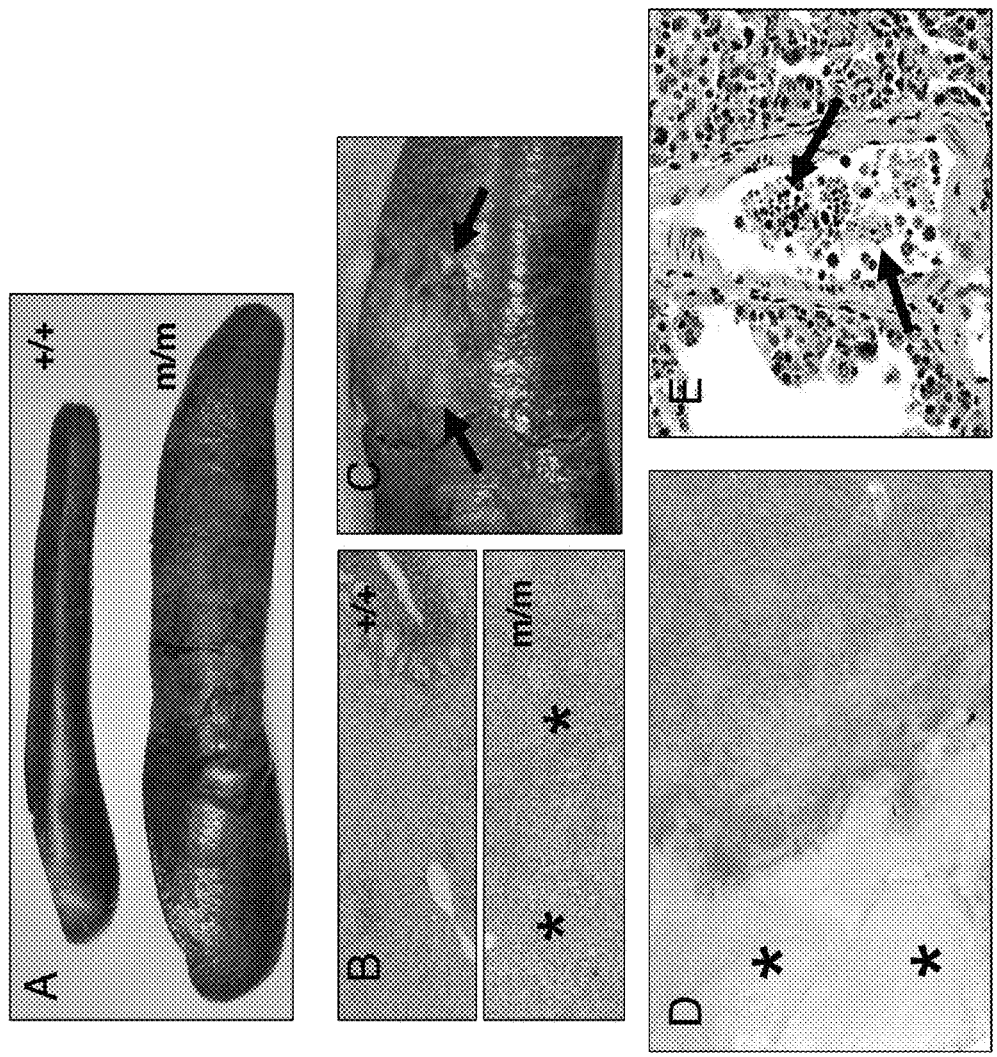
FIG. 14 shows lymphoma in TP53$^{R167H/R167H}$ pigs (m/m).
Figure 14:
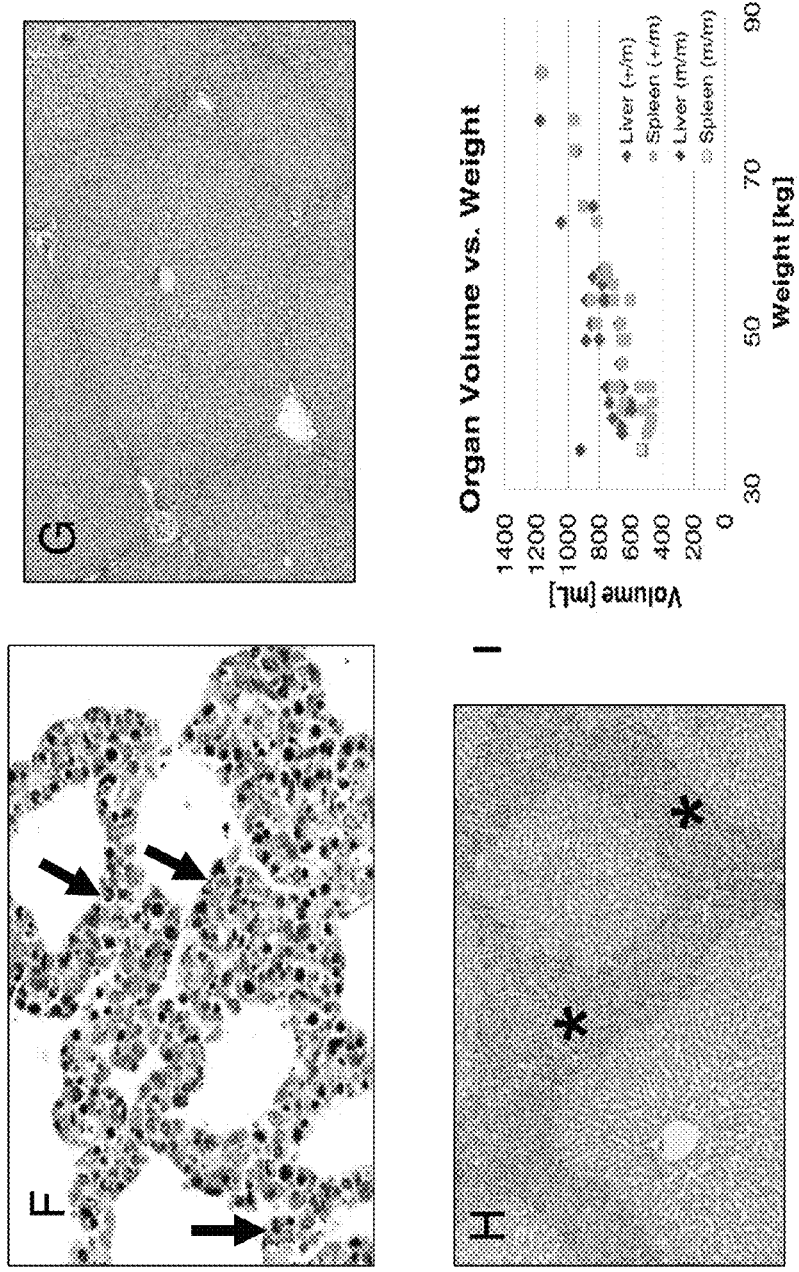

Three cases of lymphoma in the TP53$^{R167H/R167H}$ cohort were identified and confirmed histopathologically, with necropsy occurring over a range of 27 to 43 weeks of age (Cases 2-4). In-vivo CT and MRI data collected for Case 4 showed lymphadenopathy consistent with lymphoma 16 weeks prior to necropsy (27 weeks of age) (FIG. 13). Enlargement of the liver and spleen are both indicators of possible diffuse infiltration of the liver with lymphoma so further examination of these organs was performed. See Lee, W. K., et al. AJR. American journal of roentgenology 191:198-206 (2008); Leite, N. P., et al., Radiographics: a review publication of the Radiological Society of North America, Inc 27:1613-1634 (2007). The volume of the liver in Case 4 was assessed by CT and found to be much larger in the TP53$^{R167H/R167H}$ pig than its weight-matched TP53$^{R167H/+}$ control pig (923 ml vs. 659 ml, respectively) (FIG. 14I). The liver volume to animal weight ratio in the TP53$^{R167H/R167H}$ pig (Case 4) was also larger compared to the liver to animal weight ratio in a TP53$^{R167H/+}$ cohort (26.4 ml/kg vs. 15.6 ml/kg respectively). A mild elevation in quantitative CT determined spleen volume was noted in the TP53$^{R167H/R167H}$ lymphoma case when compared to the weight matched TP53$^{R167H/+}$ pig (532 ml vs. 486 ml respectively) and evidence of spleen enlargement was also reflected in the corresponding values of the spleen volume to animal weight ratio for the TP53$^{R167H/R167H}$ lymphoma case compared to the TP53$^{R167H/+}$ cohort (15.2 ml/kg vs. 13.5 ml/kg respectively) (FIG. 14I).

TABLE 5

Case numbers, age, clinical and pathological features of necropsied pigs.

| Case | Age | Clinical signs | Lesions |
|---|---|---|---|
| 1 TP53$^{R167H/R167H}$ | 2 hours | Perinatal death | Liver: Hepatocellular atypia |
| 2 TP53$^{R167H/R167H}$ | 6.75 months | Sudden death | Lymphoma Tumor lysis syndrome |
| 3 TP53$^{R167H/R167H}$ | 7.75 months | Loss of body condition, weight loss | Lymphoma |
| 4 TP53$^{R167H/R167H}$ | 10.75 months | Progressive lethargy, anorexia, weight loss, and reduced mobility in the 3-4 weeks prior to necropsy | Lymphoma |
| 5 TP53$^{R167H/R167H}$ | 12.5 months | Listless and hyporesponsive to external stimuli at time of euthanasia | Osteogenic tumors |
| 6 TP53$^{R167H/R167H}$ | 15.25 months | None | Osteogenic tumors Renal tumor (Wilms tumor/Nephroblastoma) |
| 7 TP53$^{+/R167H}$ | 7.75 months | None | None |
| 8 TP53$^{+/R167H}$ | 18.25 months | None | None |
| 9 TP53$^{+/+}$ | 7.75 months | None | None |
| 10 TP53$^{+/+}$ | 14.5 months | None | None |

All TP53$^{R167H/R167H}$ pigs that reached sexual maturity developed neoplastic lesions including lymphomas, osteogenic tumors, and a renal tumor. However, one pig (Case 1)

Elevated levels of contrast enhancement and delayed contrast clearance in both the liver and spleen were observed in the 3D fast gradient echo gadolinium enhanced MRI imaging study of the liver and spleen. Further, quantitative assessment of the contrast enhanced MRI study was performed comparing the liver to muscle MRI signal ratio and the spleen to muscle MRI signal ratio. The liver-to muscle ratio (1.13 vs. 0.89 respectively) and spleen-to-muscle ratio (1.02 vs. 0.95 respectively) were both increased in the TP53$^{R167H/R167H}$ lymphoma case compared to the weight matched TP53$^{R167H/+}$ pig. Heterogeneity in signal enhancement in the organs in the TP53$^{R167H/R167H}$ lymphoma case with respect to a weight matched TP53$^{R167H/+}$ pig is reflected through calculation of the coefficient of variation in signal intensity in the spleen (27% vs. 14% respectively) and liver (15% vs. 10%). Heterogeneous organ perfusion and delayed clearance of contrast media in the TP53$^{R167H/R167H}$ pig supported an imaging diagnosis of lymphoma.

Figure 15:
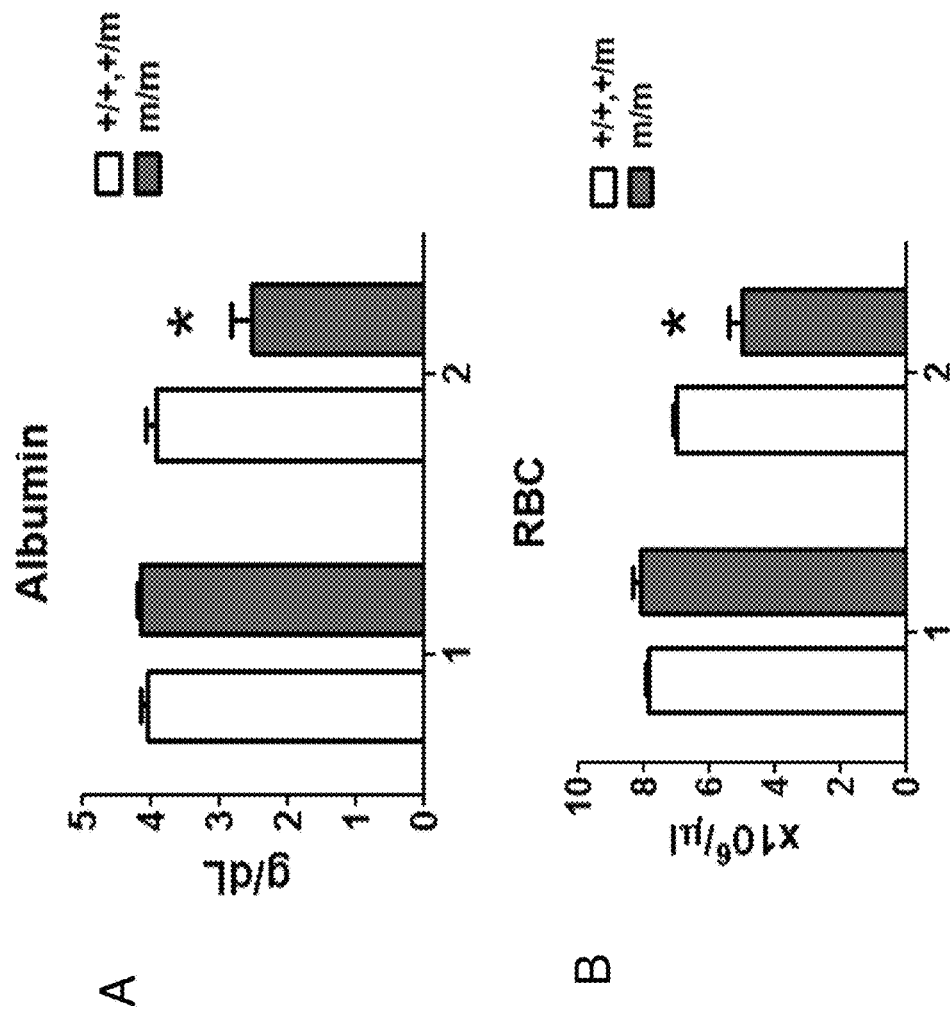
FIG. 15 reflects peripheral blood parameters from non-diseased control (+/+,+/m), Cases 7, 9, 10) and lymphoma cases in TP53$^{R167H/R167H}$ pigs (m/m, Cases 2-4) at time periods ~4-6 weeks prior to (1) and the week of (2) euthanasia/death. TP53$^{R167H/R167H}$ pigs were similar to non-diseased controls at time period 1, but had significant decreases in albumin (FIG. 15A, P<0.001), red blood cells (FIG. 15B, P<0.001) and platelets (FIG. 15C, P<0.05) compared to controls at time period 2. Lymphocyte counts (FIG. 15D) were similar to controls at time period 1, but by time point 2 there was a nonsignificant (P>0.05) trend toward increased numbers. Statistical analysis was performed with Two-Way ANOVA (repeated measures) with Bonferroni post-test.
Figure 15:
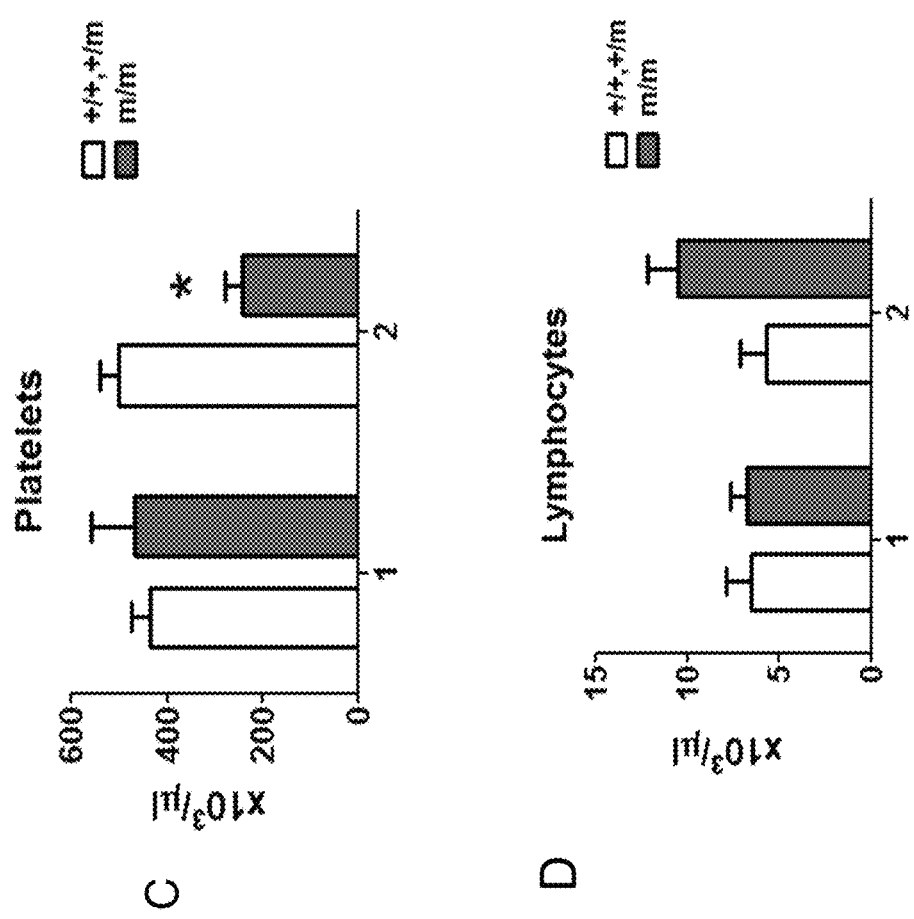

At necropsy, enlargement of the lymph nodes and spleen were prominent and consistent features in affected TP53$^{R167H/R167H}$ pigs (FIG. 13B-E, FIG. 14A, 14B). Microscopically, sheets of neoplastic lymphocytes effaced tissue architecture in these organs (FIG. 13D, 13E, 14B) with extension into liver and lung (FIG. 14E-H). In Case 2, the animal died suddenly and had hemo-abdomen secondary to splenic rupture (FIG. 14C, 14D). The lungs (and other organs) had vessels filled with abundant cellular and nuclear debris (FIG. 14E, 14F) that is consistent with tumor lysis syndrome, seen in many models (see, e.g., Treuting, P. M., et al., *Toxicologic pathology* 38:476-485 (2010); Vogel, P., et al., *Veterinary pathology* 47:719-724 (2010)) and in humans undergoing cytolytic cancer therapy (see, e.g., McBride, A., et al., *Journal of hematology & oncology* 5:75 (2012); Schifter, T., et al., *American journal of hematology* 60:75-76 (1999)). All three TP53$^{R167H/R167H}$ lymphoma cases had changes in selected peripheral blood parameters in the final days prior to necropsy, relative to control animals (FIG. 15). Interestingly, a routine blood sample collected two days prior to necropsy did not distinguish Case 2 from the other lymphoma cases (Cases 3 and 4) suggesting that the tumor lysis syndrome was associated with acute splenic rupture as opposed to tumor burden.

Figure 16:
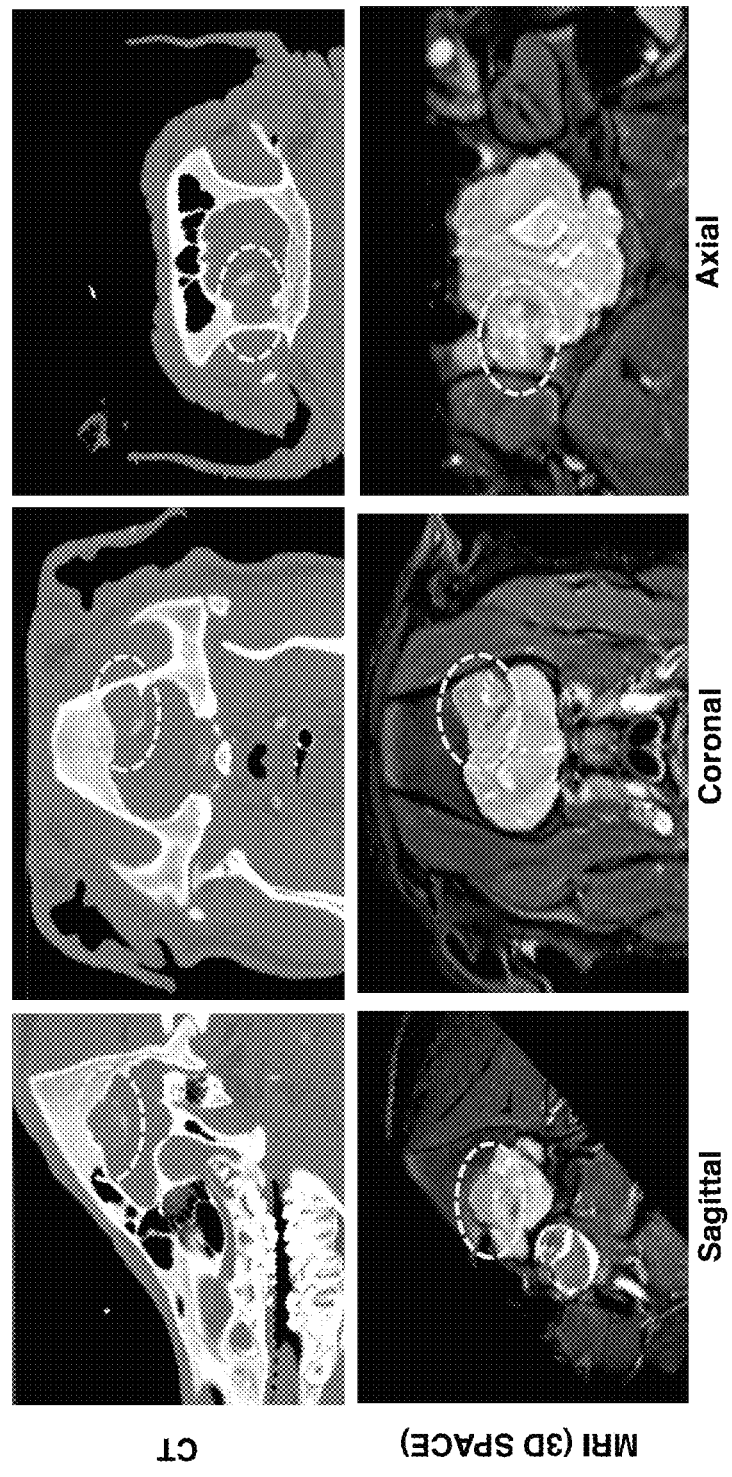
FIG. 16 shows an osteogenic tumor in a TP53$^{R167H/R167H}$ pig (Case 5).
Figure 16:
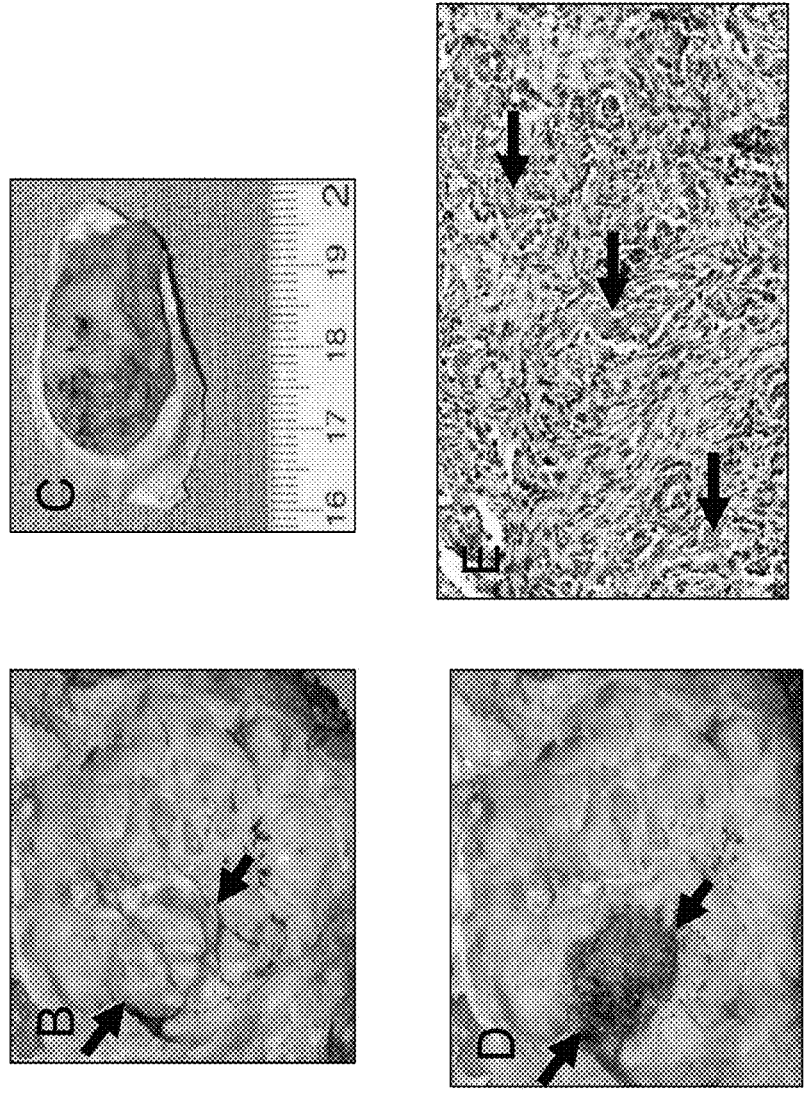
Figure 17:
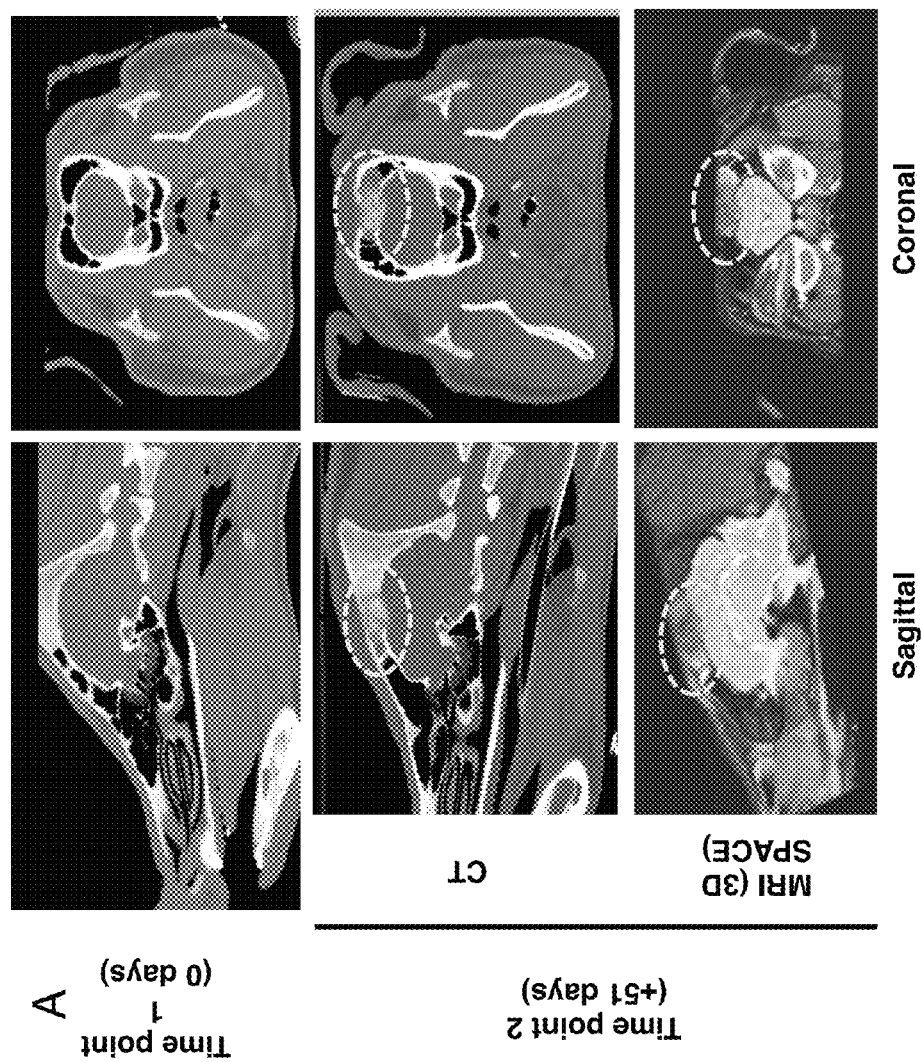
FIG. 17 shows an osteogenic tumor a in a TP53$^{R167H/R167H}$ pig (Case 6). In-vivo imaging with computed tomography (CT), showing coronal and sagittal cross-sectional views. Views from imaging time point 1 (FIG. 17A) show no evidence of tumor lesion, views from imaging time point 2 in CT and Magnetic Resonance Imaging (MRI) (51 days later) reveal aggressive tumor growth (39 mm).
Figure 17:
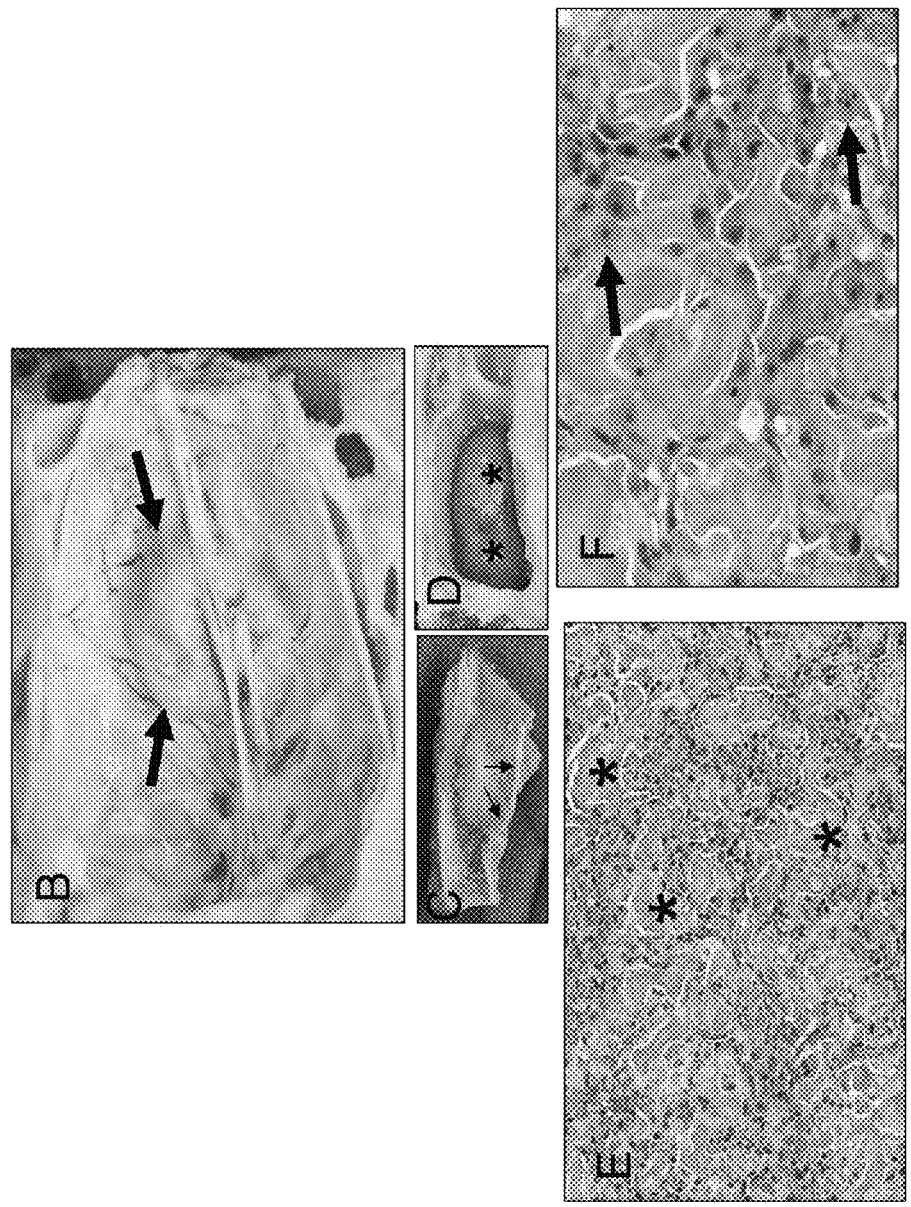
Figure 18:
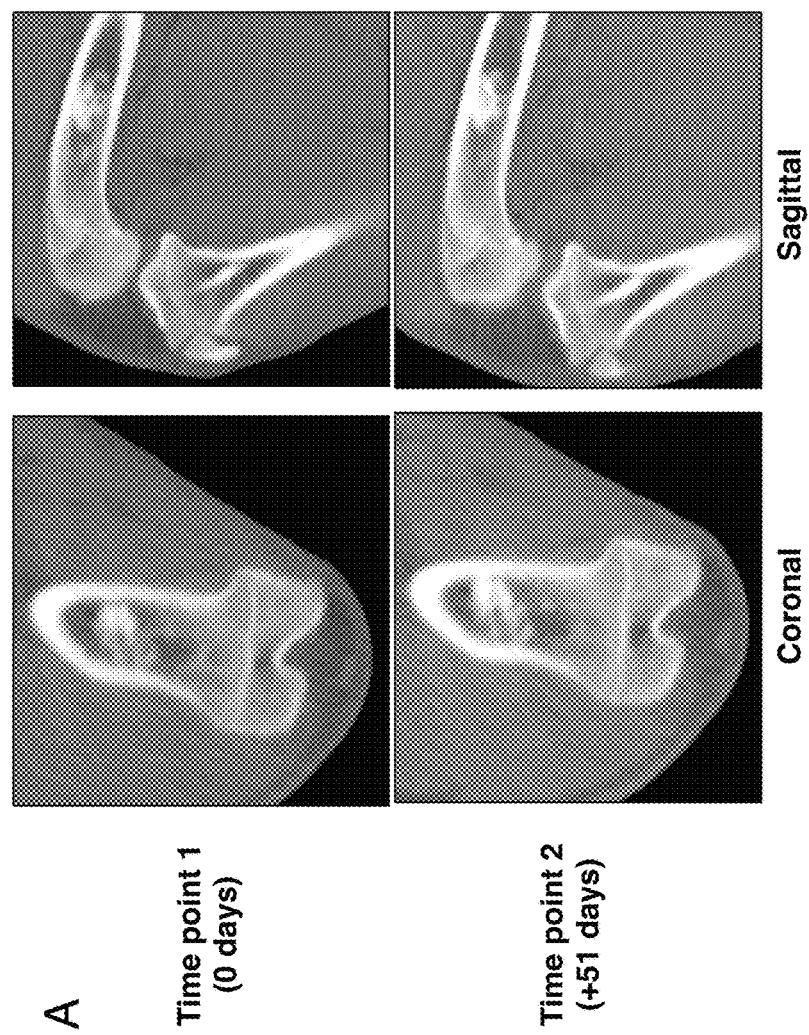
FIG. 18 shows an osteogenic tumor in a TP53$^{R167H/R167H}$ pig.
Figure 18:
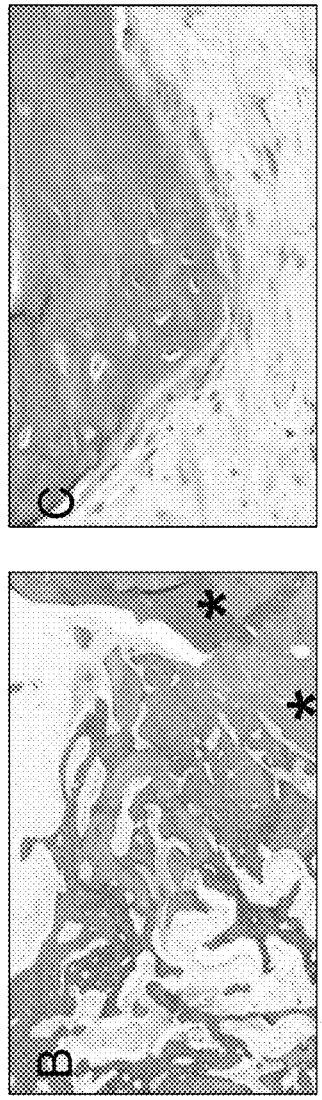
Figure 19:
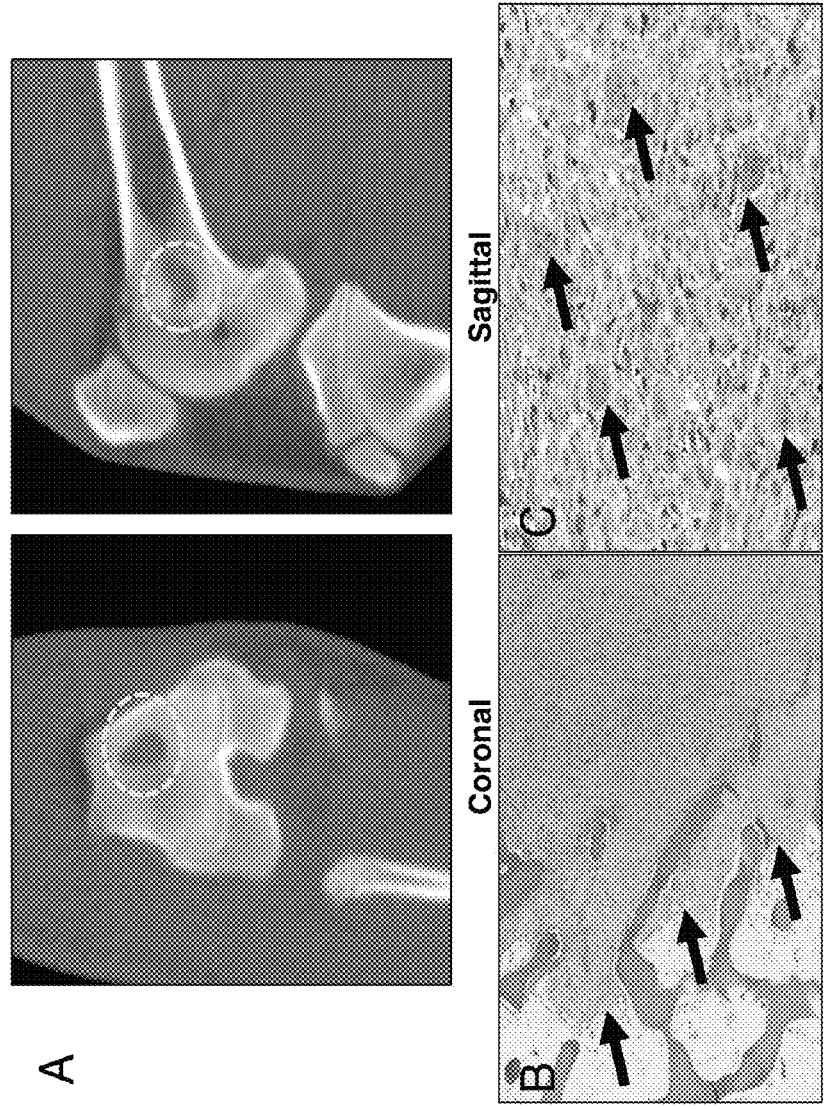
FIG. 19 shows an osteogenic tumor in a TP53$^{R167H/R167H}$ pig

Osteogenic tumors were also identified through in-vivo imaging in two TP53$^{R167H/R167H}$ pigs (Cases 5 and 6). CT and MRI detected a 28 mm right parasagittal, calvarial lytic (137 HU) tumor in Case 5 at 53 weeks of age. The tumor expanded into the intracranial cavity and also caused destruction of adjacent bone tissue (FIG. 16). In-vivo CT and MRI data collection was completed for Case 6 at two time points. At 53 weeks of age osteogenic tumors in the long bones were detected but no skull/calvarial tumor was present (FIG. 17A, time point 1). At 60 weeks of age, 51 days later, a 39 mm intracranial tumor was detected (FIG. 17A, time point 2). The tumor infiltrated through the bony calvarium to invade both the frontal sinuses and the intracranial compartment with evidence of extrinsic compression of the brain parenchyma. The tumor contained bony matrix as indicated by the increased CT attenuation (305 HU). This was supported by the heterogeneous signal enhancement present in the SPACE MRI data for both Case 5 and Case 6 calvarial tumors, indicating areas of both soft tissue and calcification/ossification. Microscopically, the two calvarial tumors were composed of spindled to epitheloid cells that produced osteoid trabeculae (FIGS. 16 and 17). Both tumors had invasion and one infiltrated into the frontal sinus(es) (FIG. 17A-17D). The sum of the imaging, histological and biological features were consistent with osteosarcoma.

The microscopic lesions in the calvarial tumors were similar in appearance, whereas the other osteogenic tumors in these animals had a varied microscopic appearance, even within the same pig. These changes ranged from osteoid/bone rich to osteoid poor lesions with proliferative mesenchymal cells (FIGS. 18, 19, 20 and 21). These other osteogenic tumors were located in the tibia, femur, and sacrum, ranging in size from 8 mm-18 mm (Table 6, Case 5 and 6). Lytic lesions presented with mean CT attenuations between 87 and 156 HU. Heterogeneous and hyper-dense lesions ranged in mean CT attenuation from 307 to 927 HU. The osteogenic tumors in the long bones of Case 6 were all present at time point 1, prior to development of the calvarial tumor. No significant change in tumor size was detected for any of the osteogenic tumors of the long bones while some subtle changes in CT attenuation were observed, such as the increased solid component of the tumor in FIG. 18. Importantly, no osteogenic tumors were seen in long bones of the pigs without osteosarcoma tumors (littermate TP53$^{R167H/R167H}$ pigs, TP53$^{R167H/+}$ pigs, TP53$^{+/+}$ pigs).

In one of the TP53$^{R167H/R167H}$ pigs with osteogenic tumors (Case 6), a renal tumor was also detected via CT and MRI imaging (FIG. 22A-22D). The tumor (25.8 mm and 8.9 ml) was located in the right cranial pole of the kidney with an accompanying focus of hemorrhage (23.4 ml) at time point 1. Image data of the tumor 51 days later (60 weeks of age, time point 2) showed nominal changes in tumor size (26.3 mm and 7.1 ml), but had obvious resolution of the hemorrhage component. Contrast enhanced CT attenuation of the tumor decreased from time point 1 to 2 (62 HU to 55 HU respectively), reflecting an increase in necrotic tissue component, which was supported by histopathology findings (FIG. 22 E, 22F).

Signal intensity in the tumor relative to the unaffected renal cortex was assessed within the MRI data. Pre-contrast, T1-weighted (VIBE) MRI data revealed a shift from time point 1 to time point 2 from isointense to hypointense signal relative to the renal cortex. The hemorrhage in time point 1 was clearly evident as a hyperintense component. Post-contrast, T1-weighted (VIBE) MRI demonstrated a heterogeneous enhancement at time point 1 and a decrease in signal intensity relative to the renal cortex at time point 2. The resolution of the hemorrhage component and increase in necrosis between the time points is likely responsible for the relative decrease in signal intensity in the follow up post-contrast MRI data.

Figure 22:
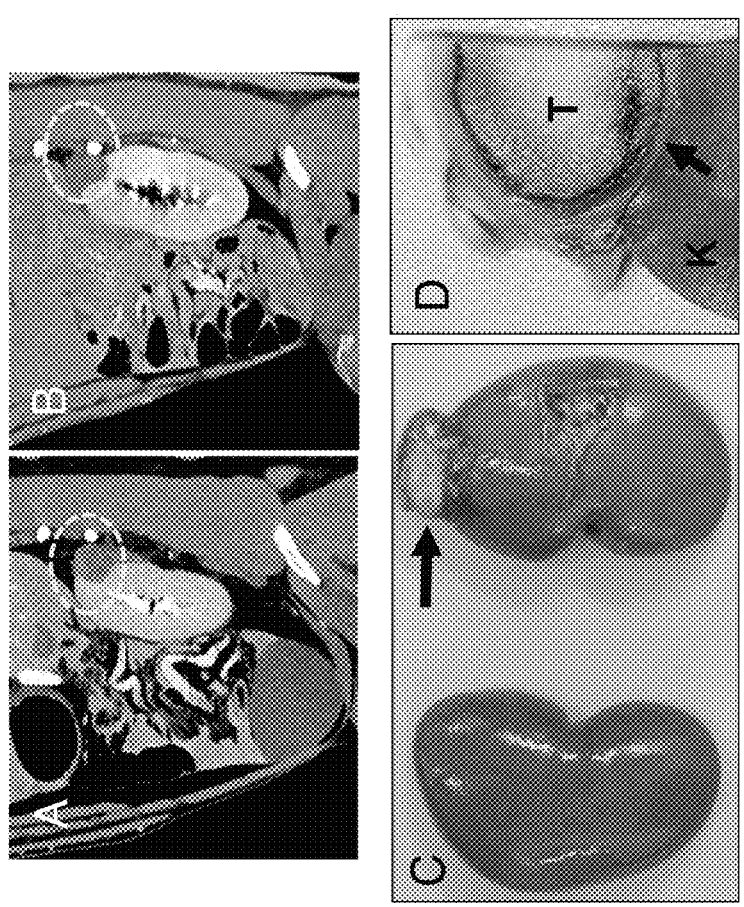
FIG. 22 shows a renal tumor in a TP53$^{R167H/R167H}$ pig (Case 5). Change in renal tumor size over time was assessed with iodinated contrast enhanced computed tomography at time point 1 (FIG. 22A) and 51 days later at time point 2 (FIG. 22B), sagittal view shown.
Figure 22:
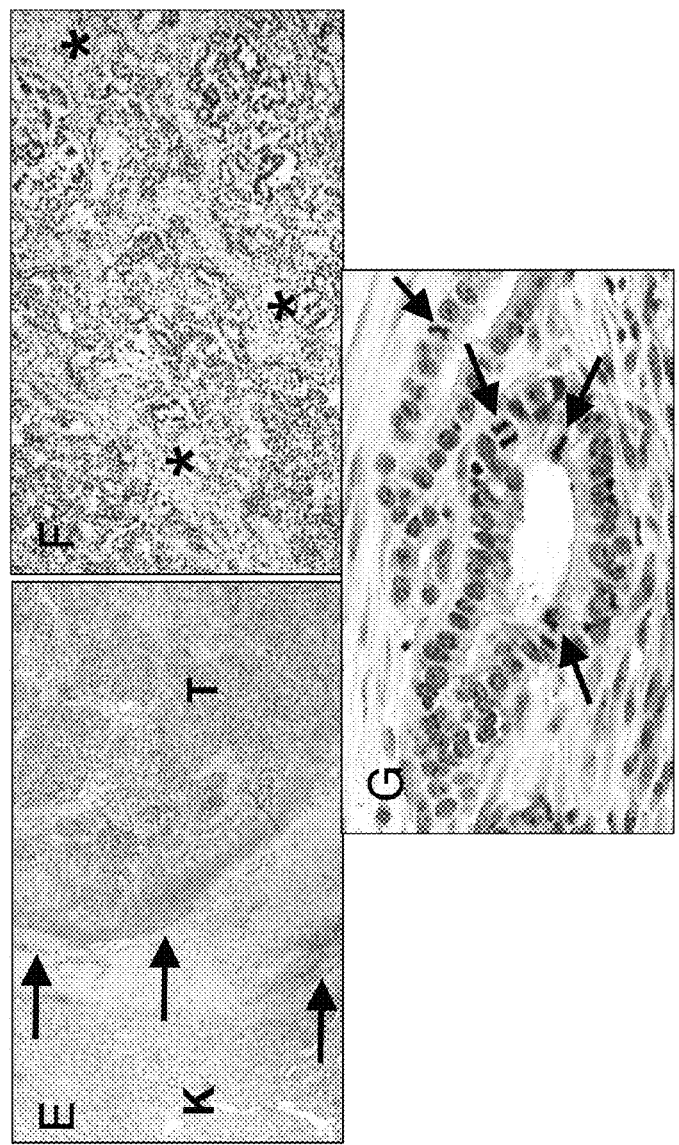

Microscopically, the renal tumor was composed of necrotic tubules and intervening cords of connective tissue and foci of hemorrhage (FIG. 22 E, 22F). Within and extending through the tumor capsule were small invading nests of poorly differentiated tubules that had a high mitotic rate (FIG. 22E, 22G). The imaging and pathologic findings were consistent with a Wilms tumor (nephroblastoma), a malignancy commonly associated with p53 pathway perturbations in which TP53 mutation correlates with a less favorable prognosis. See Gylys-Morin, V., et al., *Radiology* 188:517-521 (1993); Stanhope-Baker, P., et al., *The Journal of biological chemistry* 279:33575-33585 (2004); Ordonez, N., et al., *Rosai and Ackeman's Surgical Pathology*. J. Rosai, editor. New York: Mosby (2004).

Figure 21:
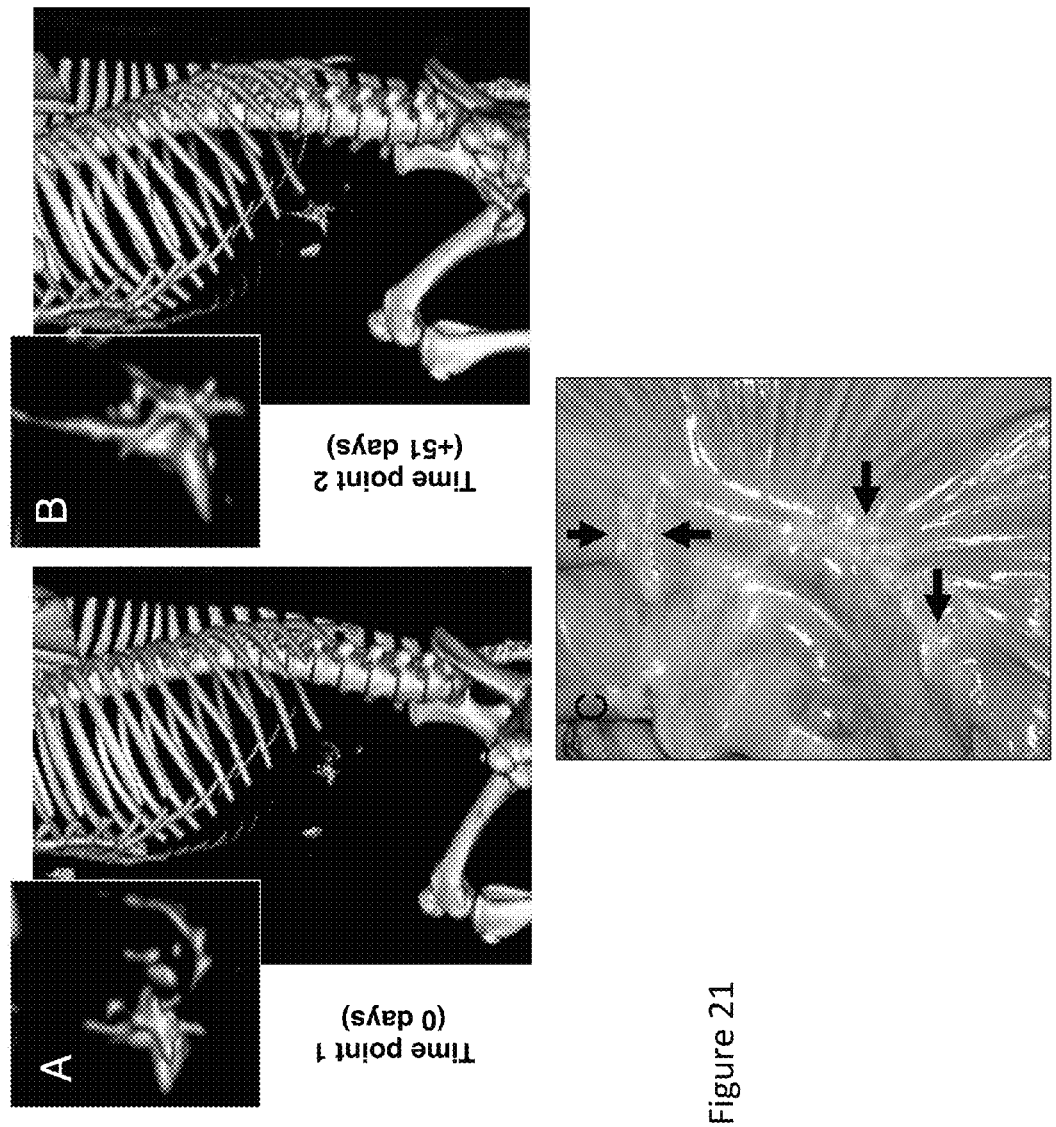
FIG. 21 shows a mesenteric lesion in a TP53$^{R167H/R167H}$ pig (Case 6).
Figure 21:
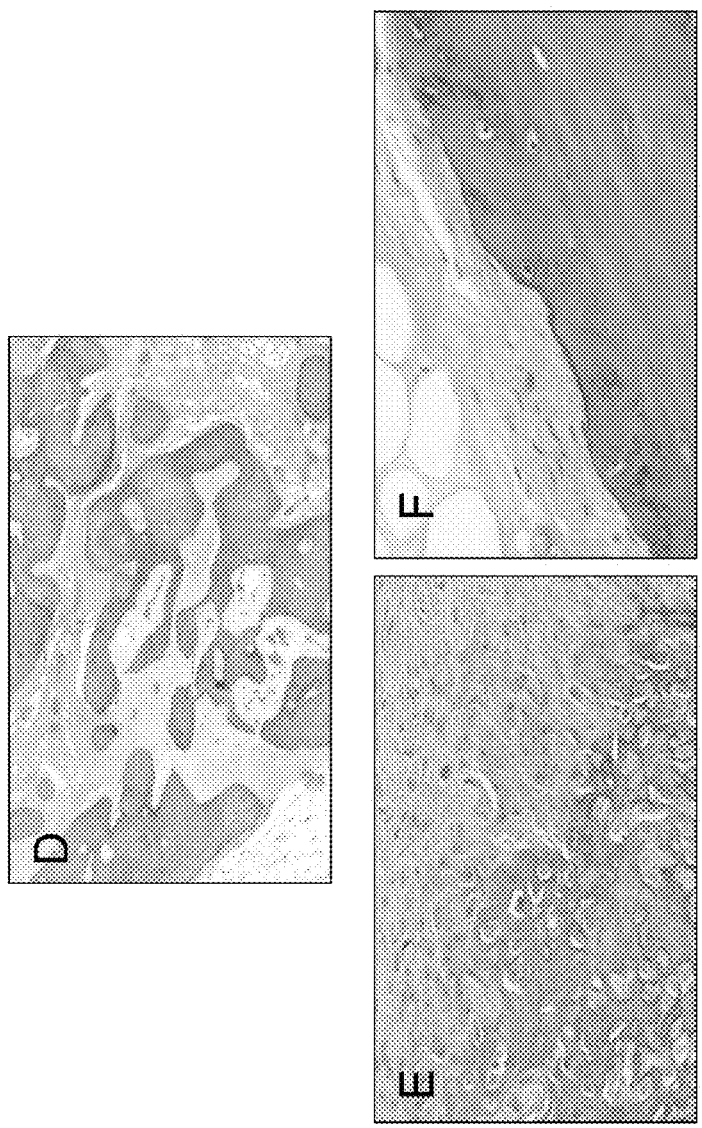

In addition, a mesenteric tumor was detected for Case 6 (FIG. 21). The tumor shape was highly irregular and 78 peculated, with high mean CT attenuation (472 HU) compared to the surrounding soft tissues (30-50 HU) (FIG. 21C). A significant growth in tumor volume from 2.07 ml to 3.08 ml (48% increase) was measured from imaging time point 1 to time point 2 (51 days later), with minimal change in mean CT attenuation (+2 HU) (FIG. 21A, 21B). At necropsy, the irregularly shaped bony tumor was located within the mesentery. The location of the bony mesenteric tumor was near the site of hemorrhage from the renal tumor (FIG. 22); this and its general appearance were consistent with mesenteric myositis ossificans (see Table 2).

Example 7

Molecular Genetic Analyses of TP53$^{R167H/R167H}$ Tumors

Figure 23:
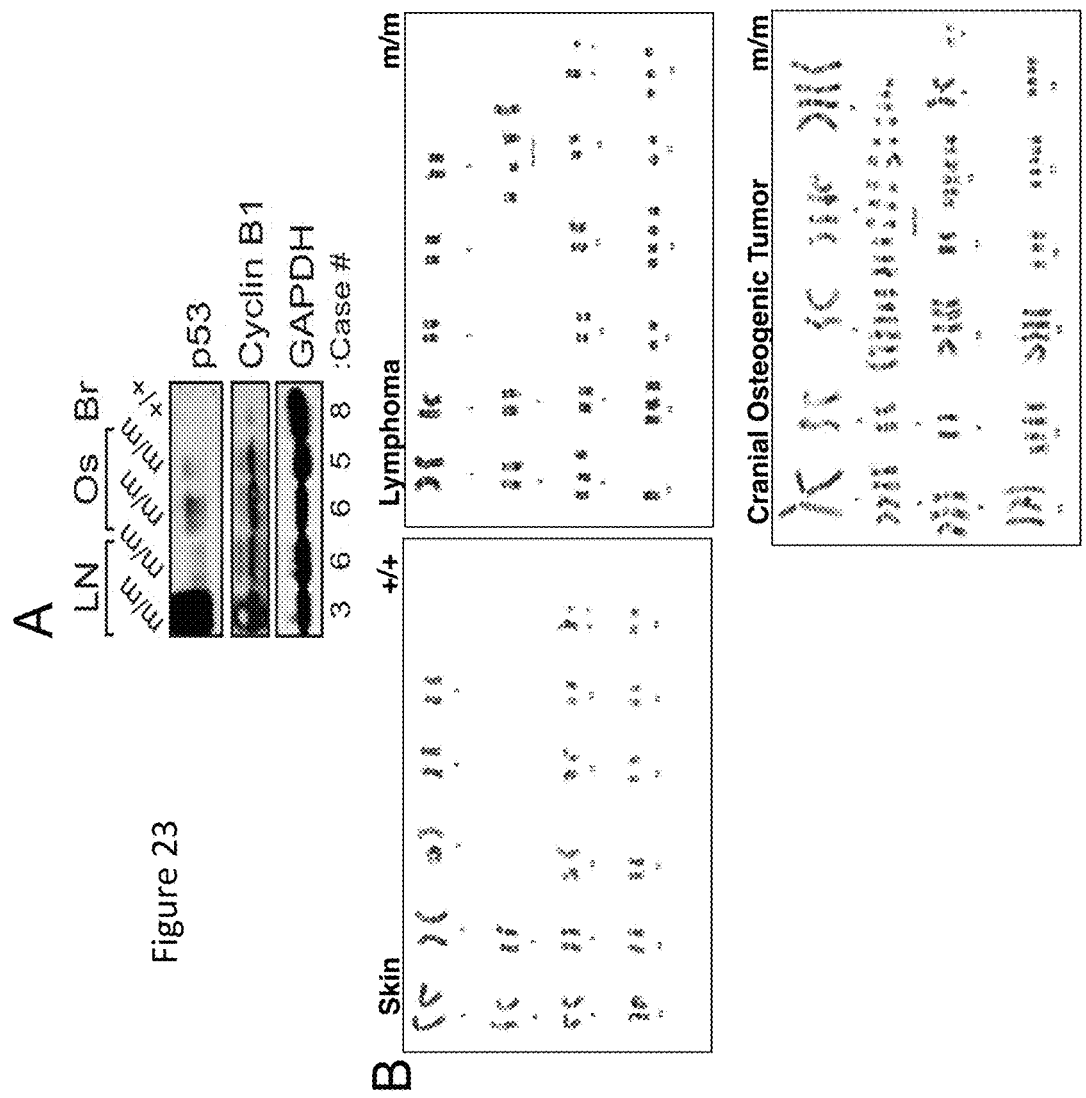
FIG. 23 shows molecular changes and cytogenetic abnormalities in TP53$^{R167H/R167H}$ pig tumors.

Several excised lymph nodes and osteogenic tumors were subjected to western blot analyses to confirm p53-R167H mutant protein expression and activity. Compared to the essentially undetectable expression of non-mutated p53 from wild-type pig brain tissue, mutant p53-R167H protein was expressed at higher levels in each malignant sample (FIG. 23A), as anticipated. The porcine p53-R167H mutation, like its human (R175H) and mouse (R172H) counterparts, is expected to behave as a "gain-of-function" mutant that fails to regulate normal p53 transcriptional targets (such as p21, see FIG. 24) and instead transactivates a new set of oncogenic gene targets, including cyclin B1. See Freed-Pastor, W. A., et al., *Genes & Development* 26:1268-1286 (2012); Brachova, P., et al., *International Journal of Molecular Sciences* 14:19257-19275 (2013). Indeed, tumors and lymph nodes expressing p53-R167H showed marked upregulation of cyclin B1 protein (FIG. 23A). Human tumors expressing mutant p53 primarily sustain chromosomal alterations as opposed to genomic sequence mutations. See Ciriello, G., et al., *Nature Genetics* 45:1127-1133 (2013). We conducted cytogenetic analyses of metaphases from a lymph node and osteosarcoma isolated from TP53$^{R167H/R167H}$ pigs, which revealed significant abnormalities in both chromosome number and structure (FIG. 23B). By comparison, a normal karyotype was seen in the skin tissue of a wild-type pig control. These findings confirm the altered expression and activity of mutant p53-R167H in the TP53$^{R167H/R167H}$ tumors, as well as the characteristic chromosomal instability known to accompany p53 mutation in human tumors.

Example 8

Monitoring the Development of Cancer in Various TP-53 Targeted Pigs

TP53 pigs were created according to the methods described herein. Without intervention, these TP53-targeted pigs would be expected to develop a spectrum of tumors throughout the body, just as humans and mice with analogous TP53 mutations. When and where tumors would develop would be impossible to predict so phonotypical characterization was developed.

Heterozygotes. A longitudinal, non-invasive monitoring protocol was developed and implemented utilizing computed tomography (CT) and magnetic resonance imaging (MRI). The pigs were anesthetized, intubated, and mechanically ventilated for the duration of the study. Head, thorax and abdominal imaging protocols were performed with both modalities, including iodine contrast (2 cc/kg) enhanced CT and gadolinium contrast (0.1 mmol/kg) MRI imaging of the thorax and abdomen. Enforced breath-holds at 25 cm H$_2$O were utilized to eliminate respiratory motion. Seven TP53-heterozygote pigs were imaged at up to five time points throughout a year-long period (aged 1-2 years), allowing for the tracking of disease progression and the systematic comparison of CT and MR datasets for protocol optimization purposes. Structured reports were developed to provide an organized, systematic approach for guiding radiological assessment of the image data focusing on specified anato-

TABLE 6

Examples of imaging techniques linking to pathology findings in the TP53$^{R167H/R167H}$ pigs

Figure 20:
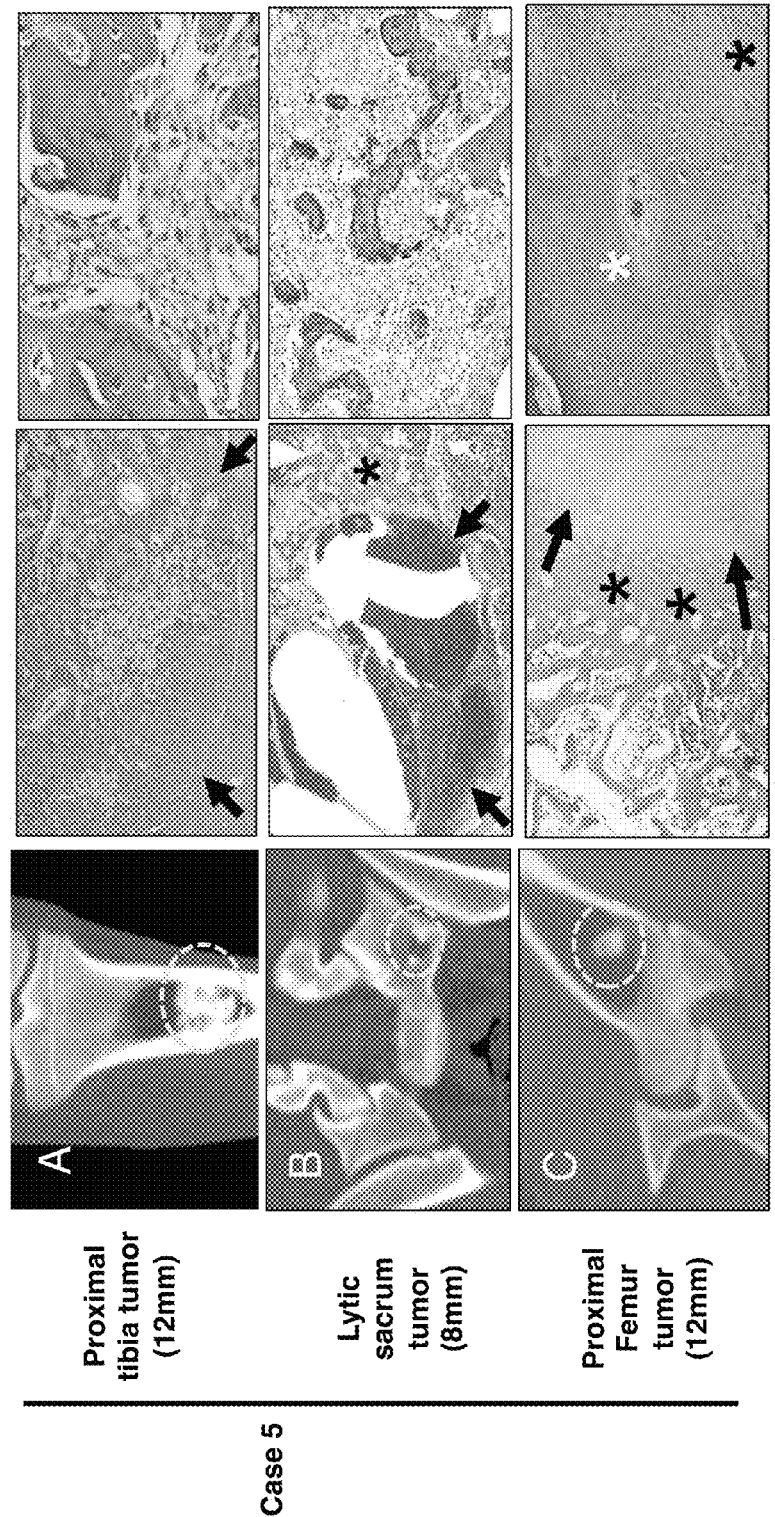
FIG. 20 shows examples of osteogenic tumors in the TP53$^{R167H/R167H}$ pigs.
Figure 20:
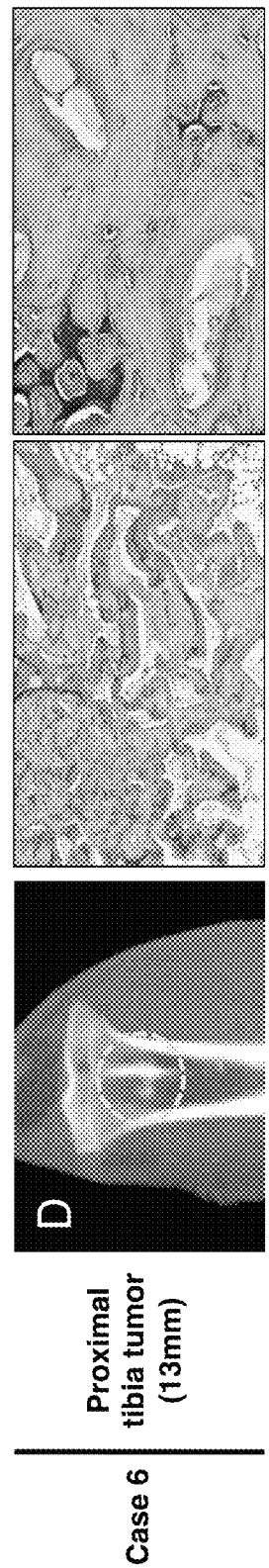

| Case | Site | Imaging | Pathology |
|---|---|---|---|
| Case 5 | Cranium ® | Right parasagittal lytic tumor (28 mm) | Extradural tumor composed of spindled to epitheloid cells that produced irregular trabeculae of osteoid. FIG. 16 |
| | Sacrum (L) | Left side, lytic tumor (8 mm) | Large blood-filled chamber partially surrounded by dense bone and by loose connective tissue with cartilaginous/osteoid production FIG. 20B |
| | Femur (L) | Distal metaphysis, lytic tumor (13 mm) | Solid sheets of tumor cells with scant osteoid production, but with numerous multinucleate osteoclast-like cells FIG. 19 |
| | Femur (L) | Proximal metaphysis, heterogeneous tumor (12 mm) | Dense osteoid/bone trabeculae extending from the edge of the cortex with a partial rim of osteosclerosis along periphery FIG. 20C |
| | Tibia ® | Diaphysis/metaphysis, hyper-dense tumor (12 mm) | The tumor was composed of coalescing bone trabeculae that effaced most of bone marrow to cortex FIG. 20A |
| Case 6 | Cranium ® | Intracranial tumor extending into frontal sinus (39 mm) | Extradural tumor composed of spindled to epitheloid cells that produced irregular trabeculae of osteoid FIG. 17 |
| | Femur (L) | Distal diaphysis/metaphysis, hyper-dense tumor (18 mm) | Spindled cells on collagenous to mineralized matrix with a peripheral rim of osteosclerosis FIG. 18 |
| | Tibia (L) | Proximal metaphysis, hyper-dense tumor (13 mm) | The tumor was composed of coalescing bone trabeculae lined by scattered loose connective tissue rare osteoblasts. FIG. 20 |
| | Kidney ® | Superior pole, Hypo-dense tumor (26 mm) | Diffuse coagulation necrosis with hemorrhage; tumor had numerous irregular tubules with interspersed bands of connective tissue; scattered nests of poorly differentiated tubules invaded through capsule. FIG. 22 |
| | Mesentery | Irregular hyper-dense tumor | Regional mesentery with irregular to elongate bony tumors composed of coalescing trabeculae of bone/osteoid; heterogeneity was seen with focal proliferations to mature bone line by low cellularity connective tissue. FIG. 21 | mies noted in the report. Through longitudinal imaging suspicious lung lesions were identified in two animals and a suspicious liver lesion in another pig. Additionally, enlarged lymph nodes were detected in six animals. Longitudinal assessment of these animals is continuing with imaging, blood-work, and clinical symptom development to track disease progression.

Homozygotes. The TP53-homozygote animals would be expected to develop tumors more rapidly and progress over a shorter timeline. Indeed, homozygote animals developed cancers, including lymphomas and osteosarcomas, in the first year of life (see Example 6). Lymphomas developed as early as 6.5 months of age, commonly with splenomegaly, lymphadenomegaly and hepatomegaly. In one case, the spleen ruptured with additional clinical features of tumor lysis syndrome and sudden death. In other cohorts, osteosarcoma was a repeated finding with intracranial and intramarrow masses readily detectable by imaging. These tumors match what would be expected in human Li-Fraumeni patients and mice bearing the orthologous R175H and R172H mutations, respectively, since both primarily develop lymphomas and osteosarcoma. See Olive K P, et al., Cell. 2004; 119(6):847-60 (doi: 10.1016/j.cell.2004.11.004. PubMed PMID: 15607980).

Taken together, the results seen in the TP53-targeted pigs validate the utility of pigs as models of human cancer.

Figure 24:
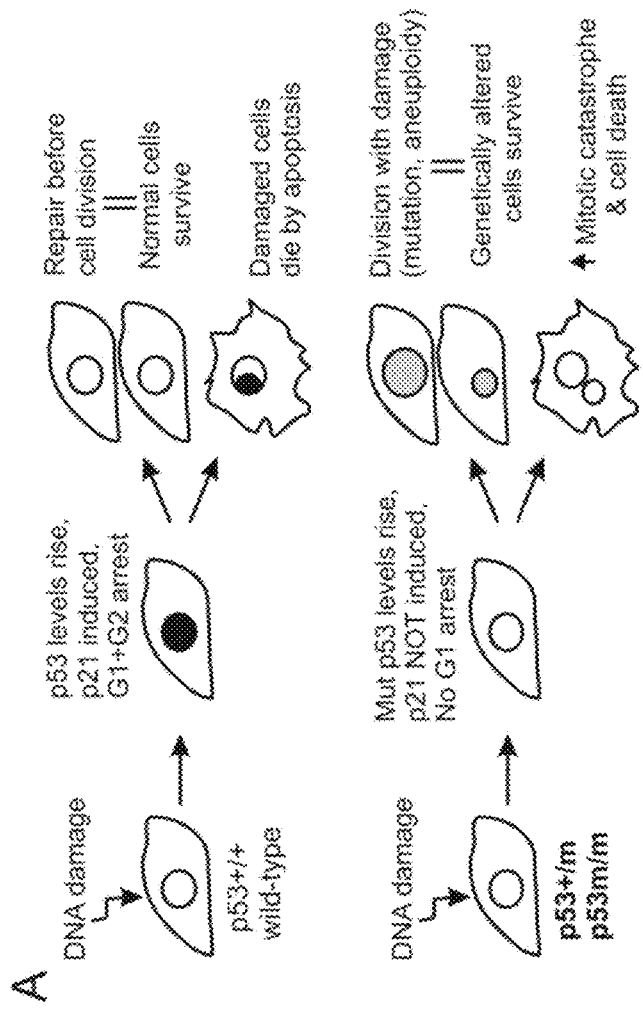
FIG. 24 shows defective molecular and biological activity of the porcine p53-R167H mutant protein.
Figure 24:
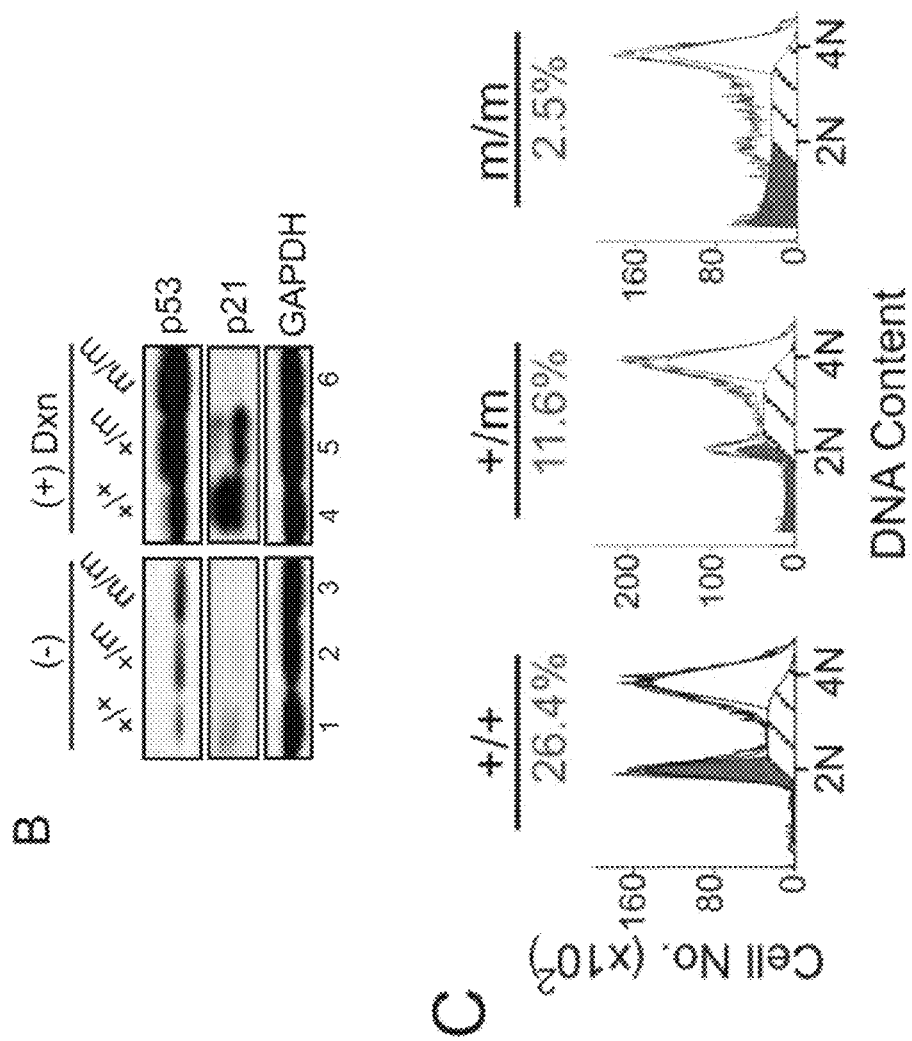
Figure 24:
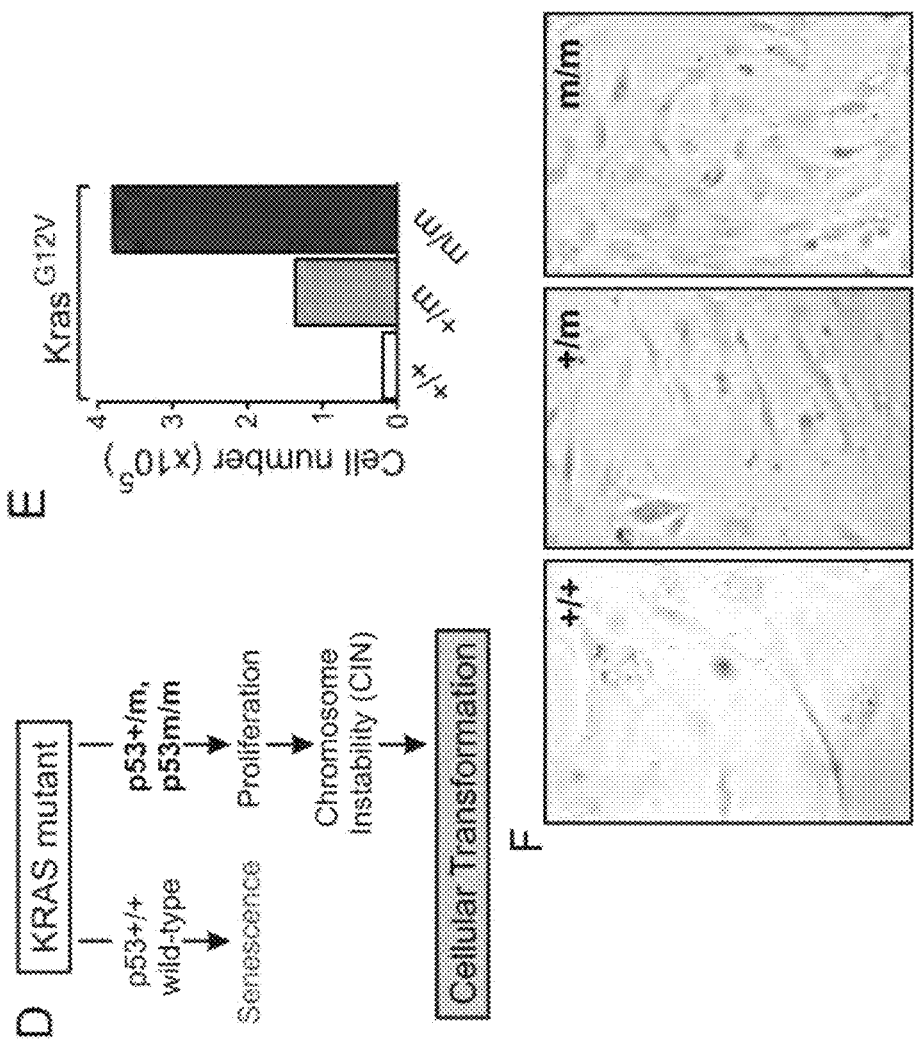
Figure 25:
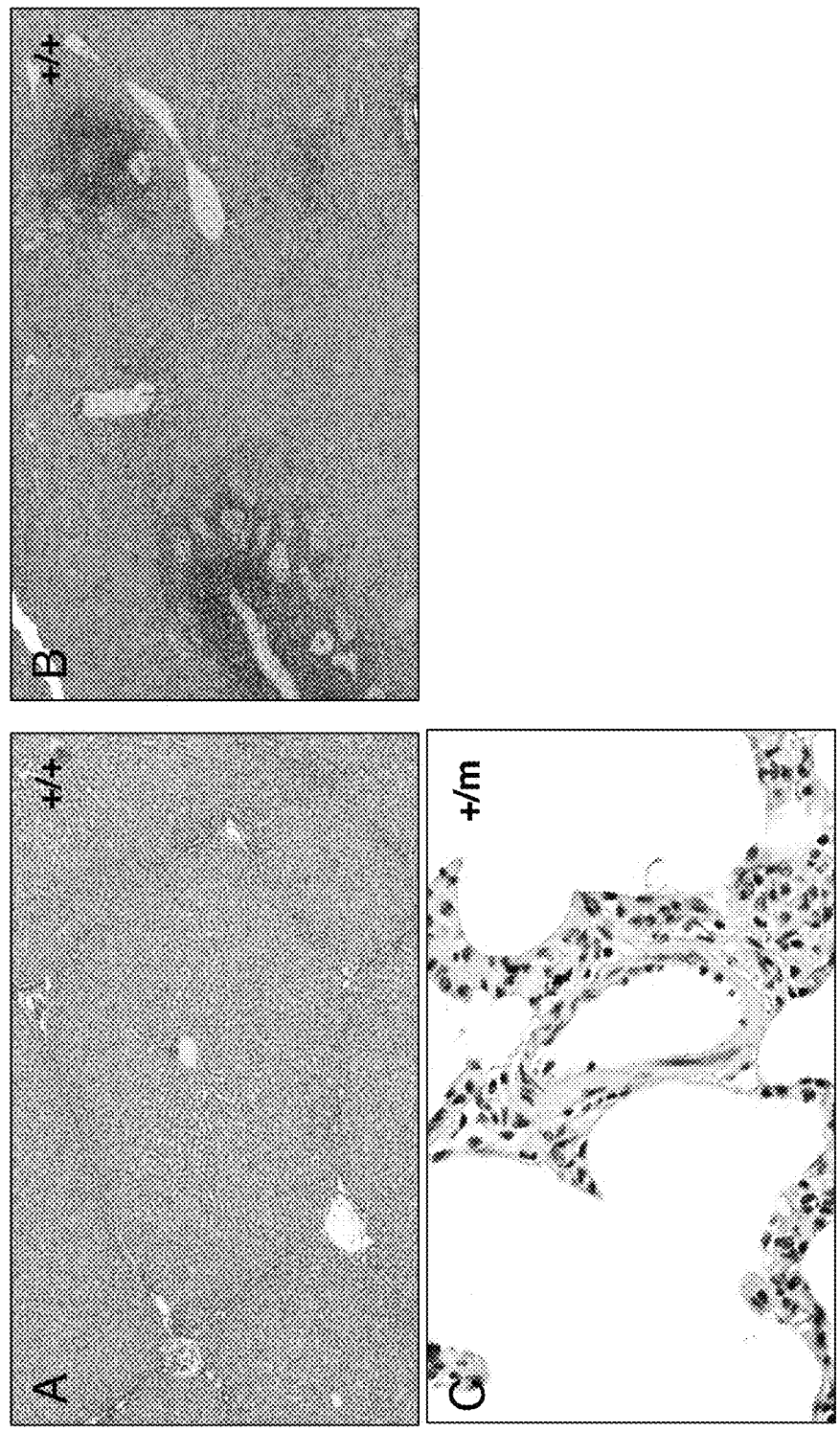
FIG. 25 shows examples of tumor free tissues in TP53$^{+/+}$ (FIGS. 25A, 25B, 25D, 25E) and TP53$^{+/R167H}$ (FIG. 25C) pigs. Liver (Case 9) (FIG. 25A), 40×. Spleen (Case 9) (FIG. 25B), 40×. Lung (Case 8) (FIG. 25C), 400×. Bone marrow (Case 10) (FIG. 25D), 40×. Lymph node (Case 9) (FIG. 25E), 40×.
Figure 25:
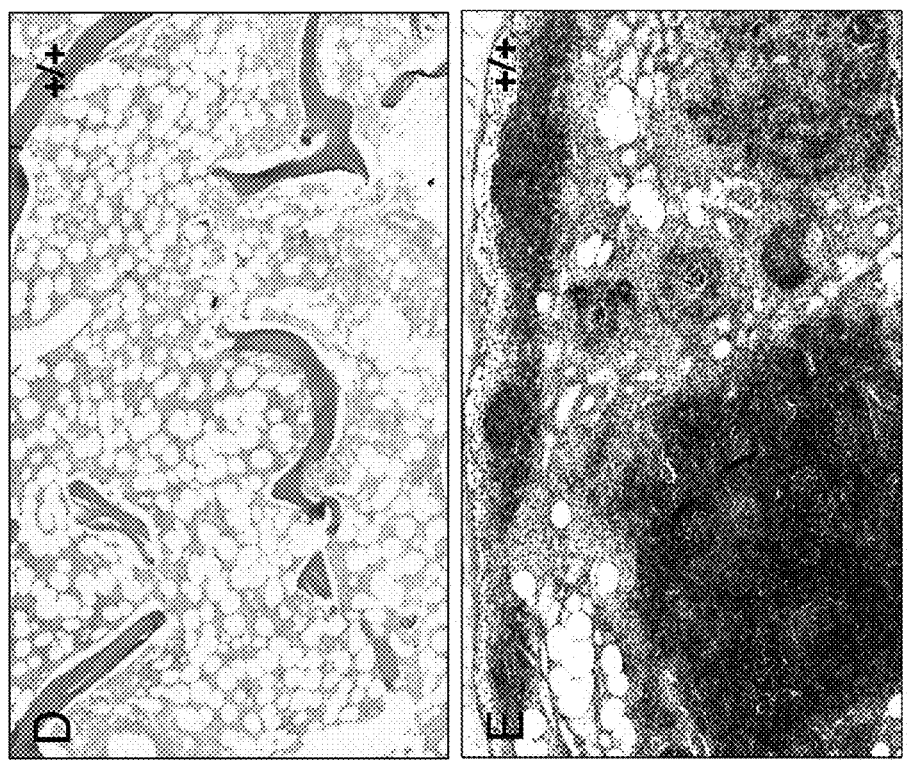

It is well established that dual mutation of TP53 and KRAS genes in humans are critical events for the initiation and progression of numerous deadly cancers, including adenocarcinomas of the lung and pancreas. See Bardeesy N, et al., Nature reviews Cancer. 2002; 2(12):897-909; Herbst R S, et al., N Engl J Med. 2008; 359(13):1367-80; Tuveson D A, et al., Oncogene. 1999; 18(38):5318-24; Jackson E L, et al., Cancer Res. 2005; 65(22):10280-8; Hingorani S R, et al., Cancer cell. 2005; 7(5):469-83. In normal cells expressing wild-type p53, the mutagenic activation of KRAS provokes a permanent p53-mediated cell cycle arrest (senescence) that protects cells from oncogenic transformation. In contrast, mutation of p53 impairs its regulation of growth inhibitory genes and allows cells to continue proliferating in the face of mutant KRAS expression. P53 is required for chromosome stability; thus, cells with mutated p53 and KRAS acquire genetic alterations that promote their neoplastic transformation and ultimately the development of tumors (see Fukasawa K., et al., Science. 1996; 271(5256): 1744-7; Sherr C J, et al., Cancer cell. 2002; 2(2):103-12). Consistent with those findings in mouse and human cells, pig fetal fibroblasts (PFFs) expressing one or two TP53$^{R167H}$ alleles effectively escaped mutant KRAS-induced senescence and continued to proliferate (FIG. 24). These data strongly predict that, similar to mouse tumor models, mutant KRAS$^{G12D}$ expression will accelerate tumorigenesis in heterozygous TP53$^{R167H/+}$ pigs.

Example 9

Generation of a Conditional KRAS Mutation in TP53$^{R167H/+}$ Cells

Figure 10:
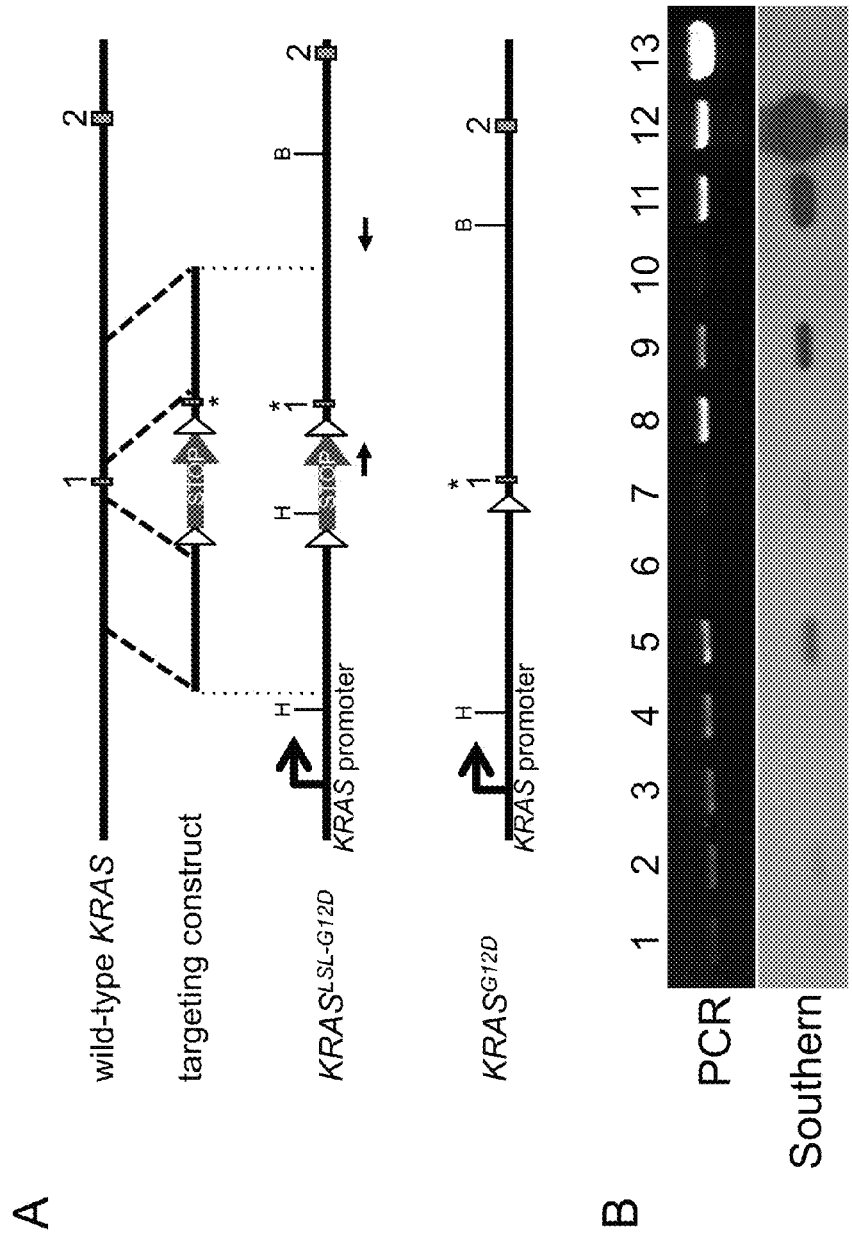
FIG. 10 is a schematic of the gene targeting strategy in one embodiment of the invention.

Homologous recombination is used to generate a conditional KRAS mutation in TP53$^{R167H/+}$ cells. The common G12D mutation was introduced in KRAS exon 1. KRAS$^{G12D}$ is an "activating" mutation resulting in constitutive GTPase activity and acts via a dominant mechanism of pathogenesis. See Schubbert S, et al., Nature reviews Cancer. 2007; 7(4):295-308 (doi: 10.1038/nrc2109. PubMed PMID: 17384584). In order to conditionally express KRAS$^{G12D}$, we also inserted a floxed transcription/translation termination cassette (i.e., a stop cassette) was also upstream of exon 1 (FIG. 10A). The stop cassette is intended to prevent expression of KRAS$^{G12D}$ from the targeted allele except in the presence of Cre-recombinase. See Tuveson D A, et al., Cancer cell. 2004; 5(4):375-87 (PubMed PMID: 15093544). The non-targeted allele is unaffected, as homozygous KRAS mutations result in embryonic lethality. This inducible system would allow for site-specific expression of the KRAS$^{G12D}$ allele in almost any tissue by delivering Cre with a virus or by crossing with a pig expressing Cre via a tissue-specific promoter. This method has been used successfully in the generation of KRAS/TP53-targeted mouse models. See Tuveson D A, et al., Cancer cell. 2004; 5(4):375-87 (PubMed PMID: 15093544); Lakso M, et al., Proc Natl Acad Sci USA. 1992; 89(14):6232-6 (PubMed PMID: 1631115; PubMed Central PMCID: PMC49474); Olive K P, et al., Science. 2009; 324(5933):1457-61 (doi: 10.1126/science.1171362. PubMed PMID: 19460966; PubMed Central PMCID: PMC2998180); Guerra C, et al., Cancer cell. 2003; 4(2):111-20 (PubMed PMID: 12957286).

Recombinant adeno-associated virus (rAAV) was used to deliver gene targeting vectors to TP53$^{R167H/+}$ primary cells, similar to the process used to develop cystic fibrosis pigs. See, e.g., U.S. Pat. Nos. 7,989,675 and 8,618,352; Rogers C. S. et al., J Clin Invest. 2008; 118(4):1571-7 (Epub 2008/03/ 08. doi: 10.1172/JCI34773. PubMed PMID: 18324337; PubMed Central PMCID: PMC2265103). Approximately 1.5×10$^6$ $^{TP}$53$^{R167H/+}$ porcine fetal fibroblasts were infected with rAAV carrying the KRAS targeting vector (~100,000 MOI). After 24 hours, cells were transferred to a series of 96-well plates and G418 (100 µg/ml) was added to the media for selection of targeted cells. Two weeks later, 221 G418-resistant colonies were identified, isolated, and split among three sets of 96-well plates for; 1) cell expansion, 2) cryopreservation, and 3) PCR from cell lysates.

Figure 11:
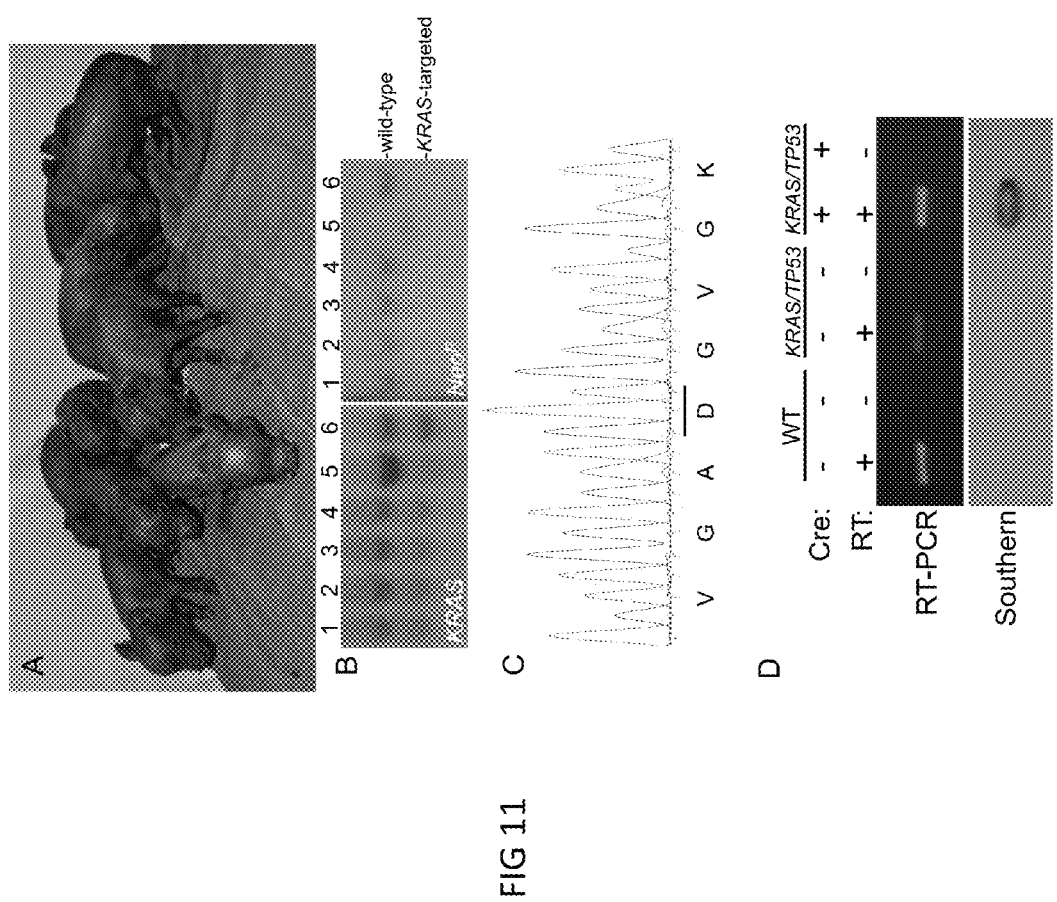
FIG. 11 shows KRAS/TP53 pigs generated by the methods described herein.

Cell lysates were screened by PCR and identified 28 KRAS-targeted clones, which were frozen for future SCNT. It is possible that in these KRAS-targeted cells the crossing over event occurred between the selectable marker and the desired G12D mutation. Therefore, an allele-specific Southern blot was used to identify 18 of the PCR-positive products that also contained G12D (FIG. 10B). By the time cells were frozen, they had been in culture only 15-17 days. We also passaged positive clones from the "cell expansion" plates to provide genomic DNA for downstream applications. Southern blots using KRAS- and Neo$^R$-specific probes identified KRAS-targeted clones that were free of random integration (data not shown, but similar blots are shown in FIG. 11). Furthermore, DNA sequence analysis confirmed the desired mutation. These clones are considered ideal for SCNT and were used to generate KRAS/TP53-targeted pigs.

Example 10

Generation of KRAS/TP53 Targeted Pigs

Four litters of KRAS$^{G12D/+}$/TP53$^{R167H/+}$ pigs (for simplicity, designated KRAS/TP53) were produced by SCNT using the KRAS/TP53 cells generated as set forth in Example 9 (FIG. 11A). The generation of these pigs confirms the viability of pigs produced by the processes described herein and provides cells and tissue in which to demonstrate Cre-mediated expression of KRAS$^{G12D}$. PCR, Southern blot analysis, and DNA sequencing were performed to confirm the expected genotype (FIGS. 11B and 11C).

KRAS/TP53 cells were isolated to test whether Cre-recombinase could induce expression of the G12D allele. Fibroblasts were infected with rAAV-Cre, and mRNA was isolated 24 hours later. RT-PCR was performed, followed by an allele-specific Southern blot to detect the presence of the G12D mutation. G12D mRNA was detected in KRAS/TP53 cells treated with Cre, but not in wild-type cells or untreated KRAS/TP53 cells (FIG. 11D).

Other Embodiments

Unless otherwise defined herein, all technical and scientific terms used herein have the ordinary meaning as commonly understood by one of ordinary skill in the art to which this invention pertains. Although methods and materials similar or equivalent to those described herein can be used in the practice or testing of the present invention, suitable methods and materials are described herein.

Although the invention has been described above in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

Other embodiments are within the following claims.

What is claimed:

1. A viable transgenic pig whose genome comprises a homozygous R167H mutation in exon 5 on both alleles of the endogenous p53 gene, wherein the p53 mutation results in an altered expression of a p53 translation product and/or in expression of a non-functional p53 protein; wherein said p53 mutation results in a phenotype of at least one of lymphoma, a renal tumor, a mesenteric tumor or an osteogenic tumor formation; and wherein said transgenic pig is the progeny of mated p53$^{R167H/+}$ founder pigs or a descendant of said progeny, wherein said p53$^{R167H/+}$ founder pigs are made by a process of introducing a p53$^{R167H}$ targeting vector into porcine fibroblast cells, utilizing the p53$^{R167H/+}$ fibroblasts as nuclear donors for somatic cell nuclear transfer (SCNT), thereby producing p53$^{R167H/+}$ founder pigs.

2. The transgenic pig of claim 1, wherein the homozygous R167H mutation in exon 5 of the endogenous pig p53 gene is a gain of function mutation.

3. The transgenic pig of claim 1, wherein the p53$^{R167H}$ targeting vector comprises SEQ ID NO: 1.

4. The transgenic pig of claim 1, wherein the p53$^{R167H}$ targeting vector further comprises a selectable marker gene flanked by LoxP sites, and upon introduction of Cre recombinase, the selectable marker gene is excised, thereby producing a selectable marker-free pig.

* * * * *

SEQUENCE LISTING

```
<160> NUMBER OF SEQ ID NOS: 41

<210> SEQ ID NO 1
<211> LENGTH: 4501
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gctgagttac ttcatcctga ttcccacaga ggagggcaga catgggtaca cgtggcggaa      60
ggcttgtgga ttcagtggtg aaggggggga caatccctct ctggttatct tttccccgcg     120
gggatgtgcg tggtgagggg tggggcaggt gcagcctggc atgtgaaggg cagggcgctg     180
ccccagcagc agagcctcac caccctgcgg cggtgtggac ggaggggtc cctcttccct      240 cggggcttgg gtgtgtctca ggctggatcc tggcctttct ccccacagcg gccacactcc     300
cctccaggga gctgcaatgg aggagtcgca gtccgagctg ggcgtggagc cccctctgag     360
tcaggagaca ttttcagact tgtggaaact gtgagtgag tctcaaggga gggctgcccg      420
tcttctaata accttgttcc cccccacca gcccccagcc cccaacccca gtagaggcct      480
ctgggaagca cagacctata ctgactctct gcccttgtct tccaggcttc ctgaaaacaa     540
cctgctggta aggactgggg cgcggcaagg gcaggggcct ggggggctgg ggggctggcc     600
tcctgactcc tgttgttccc atccatcgc agtcctctga gctctccctg gcagcagtga      660
acgatctgct gctgtcccca gtcacgaact ggctggatga aaatccagat gacgcctcca    720
gagtgccagc gcctcctgca gcaacagcgc ccgcaccagc tgccccgca ccagccacct     780 cctggcccct gtcgtccttt gtcccttctc agaagaccta ccctggcagc tatgatttcc    840
gtctagggtt cctgcattct ggaacagcca agtctgtaac ctgcacggtc agtggccttg    900
agggactggc ttcgtaggga cagtgcctgg cccctatccc cccgggtttt tctgtttaga    960
acttcgtggt tccactgcag cctttggctt tgtgtcaggc tttctatgtt taacctattt   1020
ggtctatgac cttggaccct ggtcccaaag ttgaatactc ccacttgacc ttggcctctc   1080
atccttccca tcacactctt cagcatttgt catgaggcca tggaactttt tttcttttct   1140
```

```
ctccactcat tcattccttg gcttttgtaa ggaagcttct gggagggagc ccccgaccct    1200
gccatctctg gctaccctcc ccaccgagca cttggctgga tatctgcaga attcggcttg    1260
tactgataac ttcgtatagc atacattata cgaagttgtt gcctgctatt gtcttcccaa    1320
tcctccccct tgctgtcctg ccccaccccca ccccccagaa tagaatgaca cctactcaga   1380
caatgcgatg caatttcctc attttattag gaaaggacag tgggagtggc accttccagg    1440
gtcaaggaag gcacggggga ggggcaaaca acagatggct ggcaactaga aggcacagtc    1500
gaggctgatc agcgagctct agagaattga tcccctcaga agaactcgtc aagaaggcga    1560
tagaaggcga tgcgctgcga atcgggagcg gcgataccgt aaagcacgag gaagcggtca    1620
gcccattcgc cgccaagctc ttcagcaata tcacgggtag ccaacgctat gtcctgatag    1680
cggtccgcca cacccagccg ccacagtcg atgaatccag aaaagcggcc attttccacc      1740
atgatattcg gcaagcaggc atcgccatgg gtcacgacga gatcctcgcc gtcgggcatg    1800
cgcgccttga gcctggcgaa cagttcggct ggcgcgagcc cctgatgctc ttcgtccaga    1860
tcatcctgat cgacaagacc ggcttccatc cgagtacgtg ctcgctcgat gcgatgtttc    1920
gcttggtggt cgaatgggca ggtagccgga tcaagcgtat gcagccgccg cattgcatca    1980
gccatgatgg atactttctc ggcaggagca aggtgagatg acaggagatc ctgccccggc    2040
acttcgccca atagcagcca gtcccttccc gcttcagtga acgtcgag cacagctgcg       2100
caaggaacgc ccgtcgtggc cagccacgat agccgcgctg cctcgtcctg cagttcattc    2160
agggcaccgg acaggtcggt cttgacaaaa agaaccgggc gcccctgcgc tgacagccgg    2220
aacacggcgc atcagagca gccgattgtc tgttgtgccc agtcatagcc gaatagcctc      2280
tccacccaag cggccggaga acctgcgtgc aatccatctt gttcaatggc cgatcccata    2340
ttggctgcag gtcgaaaggc ccggagatga ggaagaggag aacagcgcgg cagacgtgcg    2400
cttttgaagc gtgcagaatg ccgggcctcc ggaggacctt cgggcgcccg ccccgcccct    2460
gagcccgccc ctgagcccgc ccccggaccc accccttccc agcctctgag cccagaaagc    2520
gaaggagcaa agctgctatt ggccgctgcc ccaaaggcct acccgcttcc attgctcagc    2580
ggtgctgtcc atctgcacga gactagtgag acgtgctact tccatttgtc acgtcctgca    2640
cgacgcgagc tgcggggcgg gggggaactt cctgactagg ggaggagtag aaggtggcgc    2700
gaagggggcca ccaaagaacg gagccggttg gcgcctaccg gtggatgtgg aatgtgtgcg   2760
aggccagagg ccacttgtgt agcgccaagt gcccagcggg gctgctaaag cgcatgctcc    2820
agactgcctt gggaaaagta ctgataactt cgtatagcat acattatacg aagttgttga    2880
agccgaattc cagcacactg gcggccgtta ctagtggatc cgagctcggt accaagcttc    2940
taatcagtat ttaggcagcg tctgttcatt tgactgctgg ctccctgtcc tctgaccttc    3000
tgttcgctct ccatcctccc tttcctgcag tactcccctg ccctcaataa gctgttttgc    3060
cagctggcca agacctgccc ggtgcagctg tgggtcagct cgccaccccc gcctggcacc    3120
cgtgtccgcg ccatggccat ctacaagaag tcagagtaca tgaccgaggt ggtgaggcgc    3180
tgtccccacc atgagcgcag ctctgactat agcgatggtg agcgggcggg ggctgtgggt    3240
gggacagggc tggtgcccgg agctgccaaa cccctcattc ccaccccacc ccccattgc     3300
tctcaggtct ggcccctccc cagcatctca tccgggtgga agggaattta cgggccgagt    3360
acttggatga cagaaacact tttcgacaca gcgtggtggt gccctacgag ccgcccgagg    3420
tctggtttgg cccctggggt ctccggggag agggggccag aggggtttgt ccgtggcctt    3480
cctggtggga gatgggggcg gcttttctcct tctcacttga cctgccgcag cctcgtgagg    3540
```

-continued

| | |
|---|---|
| cgggtagagc agatgggtta cccccattcc acagctgagg cgcccagagg ccagtggcct | 3600 |
| gccggggcta gtagggtcac cttgggcctg tgtcgtcccc caggtcggct ctgactgtac | 3660 |
| caccatccac tacaacttca tgtgcaacag ctcctgcatg gggggcatga accggcggcc | 3720 |
| catcctcacc atcatcacac tggaagacgc caggtagggg ccgcacaccg ccctccacgc | 3780 |
| tggcgggccc ctcctcagcc tctgcctgtc tccatggccc tgccgctcat ccccttctcc | 3840 |
| cgggcttcca gccatccttc cctctggctg cagccacttt gcgtccctct gctgctccct | 3900 |
| cccagtgccc ttttccccgg ctttggcacc cctcttacct gtggcttctt gatcagctgg | 3960 |
| agctgaggct cctcgtagga tgcggggat ggggagggg tggggccccg ctcacagagc | 4020 |
| agggaggccg ggctggcttt cctcactgcc tcctacttcc ccccggggta gtggcaactt | 4080 |
| gctgggacgg aacagctttg gggtgcgtgt ttgtgcctgt cctgggagag accgccgcac | 4140 |
| agaggaagaa aatttcctca agaagggcca atcttgcccc gagccgcccc ctggcagcac | 4200 |
| taagcgaggt aagcaggcag gaccagaagg ggtagagggg acaggagggg ggcggttctg | 4260 |
| cccaaaatgc actcttttct caccttttcct caccccttc ccagcactgc ccaccagcac | 4320 |
| cagctcctcg ccagtgcaaa agaagaagcc actggatggc gagtatttca ccctccaggt | 4380 |
| atcaagtctg ggagagagag gggccgtttc ctgctcttac tcagtggggt tggataaggg | 4440 |
| gagaaaagct acaaaggtag caggtgtgag gttatgccca gtttctctag ccatccttt | 4500 |
| g | 4501 |

<210> SEQ ID NO 2
<211> LENGTH: 4501
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | |
|---|---|
| gattgattaa tagaataatg tgacttgaga attgtcttct caggcaaaat gctgggggaa | 60 |
| atgcaaattg ggacattcct ctattcacag gtaatctgac aatatctacg aaattacaga | 120 |
| cacatttact catcaatcca gctttaggaa gtctacccaa agactcacct gcgcatgtat | 180 |
| gaaatactac atgttcaaag tcattcactg cagcctagca ttgtttgcta ctgcaaagga | 240 |
| ctacaagcaa cccaaatgcc cattttatac aataaagact tgtatgataa ccatgtacta | 300 |
| acacacaaag cagctgttaa aaaagagaaa caatttttata acatactgtt gagttaaaca | 360 |
| gatatataca taaagaataa acttttatat ttatatatca aagtgtatat gtagcccttt | 420 |
| ctctaagaaa ggagggtaag aaggaaatat attcatatat tccatttgta taacactgga | 480 |
| aacaaatgaa aatggtactt ataagggtga ggaggggcca tgaggttgat aggaaaaagg | 540 |
| gtgagagaag gtttcccttt ttatatgttt ttctattatt ggattttga agaaagaaaa | 600 |
| tgtattaaaa caaaaaaaaa ttttttttat ttttatcttt taacagctgt acctgggcca | 660 |
| tctggaagtt cctaggctag gggccgaatt agagctgcag ctgccagcct acaccacggc | 720 |
| cacagcaatg acagatttga gccacagctg tgacctatgc caaagcctgc tacagtgctg | 780 |
| gatccttaac ccactgagtg aggccaggaa ttgagcccac atcctcgtgg acactatatt | 840 |
| gggtttttaa catcctaaaa agttttaaaa ccctatatta tgtactatat tcttcactaa | 900 |
| atcagtattg tctttttact accactttcc ttccttaagag tacttctata ccagaaatag | 960 |
| gccaaatggt caaacataag gggaaaatac ttttcagcta attacaagaa ataagatttc | 1020 |

```
ttgaaacaaa aaattgctgc attgaacatt aatgtgtact ttttaaaaag aaaatattgt    1080
ctaaatcaga ggttggcaat atacggtctt tggaccaaac ccagtcccag actattttg     1140 tatagcctgt gagctaagga tggtttaaag ggatataaag aaaaaaataa agaatatgca    1200
agagagacct tatgcggctc acaaaaatct aaaatattta ctatctggtc ctccacagaa    1260
aacatttgct gacccttggc tgaataatgg catcttttat atgttcttaa tgaagcagca    1320
gaagtacaaa ctagttacct tatatgtgca gatagtcagt ttcctcttcc tggtttcagt    1380
gtttctctgc agtaacgtat taagcttggt accgagctcg gatccactag taacggccgc    1440
cagtgtgctg gaattcggct tcaacaactt cgtataatgt atgctatacg aagttatcag    1500
tactttcccc aaggcagtct ggagcatgcg ctttagcagc cccgctgggc acttggcgct    1560
acacaagtgg cctctggcct cgcacacatt ccacatccac cggtaggcgc caaccggctc    1620
cgttctttgg tggcccctc gcgccacctt ctactcctcc cctagtcagg aagttccccc     1680
ccgccccgca gctcgcgtcg tgcaggacgt gacaaatgga agtagcacgt ctcactagtc    1740
tcgtgcagat ggacagcacc gctgagcaat ggaagcgggt aggcctttgg ggcagcggcc    1800
aatagcagct ttgctccttc gctttctggg ctcagaggct gggaaggggt gggtccgggg    1860
gcgggctcag gggcgggctc aggggcgggg cgggcgcccg aaggtcctcc ggaggcccgg    1920
cattctgcac gcttcaaaag cgcacgtctg ccgcgctgtt ctcctcttcc tcatctccgg    1980 gccttttcgac ctgcagccaa tatgggatcg ccattgaac aagatggatt gcacgcaggt    2040
tctccggccg cttgggtgga gaggctattc ggctatgact gggcacaaca gacaatcggc    2100
tgctctgatg ccgccgtgtt ccggctgtca gcgcaggggc gcccggttct ttttgtcaag    2160
accgacctgt ccggtgccct gaatgaactg caggacgagg cagcgcggct atcgtggctg    2220
gccacgacgg gcgttccttg cgcagctgtg ctcgacgttg tcactgaagc gggaagggac    2280
tggctgctat tgggcgaagt gccggggcag gatctcctgt catctcacct tgctcctgcc    2340
gagaaagtat ccatcatggc tgatgcaatg cggcggctgc atacgcttga tccggctacc    2400
tgcccattcg accaccaagc gaaacatcgc atcgagcgag cacgtactcg gatggaagcc    2460
ggtcttgtcg atcaggatga tctggacgaa gagcatcagg ggctcgcgcc agccgaactg    2520
ttcgccaggc tcaaggcgcg catgcccgac ggcgaggatc tcgtcgtgac ccatggcgat    2580
gcctgcttgc cgaatatcat ggtggaaaat ggccgctttt ctggattcat cgactgtggc    2640
cggctgggtg tggcggaccg ctatcaggac atagcgttgg ctacccgtga tattgctgaa    2700
gagcttggcg gcgaatgggc tgaccgcttc ctcgtgcttt acggtatcgc cgctcccgat    2760
tcgcagcgca tcgccttcta tcgccttctt gacgagttct tctgagggga tcaattctct    2820
agagctcgct gatcagcctc gactgtgcct tctagttgcc agccatctgt tgtttgcccc    2880
tcccccgtgc cttccttgac cctggaaggt gccactccca ctgtcctttc ctaataaaat    2940
gaggaaattg catcgcattg tctgagtagg tgtcattcta ttctgggggg tggggtgggg    3000
caggacagca agggggagga ttgggaagac aatagcaggc atgctgggga tgcggtgggc    3060
gctatacgaa gttatcagta caagccgaat tctgcagata tccacatctc ggaaaacctg    3120
ctgcatgact gcatcttgtc tcaggtcatc acggcccttc agaataatca caatatgaat    3180
aactaagcac agttcatttc ttcattgtca gatgatacag tcatctgagg acagctaaaa    3240
ggcactgaga aatcaatctg agcatccatg ctcctcataa tagtctctca atgaattaag    3300
acctaagatt attctttcat ttagaataag ctataccact gggtaggcag accgatttag    3360
aagaaagaag gtcccccctgc cagctgcttt tgtaattaaa cccactggaa ctcctccacc    3420
```

```
tgagggccca ctgcaaacat caggcagagc agcacctttg tctgtactac tttgcagcga    3480
aacccaaaga gccggagagc agagggaggg agggacgggc aaagcactca gcacagggcc    3540
agacttggtc cttcactcca actattcaag aaaagaagca accaccaaaa catggttttt    3600
tcccataaca agcaggctga ttgttaacct catcatgcct gtacatgcta aaagtattct    3660
ttatggggtt cccactgtgg cacagcaggt taaggatctg gtgttgccac agctgtggtg    3720
taggttgtag ctgtggcttg gacttgatcc ctgacccag gaacttccat atgtcatggg     3780
tgaggcaaaa aacaaaaaaa gattctttca accaactatt ataataagtc tagtcttgca    3840
gagacacaaa aaaatgagaa aaagcattct gcttctagaa ataaatacat ttgttttcct    3900
cacctgtaat tattcagaat aaaaataaaa gcccaaagca agaagaaaat atcaattata    3960
gttttctatg acttctttca ttaaccaact aggaaccaca ccacaaaaaa aagtttcacc    4020
ttgacaagct gtcgcctttc cttgccatca gagccgacac aatctattat ttttggtaaa    4080
tttaaacctc ctgctaaacg aaattctggt ttaaatgact gtatagtcac catgttttcca   4140 tattctcctg tggggtccac ctaataaaat gtacaaatat gacaataggt cagatacaca    4200
atttgaattt aaagaaaaat gaattataag tgacaactgt ggtattaaac agaggaacga    4260
atgacaatgt gctgttgatt aagacttgaa gtgataaatt tataaatgaa aggaagaaga    4320
tttgacattg gaaaggcttt taaaaagtga cacagataac acaatttatc tccctaaata    4380
tcactttaaa aaagtaggtc atacaaagtt agaattcat tgctaaaaaa ctactgaaaa      4440
acctgggttt aggtcttgcc atagacctat atatggtaag tcatctgaga aatagtaagc    4500
t                                                                   4501

<210> SEQ ID NO 3
<211> LENGTH: 4509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gcggccgcag gctagggtgc cactaatgta atacaacagt tgtttggtct gtctctttgt      60
gagtgggttc aagaagaggg tgaggaggtg tttaatatgt tatcatgtgg aaaaccatgt    120
aacttttttg agggtagagg gtggagtgcg tatttggata attcttggtc ttcagtaaat    180
tggatgctgc ctttgtatct agtgcttata tacaacatct gtacattcat taatttagaa    240
ccagcttatg ctgtattaat tattgtgcat cgacttccat tctctccgca attcactact    300
tgtttgtaat agtaccatgt agttattgag tgataggaga ttaaagtaag taagttcatt    360
tttatctcaa aaagtttgaa atagctgact aaaagaatat tttctgtctt gcattgttaa    420
ccttacaagt tggcaatatt tattgctact gttgggagat gatggatgag aagcggagaa    480
ttaaagtcat gtgcattact gagaaatatt cacttatatc ttttaaaaat tctttcatta    540
aaagcggtac ttgcctttaa tattatacaa ttcattttt gtgcaaagtt ctattttca     600 gcactaatac agaattatat atgtgatcga tgatcatatc atctgtactg aatagttagt    660
tcaaaattct caaagttctt ttagttttg caccgttctt ttcctcagca gatactttac      720
agattaaaat gtcaaaaatt attgtcctta tctgctttgg cgtctcagtt tttagttttcc   780 cagcgcacca tccagctttg acagtcctct ccccgctcca ttcagattct tgctaactct    840
tcaagagaac tttgatgatg ctttcaaaaa agttttctgt agctcttgac tccagcagag    900
```

```
acactcagca tatccacttg taactcttgg ggcccaagtc aatgaggatt actgtggcta    960
aagtagccaa attttgtgtg ggtgtgttca caggatatag cgcagcttgc tcctcacttg   1020
ttctgagtga agtcatggcc cactcctttg agagccatta gctgctgcag atcagcagat   1080
tggctcttca gatagagcaa cccggagttc ccgtcgtggc acagtggtta acgaatccga   1140
ctaggaacca tgaggttgtg ggttcggtcc ctgaccttgc tcagtgggtt aaggatctgg   1200
cgttgccatg agctgtgatg taggctgcag acacggcttg gatcccacat tgctatggcc   1260
ctggtgtagg ccggcggcta cagctctgat tagaccccta tcctgggaat ggctctagaa   1320
aaggcaaaaa caaacaaaaa aacaaaaaca gagcaacctg aatctaaggt aaaagaactg   1380
tgtactctga aagcattttt ctcaaatgct gatgggggca ttcataaatg aagtacagtt   1440
caatatattg cacatctgtg gtcaacgggc gttttcatcg ctaaactttg tgaggtattt   1500
tgaaacaatt tttcatatac aggtataact tcgtatagca tacattatac gaagttgtta   1560
ggtccctcga cctgcaggaa tttcgaggct agaactagtg gatcccccgg gctgcagatc   1620
tgtagggcgc agtagtccag ggtttccttg atgatgtcat acttatcctg tccctttttt   1680
ttccacagct cgcggttgag gacaaactct tcgcggtctt ccagtgggg  atcgacggta   1740
tcgataagct tgatgatctg tgacatggga tcggccattg aacaagatgg attgcacgca   1800
ggttctccgg ccgcttgggt ggagaggcta ttcggctatg actgggcaca acagacaatc   1860
ggctgctctg atgccgccgt gttccggctg tcagcgcagg ggcgcccggt tctttttgtc   1920
aagaccgacc tgtccggtgc cctgaatgaa ctgcaggacg aggcagcgcg gctatcgtgg   1980
ctggccacga cgggcgttcc ttgcgcagct gtgctcgacg ttgtcactga agcgggaagg   2040
gactggctgc tattgggcga agtgccgggg caggatctcc tgtcatctca ccttgctcct   2100
gccgagaaag tatccatcat ggctgatgca atgcggcggc tgcatacgct tgatccggct   2160
acctgcccat tcgaccacca agcgaaacat cgcatcgagc gagcacgtac tcggatggaa   2220
gccggtcttg tcgatcagga tgatctggac gaagagcatc aggggctcgc gccagccgaa   2280
ctgttcgcca ggctcaaggc gcgcatgccc gacggcgagg atctcgtcgt gacccatggc   2340
gatgcctgct tgccgaatat catggtggaa aatggccgct tttctggatt catcgactgt   2400
ggccggctgg gtgtggcgga ccgctatcag gacatagcgt tggctacccg tgatattgct   2460
gaagagcttg gcggcgaatg ggctgaccgc ttcctcgtgc tttacggtat cgccgctccc   2520
gattcgcagc gcatcgcctt ctatcgcctt cttgacgagt tcttctgagg ggatcaattc   2580
tctagagctc gctgatcagc ctcgactgtg ccttctagtt gccagccatc tgttgtttgc   2640
ccctcccccg tgccttcctt gaccctggaa ggtgccactc ccactgtcct ttcctaataa   2700
aatgaggaaa ttgcatcgca ttgtctgagt aggtgtcatt ctattctggg ggtgggggtg   2760
gggcaggaca gcaagggga ggattgggaa gacaatagca ggcataact tcgtatagca   2820
tacattatac gaagttgtca atttgtgtta agagggcttg atagcgtttg gttatatta   2880
acctcatatg tggcacatgt tctaatttag tcacattttc attattttta ttataaggcc   2940
tgctgaaaat gactgaatat aaacttgtgg tagttggagc tgatggcgta ggcaagagtg   3000
ccttgacgat acagctaatt cagaatcact ttgtggatga atatgatcct acgatagagg   3060
taaatcttgt tttactgtta tgcatattga cttgtgcagg cccatccttt gggtacaaaa   3120
aaggtttctc tggtcatttt ctaaaactac gcattacaag acagttattc tgataatacc   3180
taagttatct gcaatgcact tgggtttcaa ggctttactc tgatgttata tgtaaccaca   3240
gacatggaga gcccagtgtt gagtcttcag tcttctctgg ggagaataat accatctgca   3300
```

```
atgttcactc tgagctagta tatgtgcatt ttgattgaaa gtgtacttgt gagtttagca      3360
gagggtgaaa atgtgaactt acatcctatt tgtaaaaaga gacatatcta acagttattt      3420
tcctaaaaat gtggctattg tccgtatggg gttttggtgt tttgggggta tattttgatg      3480
tcacatgttg aattgatggg tactggtaaa gtggaatcat ttgatgatgg aattaaaaac      3540
acttaattag tagtattttc aagttttctc ttcacattga agtactggag aacctgcagc      3600
tacctgtgtg ttttagaaaa gctcattctt ttatgtatgt gtatgttggg cgatgtataa      3660
gggtaggtac cacactagtc cttacctttc ctgtgcagtc ctttttcagt gtactgaagg      3720
aaatattaga attgtttttta ttacaaatca attactgtaa ttttcaggct ttttcagttt      3780
catgagaatg taccaaaagc aaggccaaca gcataatgat agaataaagg cctggcagag      3840
atcttgagag gtcaaatgat ctcaagcaga tagggattta tttaatccta gagacctgca      3900
aggagggaac ggcacctaac tgtgttaact aatttctgaa atgtaattag catattttat      3960
gcataatgtg aatcttcctg ttaagtttaa catagcatca gtttgtcttt gaaatagatt      4020
tatgctgtta aattatttcc aaaaacttct ttaccccagc ttaagtaatc ctaattaatc      4080
ccttactttt tattctagat ctgatatacc agttttttaa atcagctctg aaaaatgtcc      4140
cagaattttc tctgagtctc aagctacaga ttgtagaaca ggtcagaatg ccctgttagg      4200
atgttgtata aagtcttcaa gaaacacctt gaccacactg aggtagattc aaagggcatg      4260
gttagccttt taagacgttt atgcagggta gaacttgag gattgattag ataactgctc       4320
ataaggaaat gtcaaatatt tttggtactg caggggaaga aaatggaaaa taacccgtat      4380
ttgcaaagat ctgatttaaa catagaaaca gcttttattt ggcttccagg tttaataatt      4440
tgcagtagca aatggaaaga gtctaactaa gtggaccaca tatgtaatag tctctatatt      4500
tgcggccgc                                                             4509

<210> SEQ ID NO 4
<211> LENGTH: 4510
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gcggccgcat acagaattat atatgtgatc gatgatcata tcatctgtac tgaatagtta        60
gttcaaaatt ctcaaagttc ttttagtttt tgcaccgttc ttttcctcag cagatacttt       120
acagattaaa atgtcaaaaa ttattgtcct tatctgcttt ggcgtctcag tttttagttt       180
cccagcgcac catccagctt tgacagtcct ctccccgctc cattcagatt cttgctaact       240
cttcaagaga actttgatga tgctttcaaa aaagttttct gtagctcttg actccagcag       300
agacactcag catatccact tgtaactctt ggggcccaag tcaatgagga ttactgtggc       360
taaagtagcc aaattttgtg tgggtgtgtt cacaggatat agcgcagctt gctcctcact       420
tgttctgagt gaagtcatgg cccactcctt tgagagccat tagctgctgc agatcagcag       480
attggctctt cagatagagc aacccggagt tcccgtcgtg gcacagtggt taacgaatcc       540
gactaggaac catgaggttg tgggttcggt ccctgacctt gctcagtggg ttaaggatct       600
ggcgttgcca tgagctgtga tgtaggctgc agacacggct tggatccac attgctatgg       660 ccctggtgta ggccggcggc tacagctctg attgacccc tatcctggga atggctctag       720
aaaaggcaaa acaaacaaa aaacaaaaa cagagcaacc tgaatctaag gtaaaagaac         780
```

```
tgtgtactct gaaagcattt ttctcaaatg ctgatggggg cattcataaa tgaagtacag    840
ttcaatatat tgcacatctg tggtcaacgg gcgttttcat cgctaaactt tgtgaggtat    900
tttgaaacaa tttttcatat acaggataac ttcgtatagc atacattata cgaagttata    960
ttaagggttc cgtgcctgct attgtcttcc caatcctccc ccttgctgtc ctgcccacc    1020
ccacccccca gaatagaatg cacctactc agacaatgcg atgcaatttc ctcattttat   1080
taggaaagga cagtgggagt ggcaccttcc agggtcaagg aaggcacggg ggaggggcaa   1140
acaacagatg gctggcaact agaaggcaca gtcgaggctg atcagcgagc tctagagaat   1200
tgatcccctc agaagaactc gtcaagaagg cgatagaagg cgatgcgctg cgaatcggga   1260
gcggcgatac cgtaaagcac gaggaagcgg tcagcccatt cgccgccaag ctcttcagca   1320
atatcacggg tagccaacgc tatgtcctga tagcggtccg ccacacccag ccggccacag   1380
tcgatgaatc cagaaaagcg gccattttcc accatgatat tcggcaagca ggcatcgcca   1440
tgggtcacga cgagatcctc gccgtcgggc atgcgcgcct tgagcctggc gaacagttcg   1500
gctggcgcga gcccctgatg ctcttcgtcc agatcatcct gatcgacaag accggcttcc   1560
atccgagtac gtgctcgctc gatgcgatgt ttcgcttggt ggtcgaatgg gcaggtagcc   1620
ggatcaagcg tatgcagccg ccgcattgca tcagccatga tggatacttt ctcggcagga   1680
gcaaggtgag atgacaggag atcctgcccc ggcacttcgc ccaatagcag ccagtcccctt   1740
cccgcttcag tgacaacgtc gagcacagct gcgcaaggaa cgcccgtcgt ggccagccac   1800
gatagccgcg ctgcctcgtc ctgcagttca tcagggcac cggacaggtc ggtcttgaca   1860
aaaagaaccg ggcgcccctg cgctgacagc cggaacacgg cggcatcaga gcagccgatt   1920
gtctgttgtg cccagtcata gccgaatagc ctctccaccc aagcggccgg agaacctgcg   1980
tgcaatccat cttgttcaat ggccgatccc atattggctg caggtcgaaa ggcccggaga   2040
tgaggaagag gagaacagcg cggcagacgt gcgcttttga agcgtgcaga atgccgggcc   2100
tccggaggac cttcgggcgc ccgccccgcc cctgagcccg ccctgagcc cgcccccgga   2160
cccacccctt cccagcctct gagcccagaa agcgaaggag caaagctgct attggccgct   2220
gccccaaagg cctacccgct tccattgctc agcggtgctg tccatctgca cgagactagt   2280
gagacgtgct acttccattt gtcacgtcct gcacgacgcg agctgcgggg cgggggggaa   2340
cttcctgact aggggaggag tagaaggtgg cgcgaagggg ccaccaaaga acggagccgg   2400
ttggcgccta ccggtggatg tggaatgtgt gcgaggccag aggccacttg tgtagcgcca   2460
agtgcccagc ggggctgcta aagcgcatgc tccagactgc cttgggaaaa gtactgtcga   2520
gggatctttg tgaaggaacc ttacttctgt ggtgtgacat aattggacaa actacctaca   2580
gagatttaaa gctctaaggt aaatataaaa ttttaagtg tataatgtgt taaactactg   2640
attctaattg tttgtgtatt ttagattcca acctatggaa ctgatgaatg ggagcagtgg   2700
tggaatgcct ttaatgagga aaacctgttt tgctcagaag aaatgccatc tagtgatgat   2760
gaggctactg ctgactctca acattctact cctccaaaaa agaagagaaa ggtagaagac   2820
cccaaggact ttccttcaga attgctaagt tttttgagtc atgctgtgtt tagtaataga   2880
actcttgctt gctttgctat ttacaccaca aaggaaaaag ctgcactgct atacaagaaa   2940
attatggaaa aatattctgt aacctttata agtaggcata acagttataa tcataacata   3000
ctgttttttc ttactccaca caggcataga gtgtctgcta ttaataacta tgctcaaaaa   3060
ttgtgtacct ttagcttttt aatttgtaaa ggggttaata aggaatattt gatgtatagt   3120
gccttgacta gagatcataa tcagccatac cacatttgta gaggttttac ttgctttaaa   3180
```

```
aaacctccca cacctccccc tgaacctgaa acataaaatg aatgcaattg ttgttgttaa    3240
cttgtttatt gcagcttata atggttacaa ataaagcaat agcatcacaa atttcacaaa    3300
taaagcattt ttttcactgc attctagttg tggtttgtcc aaactcatca atgtatctta    3360
tcatgtctgg atctgacatg gtaagtaagc ttgggctgca ggtcgaggga cctaataact    3420
tcgtatagca tacattatac gaagttattc aatttgtgtt aagagggctt gatagcgttt    3480
gggttatatt aacctcatat gtggcacatg ttctaattta gtcacatttt cattattttt    3540
attataaggc ctgctgaaaa tgactgaata taaacttgtg gtagttggag ctgatggcgt    3600
aggcaagagt gccttgacga tacagctaat tcagaatcac tttgtggatg aatatgatcc    3660
tacgatagag gtaaatcttg ttttactgtt atgcatattg acttgtgcag gcccatcctt    3720
tgggtacaaa aaaggtttct ctggtcattt tctaaaacta cgcattacaa gacagttatt    3780
ctgataatac ctaagttatc tgcaatgcac ttgggtttca aggctttact ctgatgttat    3840
atgtaaccac agacatggag agcccagtgt tgagtcttca gtcttctctg gggagaataa    3900
taccatctgc aatgttcact ctgagctagt atatgtgcat tttgattgaa agtgtacttg    3960
tgagtttagc agagggtgaa aatgtgaact tacatcctat ttgtaaaaag agacatatct    4020
aacagttatt ttcctaaaaa tgtggctatt gtccgtatgg ggttttggtg tttttgggggt    4080 atattttgat gtcacatgtt gaattgatgg gtactggtaa agtggaatca tttgatgatg    4140
gaattaaaaa cacttaatta gtagtatttt caagttttct cttcacattg aagtactgga    4200
gaacctgcag ctacctgtgt gttttagaaa agctcattct tttatgtatg tgtatgttgg    4260
gcgatgtata agggtaggta ccacactagt ccttacctt tcctgtgcagt ccttttttcag   4320 tgtactgaag gaaatattag aattgttttt attacaaatc aattactgta attttcaggc    4380
tttttcagtt tcatgagaat gtaccaaaag caaggccaac agcataatga tagaataaag    4440
gcctggcaga gatcttgaga ggtcaaatga tctcaagcag atagggatt atttaatcct    4500 aggcggccgc                                                            4510

<210> SEQ ID NO 5
<211> LENGTH: 18
<212> TYPE: DNA
<213> ORGANISM: Sus sp.

<400> SEQUENCE: 5
ggtgaggcgc tgtcccca                                                    18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtgaggcac tgtcccca                                                    18

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 7
cgctctcaat aatagagaac c                                              21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaaatcatgc agtgaattta agt                                            23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctaggtcaac ataaaggagc g                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgagctggga gatgagatga                                                20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agggtgctag aagatgagat c                                              21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgcaatggag gagtcgcag                                                 19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 13
cctggcagct atgatttccg                                        20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtgcagctgt gggtcagc                                          18

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctcacttgac ctgccgcag                                         19

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gctggctttc ctcactgc                                          18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcttgactct tgtagtgcat a                                      21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgagttaag aactggacta g                                      21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 19
ttcccacttc tagcaaccct                                               20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctgcgactcc tccattgca                                                19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cggaaatcat agctgccagg                                               20

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gatcgagata tcgaggtgtt ttcagtgcca tta                                33

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gatcgagata tccagccaag tgctcggtgg                                    30

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gatcgaggat ccctaatcag tatttaggca gcg                                33

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 25
gatcgaaagc ttggttgcag aagagactcc g                              31

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgaccgaggt ggtgaggcac tgtccccacc atgagcg                        37

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgctcatggt ggggacagtg cctcaccacc tcggtca                        37

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agctacatgc ggccgcgctg agttacttca tcctgat                        37

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agctacatgc ggccgccaaa aggatggcta gagaaac                        37

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agacgtgcta cttccatttg tcac                                      24

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tcaatctctc aaacccgata g          21

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agccacagct catcactcc          19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agcactggaa ctcgtcagg          19

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtgaggcact gtcccc          16

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccagtgtgct ggaattcgg          19

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctgcagaatt cggcttgtac t          21

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 37
gatgtggctc ggatctggt                                                  19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccatgttcct ccctgctcc                                                  19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggctgctaaa gcgcatgct                                                  19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
accctgccat ctctggcta                                                  19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agagcgaaca gaaggtcaga                                                 20
```